United States Patent
Goetzl

(10) Patent No.: US 12,372,538 B2
(45) Date of Patent: Jul. 29, 2025

(54) EXOSOME ASSAY FOR DEPRESSION AND PSYCHOSIS AND METHODS AND AGENTS FOR TREATING DEPRESSION, PSYCHOSIS AND SCHIZOPHRENIA

(71) Applicant: Edward J Goetzl, San Francisco, CA (US)

(72) Inventor: Edward J Goetzl, San Francisco, CA (US)

( * ) Notice: Subject to any disclaimer, the term of this patent is extended or adjusted under 35 U.S.C. 154(b) by 520 days.

(21) Appl. No.: 17/362,975

(22) Filed: Jun. 29, 2021

(65) Prior Publication Data
US 2022/0128575 A1  Apr. 28, 2022

Related U.S. Application Data

(60) Provisional application No. 63/128,095, filed on Dec. 19, 2020, provisional application No. 63/045,190, filed on Jun. 29, 2020.

(51) Int. Cl.
*G01N 33/68* (2006.01)
(52) U.S. Cl.
CPC . *G01N 33/6896* (2013.01); *G01N 2333/4716* (2013.01); *G01N 2333/5412* (2013.01); *G01N 2333/70596* (2013.01); *G01N 2800/28* (2013.01); *G01N 2800/60* (2013.01)
(58) Field of Classification Search
CPC ....... G01N 33/6896; G01N 2333/4716; G01N 2333/5412; G01N 2333/70596; G01N 2800/28; G01N 2800/60
See application file for complete search history.

(56) References Cited

PUBLICATIONS

Schiavone, Stefania, and Luigia Trabace. "Pharmacological targeting of redox regulation systems as new therapeutic approach for psychiatric disorders: A literature overview." Pharmacological research vol. 107 (2016): 195-204. doi:10.1016/j.phrs.2016.03.019 (Year: 2016).*
Kuwano, Nobuki et al. "Neuron-related blood inflammatory markers as an objective evaluation tool for major depressive disorder: An exploratory pilot case-control study." Journal of affective disorders vol. 240 (2018): 88-98. doi:10.1016/j.jad.2018.07.040 (Year: 2018).*
Rajkowska, G, and J J Miguel-Hidalgo. "Gliogenesis and glial pathology in depression." CNS & neurological disorders drug targets vol. 6,3 (2007): 219-33. doi:10.2174/187152707780619326 (Year: 2007).*
Piao C-S, Holloway AL, Hong-Routson S, Wainwright MS. Depression following traumatic brain injury in mice is associated with down-regulation of hippocampal astrocyte glutamate transporters by thrombin. Journal of Cerebral Blood Flow & Metabolism. 2019; 39(1):58-73. doi:10.1177/0271678X17742792 (Year: 2019).*
Li, Pin et al. "Progress in Exosome Isolation Techniques." Theranostics vol. 7,3 789-804. Jan. 26, 2017, doi:10.7150/thno.18133 (Year: 2017).*
Edward Goetzl, Neural cell-derived plasma exosome protein abnormalities implicate mitochondrial impairment in first episodes of psychosis, FASEB Journal. 2021;35:e21339.
Edward Goetzl, Decreased mitochondrial electron transport proteins and increased complement mediators in plasma neural-derived exosomes of early psychosis, Translational Psychiatry (2020) 10:361.

* cited by examiner

*Primary Examiner* — Gregory S Emch
*Assistant Examiner* — McKenzie A Dunn
(74) *Attorney, Agent, or Firm* — Law Office of Christopher Jacob, P.C.

(57) ABSTRACT

The present disclosure relates to exosomal complement mediators, cytokines, and mitochondrial electron transport biomarkers and diagnostic and prognostic methods for depression, psychosis and schizophrenia. The disclosure also provides compositions for detecting exosomal complement mediators, cytokines, and mitochondrial electron transport biomarkers in biological samples as well as compositions and methods useful for treating depression, psychosis and schizophrenia.

16 Claims, 33 Drawing Sheets

EXOSOME ASSAY FOR DEPRESSION AND PSYCHOSIS AND METHODS AND AGENTS FOR TREATING DEPRESSION, PSYCHOSIS AND SCHIZOPHRENIA

RELATED APPLICATIONS

This application claims priority to the U.S. Provisional Patent Application Ser. No. 63/045,190, filed on Jun. 29, 2020 and U.S. Provisional Patent Application Ser. No. 63/128,095, filed on Dec. 19, 2020, which are hereby incorporated by reference herein in their entirety.

FIELD OF THE INVENTION

The present disclosure relates to exosomal complement mediators, cytokines, and mitochondrial electron transport biomarkers and diagnostic and prognostic methods for depression, psychosis and schizophrenia. The disclosure also provides compositions for detecting exosomal complement mediators, cytokines, and mitochondrial electron transport biomarkers in biological samples as well as compositions and methods useful for treating depression, psychosis and schizophrenia.

BACKGROUND OF THE INVENTION

Most studies of the neurobiology of schizophrenia have focused on neurotransmitter systems, their receptors, and downstream effectors. In the past decade, however, many findings of astroglial cell abnormalities in human brain tissues from schizophrenia patients, involving their numbers, gene expression, neuromediator metabolism and interactions with neurons have suggested a central role in pathogenesis (Kerns et al. Schizophr Res. 2010; 120:150-158; Katsel et al. Neuropsychopharmacology. 2011; 36:1171-1177; Bernstein et al. Schizophr Res. 2015; 161:4-18; Mei et al. Front Psychiatry. 2018; 9:544; and Tarasov et al. Front Pharmacol. 2019; 10:1612). Astrocytes are abundant glial cells of the central nervous system that normally serve diverse trophic roles for neurons (Sofroniew et al. Acta Neuropathol. 2010; 119:7-35). In many inflammatory and degenerative neurological diseases, however, astrocytes increase in number, are transformed into A1 reactive/inflammatory-type astrocytes and contribute to destruction of neurons (Choi et al. PLoS One. 2014; 9:e92325; Ben et al. Front Cell Neurosci. 2015; 9:278; and Liddelow et al. Immunity. 2017; 46:957-967). The mechanisms by which inflammatory-type astrocytes damage neurons in diseases have not been elucidated fully. Astrocytes and other neural cells secrete extracellular vesicles termed exosomes that contain proteins, nucleic acids and lipids representative of the cells of origin and reflective of physiological and pathological changes in these cells (Goetzl at al. Faseb J. 2016; 30:3853-3859). The recently developed capacity to specifically enrich astrocyte-derived exosomes (ADEs) from plasma of living subjects has enabled investigations into the roles of inflammatory astrocytes in Alzheimer's disease (AD) and traumatic brain injury (TBI) (Goetzl et al. Ann Neurol. 2018; 83:544-552; Goetzl et al. Faseb J. 2020; 34:3359-3366).

Among the most functionally prominent constituents of ADEs from inflammatory-type astrocytes are proteins of the complement systems. Of the many complement components, the most damaging to neurons are C3b and C5b-9 terminal attack complex. C3b coats neurons and thereby facilitates high-affinity attachment of phagocytic microglia and their consequent neurotoxicity. C5b-9 attaches to and attacks neuronal plasma membranes with a direct neurotoxic outcome. In MCI that progresses to AD dementia within three years and in early clinically evident AD, exosome marker CD81-normalized ADE levels of complement effector components of the classical and alternative pathways including C3b and C5b-9 were higher than in matched cognitively normal controls (Goetzl et al. Ann Neurol. 2018; 83:544-552; Winston et al. Alzheimers Dement (Amst). 2019; 11:61-66). Further, ADE levels of several complement-regulatory membrane proteins were already lower than in matched cognitively normal controls 5-12 years before onset of dementia. In sports-related TBI, CD81-normalized ADE levels of complement effector components of the classical, alternative and lectin pathways were higher than in matched cognitively normal controls acutely and for months (Goetzl et al. Faseb J. 2020; 34:3359-3366). The same pattern of elevated CD81-normalized ADE levels of complement effector components was detected in TBI of military veterans and some persisted for years (Goetzl et al. Faseb J. 2020; 34:3359-3366). In TBI of both populations, the ADE levels of complement components including C3b and C5b-9 were 12- to 35-fold higher than those in neuron-derived exosomes.

Major depressive disorder (MDD) is ranked by the World Health Organization as the single largest contributor to global disability. Despite its high prevalence and morbidity, however, diagnosing MDD is very unreliable. Further, current first-line pharmacological treatments for MDD are inadequate, as only 27% of patients remit after an initial trial and only 67% after four full trials. Evaluation of new therapeutic approaches should include specific biomarkers that objectively identify involvement of pathogenic mechanisms underlying MDD and may reveal relevant molecular targets.

Thus, there is a need in the art for biomarkers and methods for detecting exosomal complement mediators, cytokines, and mitochondrial electron transport biomarkers in biological samples as well as compositions and methods useful for treating depression, psychosis and schizophrenia. Additionally, them is a need in the art for compositions for detecting biomarkers as well as compositions and methods useful for treating depression, psychosis and schizophrenia. The present disclosure meets this need by providing accurate, non-invasive methods for detecting complement mediators, cytokines, and mitochondrial electron transport biomarkers that are diagnostic for depression, psychosis, and schizophrenia. The present disclosure further provides novel methods, assays, kits, and compositions for diagnosing, prognosing, predicting, and treating depression, psychosis and schizophrenia.

This background information is provided for the purpose of making known information believed by the applicant to be of possible relevance to the present disclosure. No admission is necessarily intended, nor should be construed, that any of the preceding information constitutes prior art against the present disclosure.

SUMMARY OF THE INVENTION

The disclosure is based on the discovery of biomarkers from astrocyte-derived exosomes and neuron-derived exosomes (i.e., extracellular vesicles) that can be used to detect complement mediators, cytokines, and mitochondrial electron transport biomarkers associated with depression, psychosis and schizophrenia. These biomarkers can be used alone or in combination with one or more additional biomarkers or relevant clinical parameters in prognosis, diagnosis, or monitoring treatment of abnormalities associated with depression, psychosis and schizophrenia. The disclosure is also based on the discovery that agents that modify and/or affect the levels of exosomal complement mediators, cytokines, and mitochondrial electron transport biomarkers are useful for treating depression, psychosis and schizophrenia.

Biomarkers that can be used in the practice of the disclosure include, but are not limited to, human tetraspanning exosome marker CD81, subunit 6 of NADH-ubiquinone oxidoreductase (complex I), decay-accelerating factor (CD55), glutamine synthetase, subunit 1 of cytochrome C oxidase (complex IV), subunit 1 of NADH-ubiquinone oxidoreductase (complex I), subunit 10 of cytochrome b-c1 oxidase (complex III), glial fibrillary acidic protein, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2) and mitochondrial open-reading frame of the 12S rRNA-c (MOTS-c).

In some embodiments, the disclosure provides a method comprising: a) providing a biological sample comprising exosomes from a subject; b) enriching the sample for exosomes; and c) detecting the presence of one or more biomarkers, wherein the one or more biomarker is mitochondrial electron transport proteins, cytokines, and/or complement proteins. In some embodiments, the one or more marker is human tetraspanning exosome marker CD81, subunit 6 of NADH-ubiquinone oxidoreductase (complex I), decay-accelerating factor (CD55), glutamine synthetase, subunit 1 of cytochrome C oxidase (complex IV), subunit 1 of NADH-ubiquinone oxidoreductase (complex I), subunit 10 of cytochrome b-c1 oxidase (complex III), glial fibrillary acidic protein, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2), Peroxisome proliferator-activated receptor gamma coactivator 1-alpha (PGC-1α), Nuclear factor erythroid 2-related factor 2 (NRF2), and/or mitochondrial open-reading frame of the 12S rRNA-c (MOTS-c). In other embodiments, the exosomes am astrocyte-derived exosomes and/or neuron-derived exosomes. In still other embodiments, the biological sample is selected from the list consisting of whole blood, plasma, scrum, lymph, amniotic fluid, urine, and saliva. In some embodiments, the marker is a full-size marker or a fragment of the full-size marker. In other embodiments, the detecting the presence of the marker in the biological sample comprises detecting the amount of the marker in the biological sample. In certain embodiment, the subject has or is suspected of having depression, psychosis. In other embodiments, the subject has or is suspected of having schizophrenia. In other embodiments, the subject has or is suspected of having major depressive disorder (MDD).

In other embodiments, the disclosure provides a method comprising: a) providing a biological sample comprising exosomes from a subject having depression or psychosis; b) isolating exosomes from the biological sample; and c) detecting the presence of one or more biomarkers in the exosomes, wherein the one or mom biomarker is a mitochondrial electron transport protein, a cytokine, and/or a complement protein. In some embodiments, the isolating exosomes from the biological sample comprises: contacting the biological sample with an agent under conditions wherein the exosomes present in the biological sample bind to the agent to form an exosome-agent complex; and isolating the exosomes from the exosome-agent complex to obtain a sample containing the exosomes, wherein the purity of the exosomes present in said sample are greater than the purity of the exosomes present in said biological sample. In yet other embodiments, the exosomes are astrocyte-derived exosomes and/or neuron-derived exosomes. In some embodiments, the one or more marker is human tetraspanning exosome marker CD81, subunit 6 of NADH-ubiquinone oxidoreductase (complex I), decay-accelerating factor (CD55), glutamine synthetase, subunit 1 of cytochrome C oxidase (complex IV), subunit 1 of NADH-ubiquinone oxidoreductase (complex I), subunit 10 of cytochrome b-c1 oxidase (complex III), glial fibrillary acidic protein, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2), Peroxisome proliferator-activated receptor gamma coactivator 1-alpha (PGC-1α), Nuclear factor erythroid 2-related factor 2 (NRF2), and/or mitochondrial open-reading frame of the 12S rRNA-c (MOTS-c). In still other embodiments, the agent is an antibody. In other embodiments, the antibody is an anti-Glutamine Aspartate Transporter antibody. In certain embodiment, the biological sample is selected from the list consisting of whole blood, plasma, serum, lymph, amniotic fluid, urine, and saliva. In other embodiments, the marker is a full-size marker or a fragment of the full-size marker. In other embodiments, the detecting the presence of the marker in the biological sample comprises detecting the amount of the marker in the biological sample. In yet other embodiments, the methods of the disclosure further comprise the step of determining a treatment course of action based on the detection of the one or more biomarkers. In some embodiments, the subject has or is suspected of having psychosis. In some embodiments, the subject has or is suspected of having schizophrenia. In some embodiments, the subject has or is suspected of having depression. In some embodiments, the subject has or is suspected of having major depressive disorder (MDD).

In some embodiments, the disclosure provides methods for treating a subject, comprising the steps of: providing a biological sample from a subject having or suspected of having psychosis or depression, wherein the sample comprises exosomes; measuring the level of one or more biomarkers selected from the group consisting of a mitochondrial electron transport protein, a cytokine, and a complement protein from the biological sample, wherein an altered level of the one or more biomarkers in the sample relative to the level in a control sample is indicative of a need for treatment; and administering an effective amount of an agent to the subject thereby treating the psychosis or depression in the subject. In some embodiments, the one or more marker is human tetraspanning exosome marker CD81, subunit 6 of NADH-ubiquinone oxidoreductase (complex I), decay-accelerating factor (CD55), glutamine synthetase, subunit 1 of cytochrome C oxidase (complex IV), subunit 1 of NADH-ubiquinone oxidoreductase (complex I), subunit 10 of cytochrome b-c1 oxidase (complex III), glial fibrillary acidic protein, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2), Peroxisome proliferator-activated receptor gamma coactivator 1-alpha (PGC-1α), Nuclear factor erythroid 2-related factor 2 (NRF2), and/or mitochondrial open-reading frame of the 12S rRNA-c (MOTS-c). In other embodiments, the agent is a SOD1 mimetic, a C3 convertase inhibitor, a LIF supplement, a LIF receptor agonist, or a ROS scavenger. In yet other embodiments, the exosomes are astrocyte-derived exosomes and/or neuron-derived exosomes.

In other embodiments, the present disclosure provides a method of detecting markers in a biological sample, the method comprising: a) providing; i) a biological sample comprising exosomes from a subject and ii) immunoassay reagents for detection of one or more biomarkers selected from the group consisting of a mitochondrial electron transport protein, a cytokine, and a complement protein; b) isolating exosomes from the biological sample and c) detecting the presence of one or more biomarkers selected from the group consisting of human tetraspanning exosome marker CD81, subunit 6 of NADH-ubiquinone oxidoreductase (complex I), decay-accelerating factor (CD55), glutamine synthetase, subunit 1 of cytochrome C oxidase (complex IV), subunit 1 of NADH-ubiquinone oxidoreductase (complex I), subunit 10 of cytochrome b-c1 oxidase (complex III), glial fibrillary acidic protein, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2) and mitochondrial open-reading frame of the 12S rRNA-c (MOTS-c) in the exosomes using said reagents. In some embodiments, the subject has psychosis. In other embodiments, the subject has schizophrenia. In some embodiments, the subject has or is suspected of having depression. In some embodiments, the subject has or is suspected of having major depressive disorder (MDD).

In some embodiments, the reagents comprise antibodies for performing an immunoassay. In some embodiments, the immunoassay is selected from the group consisting of an ELISA, radio-immunoassay, automated immunoassay, cytometric bead assay, and immunoprecipitation assay. In other embodiments, the biological sample can be any bodily fluid comprising exosomes, including, but not limited to, whole blood, plasma, serum, lymph, amniotic fluid, urine, and saliva, in some embodiments, the marker is a full-size marker. In other embodiments said marker is a fragment of the full-size marker. In other embodiments, the detecting the presence of the marker in the biological sample comprises detecting the amount of the marker in the biological sample. In some embodiments, the method further comprises the step of determining a treatment course of action based on the detection of the marker or the diagnosis of psychosis or schizophrenia. In some embodiments, the method further comprises the step of determining a treatment course of action based on the detection of the marker or the diagnosis of depression or major depressive disorder (MDD).

In some embodiments, the subject has been diagnosed with psychosis and/or schizophrenia or suspected of having psychosis and/or schizophrenia. In other embodiments, the subject is at-risk of developing psychosis or schizophrenia. In other embodiments, the psychosis is acute psychosis or chronic psychosis.

In some embodiments, the subject has been diagnosed with depression or major depressive disorder (MDD) or suspected of having depression or major depressive disorder (MDD). In other embodiments, the subject is at-risk of developing depression or major depressive disorder (MDD).

In some embodiments, isolating exosomes from the biological sample comprises: contacting the biological sample with an agent under conditions wherein an exosome present in the biological sample binds to the agent to form an exosome-agent complex; and isolating the exosome from the exosome-agent complex to obtain a sample containing the exosome, wherein the purity of the exosomes present in said sample is greater than the purity of the exosomes present in said biological sample. The agent may be an antibody that specifically binds to an exosome surface marker (e.g., Glutamine Aspartate Transporter (GLAST)). In some aspects of the present embodiment, the contacting comprises incubating or reacting. Example 1 describes isolation of exosomes from a biological sample, for example, by immunoabsorption using an anti-human Glutamine Aspartate Transporter (GLAST) (ACSA-1) biotinylated antibody specific for this surface protein.

Biomarker proteins can be measured, for example, by performing immunohistochemistry, immunocytochemistry, immunofluorescence, immunoprecipitation, Western blotting, or an enzyme-linked immunosorbent assay (ELISA). In certain embodiments, the level of a biomarker is measured with an immunoassay. For example, the level of the biomarker can be measured by contacting an antibody with the biomarker, wherein the antibody specifically binds to the biomarker, or a fragment thereof containing an antigenic determinant of the biomarker. Antibodies that can be used in the practice of the disclosure include, but are not limited to, monoclonal antibodies, polyclonal antibodies, chimeric antibodies, recombinant fragments of antibodies, Fab fragments, Fab' fragments, F(ab')$_2$ fragments, F$_v$ fragments, or scF$_v$ fragments. In one embodiment, the method comprises measuring amounts of an in vitro complex comprising a labeled antibody bound to an astrocyte-derived exosome biomarker. In one aspect, the exosome biomarker is selected from the group consisting of mitochondrial electron transport protein, a cytokine, and a complement protein. In other embodiments, the biomarker is human tetraspanning exosome marker CD81, subunit 6 of NADH-ubiquinone oxidoreductase (complex I), decay-accelerating factor (CD55), glutamine synthetase, subunit 1 of cytochrome C oxidase (complex IV), subunit 1 of NADH-ubiquinone oxidoreductase (complex I), subunit 10 of cytochrome b-c1 oxidase (complex II), glial fibrillary acidic protein, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2) and mitochondrial open-reading frame of the 12S rRNA-c (MOTS-c). In some embodiments, increased levels of the biomarker human tetraspanning exosome marker CD81, subunit 6 of NADH-ubiquinone oxidoreductase (complex I), decay-accelerating factor (CD55), glutamine synthetase, subunit 1 of cytochrome C oxidase (complex IV), subunit 1 of NADH-ubiquinone oxidoreductase (complex I), subunit 10 of cytochrome b-c1 oxidase (complex III), glial fibrillary acidic protein, complement fragment C3b, TCC C5b-9, superoxide dismutase 1 (SOD1), CD59, IL-6, neuron-specific enolase, leukemia inhibitory factor (LIF), mitochondrial electron transport chain complexes I and II, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2), Peroxisome proliferator-activated receptor gamma coactivator 1-alpha (PGC-1α), Nuclear factor erythroid 2-related factor 2 (NRF2), and/or mitochondrial open-reading frame of the 12S rRNA-c (MOTS-c) compared to reference value ranges of the biomarkers for a control subject indicate that the subject has schizophrenia or is at-risk of developing schizophrenia. In some aspects, the control subject is a subject without schizophrenia. In some embodiments, decreased levels of the biomarker human tetraspanning exosome marker CD81, subunit 6 of NADH-ubiquinone oxidoreductase (complex I), decay-accelerating factor (CD55), glutamine synthetase, subunit 1 of cytochrome C oxidase (complex IV), subunit 1 of NADH-ubiquinone oxidoreductase (complex I), subunit 10 of cytochrome b-c1 oxidase (complex II), glial fibrillary acidic protein, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2), Peroxisome proliferator-activated receptor gamma coactivator 1-alpha (PGC-1α), Nuclear factor erythroid 2-related factor 2 (NRF2), and/or mitochondrial open-reading frame of the 12S rRNA-c (MOTS-c) compared to reference value ranges of the biomarkers for a control subject indicate that the subject has schizophrenia or is at-risk of developing schizophrenia. In some aspects, the control subject is a subject without schizophrenia.

The levels of the biomarkers from exosomes from a subject can be compared to reference value ranges for the biomarkers found in one or more samples of exosomes from one or more subjects without schizophrenia (e.g., control sample, healthy subject without schizophrenia). Alternatively, the levels of the biomarkers from exosomes from a subject can be compared to reference values ranges for the biomarkers found in one or more samples of exosomes from one or more subjects with schizophrenia.

In some embodiments, the disclosure provides a method for monitoring the efficacy of a therapy for treating depression, psychosis and/or schizophrenia in a patient, the method comprising: a) providing a first biological sample comprising exosomes from the patient before the patient undergoes the therapy and a second biological sample comprising exosomes after the patient undergoes the therapy; b) isolating exosomes from the first biological sample and the second biological sample; and c) detecting one or more biomarkers selected from the group consisting of a mitochondrial electron transport protein, a cytokine, and a complement protein in the exosomes from the first biological sample and the second biological sample; and d) comparing the levels of the one or more biomarkers for the exosomes from the first biological sample to the levels of the one or more biomarkers for the exosomes from the second biological sample, wherein decreased levels of the one or more biomarkers for the exosomes from the second biological sample compared to the levels of the one or more biomarkers for the exosomes from the first biological sample indicate that the patient is improving, and increased levels of the one or more biomarkers for the exosomes from the second biological sample compared to the levels of the one or more biomarkers for the exosomes from the first biological sample indicate that the patient is worsening or not responding to the therapy. In some embodiments, the one or more biomarker is human tetraspanning exosome marker CD81, subunit 6 of NADH-ubiquinone oxidoreductase (complex I), decay-accelerating factor (CD55), glutamine synthetase, subunit 1 of cytochrome C oxidase (complex IV), subunit 1 of NADH-ubiquinone oxidoreductase (complex I), subunit 10 of cytochrome b-c1 oxidase (complex II), glial fibrillary acidic protein, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2), Peroxisome proliferator-activated receptor gamma coactivator 1-alpha (PGC-1α), Nuclear factor erythroid 2-related factor 2 (NRF2), and/or mitochondrial open-reading frame of the 12S rRNA-c (MOTS-c). In some embodiments, the exosomes are neuron-derived exosomes and/or astrocyte-derived exosomes.

In some embodiments, the disclosure provides a method for monitoring the efficacy of a therapy for treating depression, psychosis and/or schizophrenia in a patient, the method comprising: a) providing a first biological sample comprising exosomes from the patient before the patient undergoes the therapy and a second biological sample comprising exosomes after the patient undergoes the therapy; b) isolating exosomes from the first biological sample and the second biological sample; and c) detecting one or more biomarkers selected from the group consisting of mitochondrial electron transport protein, a cytokine, and a complement protein from the exosomes from the first biological sample and the second biological sample; and d) comparing the levels of the one or more biomarkers for the exosomes from the first biological sample to the levels of the one or more biomarkers for the exosomes from the second biological sample, wherein increased levels of the one or more biomarkers for the exosomes from the second biological sample compared to the levels of the one or more biomarkers for the exosomes from the first biological sample indicate that the patient is improving, and decreased levels of the one or more biomarkers for the exosomes from the second biological sample compared to the levels of the one or more biomarkers for the exosomes from the first biological sample indicate that the patient is worsening or not responding to the therapy. In some embodiments, the one or more biomarkers are human tetraspanning exosome marker CD81, subunit 6 of NADH-ubiquinone oxidoreductase (complex I), decay-accelerating factor (CD55), glutamine synthetase, subunit 1 of cytochrome C oxidase (complex IV), subunit 1 of NADH-ubiquinone oxidoreductase (complex I), subunit 10 of cytochrome b-c1 oxidase (complex III), glial fibrillary acidic protein, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2), Peroxisome proliferator-activated receptor gamma coactivator 1-alpha (PGC-1α), Nuclear factor erythroid 2-related factor 2 (NRF2), and/or mitochondrial open-reading frame of the 12S rRNA-c (MOTS-c).

In other embodiments, the disclosure provides a method for monitoring depression, psychosis and/or schizophrenia in a subject, the method comprising: a) measuring levels of one or more biomarkers selected from the group consisting of a mitochondrial electron transport protein, a cytokine, and a complement protein from exosomes from a first biological sample from the subject, wherein the first biological sample is obtained from the subject at a first time point; b) measuring levels of one or more biomarkers selected from the group consisting of a mitochondrial electron transport protein, a cytokine, and a complement protein from exosomes from a second biological sample from the subject, wherein the second biological sample is obtained from the subject at a second (i.e., later) time point; and c) comparing the levels of the biomarkers for exosomes from the first biological sample to the levels of the biomarkers for exosomes from the second biological sample, wherein decreased levels of the one or more biomarkers selected from the group consisting of a mitochondrial electron transport protein, a cytokine, and a complement protein from the exosomes from the second biological sample compared to the levels of the biomarkers in the first biological sample indicate that the patient is improving, and increased levels of the one or more biomarkers selected from the group consisting of a mitochondrial electron transport protein, a cytokine, and a complement protein from the exosomes from the second biological sample compared to the levels of the biomarkers for the exosomes from the first biological sample indicate that the patient is worsening. In some embodiments, the one or more biomarkers are selected from the group consisting of human tetraspanning exosome marker CD81, subunit 6 of NADH-ubiquinone oxidoreductase (complex I), decay-accelerating factor (CD55), glutamine synthetase, subunit 1 of cytochrome C oxidase (complex IV), subunit 1 of NADH-ubiquinone oxidoreductase (complex I), subunit 10 of cytochrome b-c1 oxidase (complex III), glial fibrillary acidic protein, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2) and mitochondrial open-reading frame of the 12S rRNA-c (MOTS-c).

In other embodiments, the disclosure provides a method for monitoring depression, acute psychosis and/or schizophrenia in a subject, the method comprising: a) measuring levels of one or more biomarkers selected from the group consisting of a mitochondrial electron transport protein, a cytokine, and a complement protein from exosomes from a first biological sample from the subject, wherein the first biological sample is obtained from the subject at a first time point; b) measuring levels of one or more biomarkers selected from the group consisting of a mitochondrial electron transport protein, a cytokine, and a complement protein from exosomes from a second biological sample from the subject, wherein the second biological sample is obtained from the subject at a second (i.e., later) time point; and c) comparing the levels of the biomarkers in the exosomes from the first biological sample to the levels of the biomarkers in the exosomes from the second biological sample, wherein increased levels of the one or more biomarkers selected from the group consisting of a mitochondrial electron transport protein, a cytokine, and a complement protein from the exosomes from the second biological sample compared to the levels of the biomarkers in the first biological sample indicate that the patient is improving, and decreased levels of the one or more biomarkers from the exosomes from the second biological sample compared to the levels of the biomarkers for the astrocyte-derived exosomes from the first biological sample indicate that the patient is worsening. In one embodiment, the exosomes are neuron-derived exosomes and/or astrocyte-derived exosomes.

In yet other embodiments, the disclosure provides a method of treating a patient suspected of having depression, acute psychosis and/or schizophrenia, the method comprising: a) detecting exosomal biomarker levels in the patient or receiving information regarding the exosomal biomarker levels of the patient, as determined according to a method described herein; and b) administering a therapeutically effective amount of at least one agent that alters exosomal biomarker levels in the subject. After treatment, the method may further comprise monitoring the response of the patient to treatment. In some embodiments, the agent is a SOD1 mimetic, a C3 convertase inhibitor, a LIF supplement, a LIF receptor agonist, or a ROS scavenger. In other embodiments, the exosomes are astrocyte-derived exosomes and/or neuron-derived exosomes. In some embodiments, the exosomal biomarker is a mitochondrial electron transport protein, a cytokine, and/or a complement protein.

In other embodiments, the disclosure provides a method comprising: providing a biological sample from a subject suspected of having depression, acute psychosis and/or schizophrenia; detecting the presence or level of at least one or more biomarkers selected from the group consisting of a mitochondrial electron transport protein, a cytokine, and a complement protein; and administering a treatment to the subject. In one embodiment, the method further comprises administering a therapeutically effective amount of at least one agent that treats depression, acute psychosis and/or schizophrenia to the subject if increased levels of the one or more biomarkers are detected in the subject. In one embodiment, the method further comprises administering a therapeutically effective amount of at least one agent that treats depression, acute psychosis and/or schizophrenia to the subject if decreased levels of the one or more biomarkers are detected in the subject. After treatment, the method may further comprise monitoring the response of the subject to treatment. In some embodiments, the one or more biomarkers comprises human tetraspanning exosome marker CD81, subunit 6 of NADH-ubiquinone oxidoreductase (complex I), decay-accelerating factor (CD55), glutamine synthetase, subunit 1 of cytochrome C oxidase (complex IV), subunit 1 of NADH-ubiquinone oxidoreductase (complex I), subunit 10 of cytochrome b-c1 oxidase (complex III), glial fibrillary acidic protein, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2), Peroxisome proliferator-activated receptor gamma coactivator 1-alpha (PGC-1α), Nuclear factor erythroid 2-related factor 2 (NRF2), and/or mitochondrial open-reading frame of the 12S rRNA-c (MOTS-c).

In other embodiments, the present disclosure provides a method of treating a subject with depression, acute psychosis and/or schizophrenia, comprising: providing a biological sample from the subject; determining the level of at least one or more biomarkers selected from the list consisting of a mitochondrial electron transport protein, a cytokine, and a complement protein using at least one reagent that specifically binds to said biomarkers; and prescribing a treatment regimen based on the level of the one or more biomarkers. In some embodiments, the method further comprises isolating exosomes from the biological sample. In some embodiments, the biomarker comprises human tetraspanning exosome marker CD81, subunit 6 of NADH-ubiquinone oxidoreductase (complex I), decay-accelerating factor (CD55), glutamine synthetase, subunit 1 of cytochrome C oxidase (complex IV), subunit 1 of NADH-ubiquinone oxidoreductase (complex I), subunit 10 of cytochrome b-c1 oxidase (complex III), glial fibrillary acidic protein, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2), Peroxisome proliferator-activated receptor gamma coactivator 1-alpha (PGC-1α), Nuclear factor erythroid 2-related factor 2 (NRF2), and/or mitochondrial open-reading frame of the 12S rRNA-c (MOTS-c).

In some embodiments, the disclosure provides a set of biomarkers for assessing depression, acute psychosis and/or schizophrenia status of a subject, the set comprising one or more biomarkers selected from the group consisting of a mitochondrial electron transport protein, a cytokine, and a complement protein, wherein exosome levels of the biomarkers in the set are assayed; and wherein the biomarker levels of the set of biomarkers determine the depression, acute psychosis and/or schizophrenia status of the subject with at least 40%, 50%, 60%, 70%, 75%, 80% 85%, 90%, 95%, 99%, or 100% specificity. In some aspects, the set of biomarkers determine the depression, acute psychosis and/or schizophrenia status of the subject with at least 40%, 50%, 60%, 70%, 75%, 80%, 85%, 90%, 95%, 99%, or 100% sensitivity. In yet other aspects, the set of biomarkers determine the depression, acute psychosis and/or schizophrenia status of the subject with at least 40%, 50%, 60%, 70%, 75%, 80%, 85%, 90%, 95%, 99%, or 100% accuracy. In some embodiments the biomarker comprises human tetraspanning exosome marker CD81, subunit 6 of NADH-ubiquinone oxidoreductase (complex I), decay-accelerating factor (CD55), glutamine synthetase, subunit 1 of cytochrome C oxidase (complex IV), subunit 1 of NADH-ubiquinone oxidoreductase (complex I), subunit 10 of cytochrome b-c1 oxidase (complex III), glial fibrillary acidic protein, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2), Peroxisome proliferator-activated receptor gamma coactivator 1-alpha (PGC-1α), Nuclear factor erythroid 2-related factor 2 (NRF2), and/or mitochondrial open-reading frame of the 12S rRNA-c (MOTS-c).

In other embodiments, the disclosure provides a composition comprising at least one in vitro complex comprising a labeled antibody bound to a biomarker protein selected from the group consisting of a mitochondrial electron transport protein, a cytokine, and a complement protein, wherein said biomarker protein is extracted from exosomes of a subject who has been diagnosed with depression, acute psychosis and/or schizophrenia, suspected of having depression, acute psychosis and/or schizophrenia, or at risk of developing depression, acute psychosis and/or schizophrenia. The antibody may be detectably labeled with any type of label, including, but not limited to, a fluorescent label, an enzyme label, a chemiluminescent label, or an isotopic label. In some embodiments, the composition is in a detection device (i.e., device capable of detecting labeled antibody). In some embodiments, the one or more biomarkers comprise tetraspanning exosome marker CD81, subunit 6 of NADH-ubiquinone oxidoreductase (complex I), decay-accelerating factor (CD55), glutamine synthetase, subunit 1 of cytochrome C oxidase (complex IV), subunit 1 of NADH-ubiquinone oxidoreductase (complex I), subunit 10 of cytochrome b-c1 oxidase (complex III), glial fibrillary acidic protein, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2), Peroxisome proliferator-activated receptor gamma coactivator 1-alpha (PGC-1α), Nuclear factor erythroid 2-related factor 2 (NRF2), and/or mitochondrial open-reading frame of the 12S rRNA-c (MOTS-c).

In other embodiments, the disclosure provides a kit for detecting or monitoring depression, acute psychosis and/or schizophrenia in a subject. In some embodiments, the kit may include a container for holding a biological sample isolated from a subject who has been diagnosed or suspected of having depression, acute psychosis and/or schizophrenia or at risk of developing depression, acute psychosis and/or schizophrenia, at least one agent that specifically detects a biomarker of the present disclosure; and printed instructions for reacting the agent with exosomes from the biological sample or a portion of the biological sample to detect the presence or amount of at least one biomarker. In other embodiments, the kit may also comprise one or more agents that specifically bind exosomes for use in isolating exosomes from a biological sample. In yet other embodiments, the kit may further comprise one or more control reference samples and reagents for performing an immunoassay. In certain embodiments, the agents may be packaged in separate containers. In some embodiments, the kit comprises agents for measuring the levels of a mitochondrial electron transport protein, a cytokine, and/or a complement protein.

In yet other embodiments, the kit further comprises an antibody that binds to an exosome surface marker (e.g., Glutamine Aspartate Transporter (GLAST)). In some embodiments, the exosomes are neuron-derived exosomes and/or astrocyte-derived exosomes.

In other embodiments, the disclosure provides a method for treating depression, acute psychosis and/or schizophrenia, the method comprising the steps of: providing a biological sample from a subject suspected of having depression, acute psychosis and/or schizophrenia, wherein the sample comprises exosomes; measuring the level of one or more biomarkers selected from the group consisting of a mitochondrial electron transport protein, a cytokine, and a complement protein from the biological sample, wherein an altered level of the one or more biomarkers in the sample relative to the level in a control sample is indicative of a need for treatment; and administering an effective amount of an agent to the subject thereby treating the depression, acute psychosis and/or schizophrenia in the subject. In some embodiments, the one or more marker is human tetraspanning exosome marker CD81, subunit 6 of NADH-ubiquinone oxidoreductase (complex I), decay-accelerating factor (CD55), glutamine synthetase, subunit 1 of cytochrome C oxidase (complex IV), subunit 1 of NADH-ubiquinone oxidoreductase (complex I), subunit 10 of cytochrome b-c1 oxidase (complex III), glial fibrillary acidic protein, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2), Peroxisome proliferator-activated receptor gamma coactivator 1-alpha (PGC-1α), Nuclear factor erythroid 2-related factor 2 (NRF2), and/or mitochondrial open-reading frame of the 12S rRNA-c (MOTS-c). In other embodiments, the agent is a SOD1 mimetic, a C3 convertase inhibitor, a LIF supplement, a LIP receptor agonist, or a ROS scavenger. In yet other embodiments, the exosomes are astrocyte-derived exosomes and/or neuron-derived exosomes.

These and other embodiments of the present disclosure will readily occur to those of skill in the art in light of the disclosure herein, and all such embodiments are specifically contemplated.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

Figure 1A:
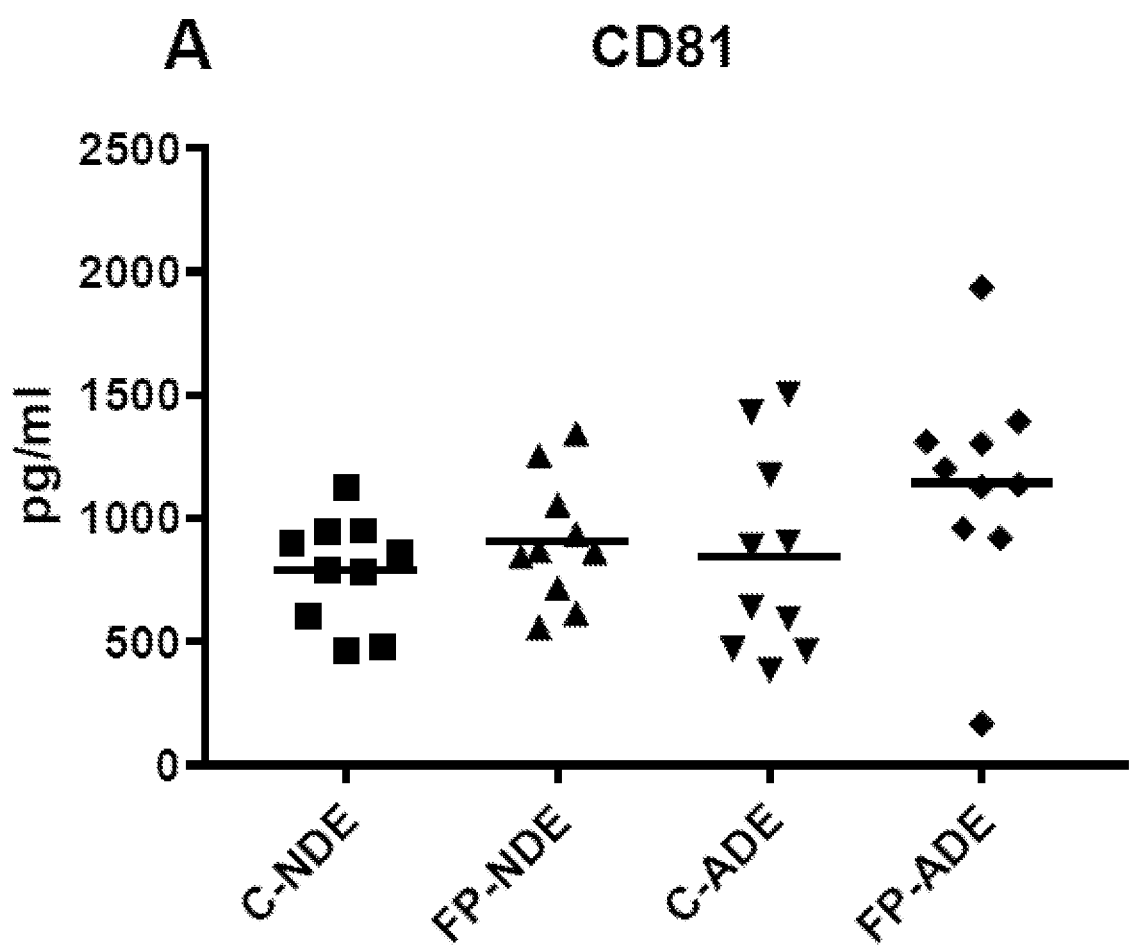
FIGS. 1A-1F set forth data showing protein constituents of the mitochondrial oxidative phosphorylation system in NDEs and ADEs. Each point represents the value for one study participant. The mean±S.E.M. of control (C) and first-episode psychosis (FP) groups, respectively, were 792±682 pg/ml and 907±80.4 pg/ml for NDEs and 846±129 pg/ml and 1146±141 pg/ml for ADEs for CD81 (A), 1437±223 pg/ml and 912±89.2 pg/ml for NDEs and 2010±326 pg/ml and 1195±161 pg/ml for ADEs for NDI subunit of NADH-ubiquinone oxidoreductase (complex I) (B), 1574±246 pg/ml and 542±62.1 pg/ml for NDEs and 2363±458 pg/ml and 825±166 pg/ml for ADEs for ND6 subunit of NADH-ubiquinone oxidoreductase (complex I) (C), 1404±112 pg/ml and 635±53.8 pg/ml for NDEs and 1916±315 pg/ml and 236±47.2 pg/ml for ADEs for subunit 10 of cytochrome b-c1 (complex III) (D), 10975±1461 pg/ml and 9750±2011 pg/ml for NDEs and 14080±2348 pg/ml and 9080±1948 pg/ml for ADEs for subunit 1 of cytochrome c oxidase (complex IV) (E), and 2403±672 pg/ml and 1829±315 pg/ml for NDEs and 5472±724 pg/ml and 4219±723 pg/ml for ADEs for superoxide dismutase 1 (SOD1) (F). All values in B-F and in FIG. 2 were normalized for content of the exosome marker CD81. Statistical significance of differences in values between C and FP groups for NDEs and ADEs were calculated by two sample t tests; †, $p<0.05$; *, $p<0.01$; **, $p<0.001$.

Each of the limitations of the disclosure can encompass various embodiments of the disclosure. It is, therefore, anticipated that each of the limitations of the disclosure involving any one element or combinations of elements can be included in each aspect of the disclosure. This disclosure is not limited in its application to the details of construction and the arrangement of components set forth in the following description. The disclosure is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items. It must be noted that as used herein and in the appended claims, the singular forms "a," "an," and "the" include plural references unless context clearly dictates otherwise. Thus, for example, a reference to "a fragment" includes a plurality of such fragments, a reference to an "antibody" is a reference to one or more antibodies and to equivalents thereof known to those skilled in the art, and so forth.

DESCRIPTION OF THE INVENTION

It is to be understood that the disclosure is not limited to the particular methodologies, protocols, cell lines, assays, and reagents described herein, as these may vary. It is also to be understood that the terminology used herein is intended to describe particular embodiments of the present disclosure, and is in no way intended to limit the scope of the present disclosure as set forth in the appended claims.

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present disclosure, the preferred methods, devices, and materials are now described. All publications cited herein are incorporated herein by reference in their entirety for the purpose of describing and disclosing the methodologies, reagents, and tools reported in the publications that might be used in connection with the disclosure. Nothing herein is to be construed as an admission that the disclosure is not entitled to antedate such disclosure by virtue of prior disclosure.

The practice of the present disclosure will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Colowick, S. et al., eds., Methods In Enzymology, Academic Press, Inc.; Handbook of Experimental Immunology, Vols. I-IV (D. M.

Weir and C. C. Blackwell, eds., 1986, Blackwell Scientific Publications); Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press); PCR (Introduction to Biotechniques Series), 2nd ed. (Newton & Graham eds., 1997, Springer Verlag).

The present disclosure relates, in part, to the discovery that exosomal biomarkers can be used to detect pathogenesis of depression, acute psychosis and schizophrenia. The inventor has demonstrated that diverse abnormalities in depression, acute psychosis patients, including elevated astrocyte-derived exosome levels of neurotoxic complement proteins as well as dysfunctional neuron-derived exosome and astrocyte-derived exosome levels of electron transport system proteins (see, e.g., Example 1).

The present disclosure also provides agents for use in the methods described herein. Such agents may include small molecule compounds; peptides and proteins including antibodies or functionally active fragments thereof.

The present disclosure further provides kits for identifying a subject at risk of depression, acute psychosis and/or schizophrenia or prescribing a therapeutic regimen or predicting benefit from therapy in a subject having depression, acute psychosis and/or schizophrenia or at risk of developing depression, acute psychosis and/or schizophrenia. In these embodiments, the kits comprise one or more antibodies which specifically bind exosomes, one or more antibodies which specifically bind an exosomal biomarker of the disclosure, one or more containers for collecting and or holding the biological sample, and instructions for the kits use.

The present disclosure further provides methods for treating depression, acute psychosis and/or schizophrenia in a subject. In these embodiments, the disclosure provides methods for treating depression, acute psychosis and/or schizophrenia in a subject comprising administering an effective amount of an agent to the subject, thereby treating the depression, acute psychosis and/or schizophrenia in the subject. In some embodiments, the disclosure provides methods of treating depression, acute psychosis and/or schizophrenia in a subject, comprising administering an effective amount of a SOD1 mimetic, a C3 convertase inhibitor, a LIF supplement, a LIF receptor agonist, and/or a ROS scavenger to a subject having or suspected of having depression, acute psychosis and/or schizophrenia, thereby treating the depression, acute psychosis and/or schizophrenia.

The section headings are used herein for organizational purposes only, and are not to be construed as in any way limiting the subject matter described herein.

Complement System

The complement system provides an early acting mechanism to initiate and amplify the inflammatory response to microbial infection and other acute insults. While complement activation provides a valuable first-line defense against potential pathogens, the activities of complement that promote a protective inflammatory response can also represent a potential threat to the host. For example, C3 and C5 proteolytic products recruit and activate neutrophils. These activated cells are indiscriminate in their release of destructive enzymes and may cause organ damage. In addition, complement activation may directly cause the deposition of lytic complement components, such as C5b-C9 TCC, on nearby host cells as well as on microbial targets, resulting in host cell lysis. Some products of complement activation, such as C3b, bind to neurons as well as microbes and thereby cause attachment of neuron-destructive CNS cells, such as microglia.

Complement can be activated through either of two distinct enzymatic cascades, referred to as the classical and alternative pathways. The classical pathway is usually triggered by antibody bound to a foreign particle and thus requires prior exposure to that particle for the generation of specific antibody. There are four plasma proteins specifically involved in the classical pathway: C1, C2, C4 and C3. The interaction of C1 with the Fc regions of IgG or IgM in immune complexes activates a C1 protease that can cleave plasma protein C4, resulting in the C4a and C4b fragments. C4b can bind another plasma protein, C2. The resulting species, C4b2, is cleaved by the C1 protease to form the classical pathway C3 convertase, C4b2a. Addition of the C3 cleavage product, C3b, to C3 convertase leads to the formation of the classical pathway C5 convertase, C4b2a3b.

In contrast to the classical pathway, the alternative pathway is spontaneously triggered by foreign or other abnormal surfaces (bacteria, yeast, virally infected cells, or damaged tissue) and is therefore capable of an immediate response to an invading organism. Them are four plasma proteins directly involved in the alternative pathway: C3, factors B and D, and properdin (also called factor P). The initial interaction that triggers the alternative pathway is not completely understood. However, it is thought that spontaneously activated C3 (C3b) binds factor B, which is then cleaved by factor D to form the complex C3bBb that possesses C3 convertase activity. The resulting convertase proteolytically modifies additional C3, producing the C3b fragment, which can covalently attach to the target and then interact with factors B and D and form the alternative pathway C3 convertase, C3bBb. The alternative pathway C3 convertase is stabilized by the binding of properdin. However, properdin binding is not required to form a functioning alternative pathway C3 convertase. Since the substrate for the alternative pathway C3 convertase is C3, C3 is therefore both a component and a product of the reaction. As the C3 convertase generates increasing amounts of C3b, an amplification loop is established. In as much as the classical pathway also may generate C3b that can bind factor B, both pathways may amplify activation of the alternative pathway. This allows more C3b to deposit on a target. For example, as described above, the binding of antibody to antigen initiates the classical pathway. If antibodies latch on to bacteria, the classical pathway generates C3b, which couples to target pathogens. However, it has been suggested that from 10% to 90% of the subsequent C3b deposited may come from the alternative pathway. The actual contribution of the alternative pathway to the formation of additional C3b subsequent to classical pathway initiation has not been clearly quantified and thus remains unknown. Addition of C3b to the C3 convertase leads to the formation of the alternative pathway C5 convertase, C3bBbC3b.

Both the classical and alternative pathways involve C3b and converge at C5, which is cleaved to form products with multiple proinflammatory effects. The converged pathway has been referred to as the terminal complement pathway. C5a is the most potent anaphylatoxin, inducing alterations in smooth muscle and vascular tone, as well as vascular permeability. It is also a powerful chemotaxin and activator of both neutrophils and monocytes. C5a-mediated cellular activation can significantly amplify inflammatory responses by inducing the release of multiple additional inflammatory mediators, including cytokines, hydrolytic enzymes, arachidonic acid metabolites and reactive oxygen species. C5 cleavage leads to the formation of C5b-9, also known as the membrane terminal attack complex (MAC or TCC). There is now strong evidence that MAC may play an important role in inflammation in addition to its role as a lytic pore-forming complex. The disclosure provides methods for detecting exosomal levels of complement system proteins. The administration of one or more neutralizing monoclonal antibodies to effector complement components or their receptors, decoy complement receptors or receptor antagonists, and esterase inhibitors of complement mediator generation may suppress ongoing complement-mediated neuronal injury and be useful for treating depression, acute psychosis and/or schizophrenia. In some embodiments, the methods of the present disclosure are used to treat depression, acute psychosis and/or schizophrenia in a subject. In other embodiments, the present disclosure provides a method for treating a subject having depression, acute psychosis and/or schizophrenia, comprising the steps of: providing a biological sample from a subject having or suspected of having depression, acute psychosis and/or schizophrenia, wherein the sample comprises exosomes; measuring the level of one or more biomarkers selected from the group consisting of a mitochondrial electron transport protein and a complement protein from the biological sample, wherein an altered level of the one or more biomarkers in the sample relative to the level in a control sample is indicative of a need for treatment; and administering an effective amount of an agent to the subject thereby treating the depression, acute psychosis and/or schizophrenia in the subject. In certain embodiments, the exosomes are astrocyte-derived exosomes and/or neuron-derived exosomes.

Many regulatory proteins exist to prevent excessive complement activation and to protect our cells and tissues from damage. The complement system distinguishes self from non-self via a range of specialized cell-surface and soluble proteins. These proteins belong to a family called the regulators of complement activation (RCA) or complement control proteins (CCP). Complement control proteins (or complement regulatory proteins) work in concert to maintain activation of the complement system at a level optimal for host defenses against microbes without damaging host tissues. Many of the complement control proteins act on the convertases, C3b.Bb and C4b.2a, which are bimolecular complexes formed early on in the complement cascade, but CD59 blocks formation of C5b-C9 TCC.

Every cell in the human body is protected by one or more of the membrane-associated RCA proteins, CR1, DAF or MCP. Factor H and C4BP circulate in the plasma and are recruited to self-surfaces through binding to host-specific polysaccharides such as the glycosaminoglycans. Most act to disrupt the formation of the convertases or to shorten the life-span of any complexes that do manage to form. Their presence on self-surfaces, and their absence from the surfaces of foreign particles, means that these regulators perform the important task of targeting complement to where it is needed—on the invading bacterium for example—while preventing activation on host tissues. For example, C3b.Bb is an important convertase that is part of the alternative pathway, and it is formed when factor B binds C3b and is subsequently cleaved. To prevent this from happening, factor H competes with factor B to bind C3b; if it manages to bind, then the convertase is not formed. Factor H can bind C3b much more easily in the presence of sialic acid, which is a component of most cells in the human body; conversely, in the absence of sialic acid, factor B can bind C3b more easily. This means that if C3b is bound to a "self" cell, the presence of sialic acid and the binding of factor H will prevent the complement cascade from activating; if C3b is bound to a bacterium, factor B will bind and the cascade will be set off as normal.

The present disclosure provides methods for detecting exosomal levels of complement regulatory proteins. The administration of one or more recombinant complement control proteins early in depression, psychosis and/or schizophrenia, guided by their levels in exosomes of subjects, could limit recruitment of complement mechanisms preventatively. In some embodiments, the methods of the present disclosure are used to treat depression, psychosis and/or schizophrenia in a subject. In other embodiments, the present disclosure provides a method for treating a subject having depression, psychosis and/or schizophrenia, comprising the steps of providing a biological sample from a subject suspected of having depression, psychosis and/or schizophrenia, wherein the sample comprises exosomes; measuring the level of one or more biomarkers selected from the group consisting of a mitochondrial electron transport protein and a complement protein in the sample from the biological sample, wherein an altered level of the one or more biomarkers in the sample relative to the level in a control sample is indicative of a need for treatment; and administering an effective amount of a SOD1 mimetic, a C3 convertase inhibitor, a LIF supplement, a LIF receptor agonist, and/or a ROS scavenger to the subject thereby treating the depression, psychosis and/or schizophrenia in the subject. In certain embodiments, exosomes are astrocyte-derived exosomes and/or neuron-derived exosomes.

Mitochondrial Electron Transport System

The mitochondrial electron transport chain (ETC) includes complexes I-IV, as well as the electron transporters ubiquinone and cytochrome c. There are two electron transport pathways in the ETC: Complex I/II/IV, with NADH as the substrate and complex II/III/V, with succinic acid as the substrate. The electron flow is coupled with the generation of a proton gradient across the inner membrane and the energy accumulated in the proton gradient is used by complex V (ATP synthase) to produce ATP. As shown in Example 2 below, exosomal levels of leukemia inhibitory factor (LIF), mitochondrial electron transport chain complexes I and II, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2) and mitochondrial open-reading frame of the 12S rRNA-c (MOTS-c) are abnormal in subjects with depression, psychosis and/or schizophrenia.

As shown in Example 1 below, exosomal levels of subunit 1 of NADH-ubiquinone oxidoreductase (complex I) were decreased in psychotic patients compared to matched controls, whereas those of the more catalytically important subunit 6 of NADH-ubiquinone oxidoreductase were significantly lower in acute psychotic patients compared to controls (See FIGS. 1B and 1C). Exosomal levels of cytochrome b-c1 oxidase (coenzyme Q-cytochrome C oxidoreductase) (complex III) also were significantly lower in FP patients than controls (FIG. 1D). This pattern of depressed levels of early mitochondrial electron transport complexes in the presence of a normal level of the terminal complex IV has been associated with increased generation of reactive oxygen species.

The present disclosure provides methods for detecting exosomal levels of mitochondrial electron transport proteins. In some embodiments, the methods of the present disclosure are used to treat psychosis and/or schizophrenia in a subject. In other embodiments, the present disclosure provides a method for treating a subject having psychosis and/or schizophrenia, comprising the steps of: providing a biological sample from a subject suspected of having psychosis and/or schizophrenia, wherein the sample comprises exosomes; measuring the level of one or more mitochondrial electron transport proteins in the sample from the biological sample, wherein an altered level of the one or more proteins in the sample relative to the level in a control sample is indicative of a need for treatment; and administering an effective amount of a SOD1 mimetic, a C3 convertase inhibitor, a LIF supplement, a LIF receptor agonist, and/or a ROS scavenger to the subject thereby treating the psychosis and/or schizophrenia in the subject. In certain embodiments, the exosomes are astrocyte-derived exosomes and/or neuron-derived exosomes.

Biological Sample

The present disclosure provides biomarkers and diagnostic and prognostic methods for depression, psychosis and/or schizophrenia. Biomarkers are detected from exosomes (e.g., astrocyte-derived exosomes) from a biological sample obtained from a subject. Biological samples can include any bodily fluid comprising exosomes, including, but not limited to, whole blood, plasma, serum, lymph, amniotic fluid, and saliva.

In some embodiments, the biological sample of the disclosure can be obtained from blood. In some embodiments, about 1-10 mL of blood is drawn from a subject. In other embodiments, about 10-50 mL of blood is drawn from a subject. Blood can be drawn from any suitable area of the body, including an arm, a leg, or blood accessible through a central venous catheter. In some embodiments, blood is collected following a treatment or activity. For example, blood can be collected following a medical exam. The timing of collection can also be coordinated to increase the number and/or composition of exosomes present in the sample. For example, blood can be collected following exercise or a treatment that induces vascular dilation.

Blood may be combined with various components following collection to preserve or prepare samples for subsequent techniques. For example, in some embodiments, blood is treated with an anticoagulant, a cell fixative, a protease inhibitor, a phosphatase inhibitor, or preservative(s) for protein or DNA or RNA following collection. In some embodiments, blood is collected via venipuncture using a needle and a syringe that is emptied into collection tubes containing an anticoagulant such as EDTA, heparin, or acid citrate dextrose (ACD). Blood can also be collected using a heparin-coated syringe and hypodermic needle. Blood can also be combined with components that will be useful for cell culture. For example, in some embodiments, blood is combined with cell culture media or supplemented cell culture media (e.g., cytokines). In certain embodiments, platelet-rich plasma (PRP) is mixed with PBS to block ex vivo platelet activation before centrifugation to yield platelet-poor plasma (PPP).

Enrichment and/or Isolation of Neuron-Derived Exosomes and Astrocyte-Derived Exosomes Samples can be enriched for neuron-derived exosomes and/or astrocyte-derived exosomes through positive selection, negative selection, or a combination of positive and negative selection. In some embodiments, exosomes are directly captured. In other embodiments, blood cells are captured and exosomes are collected from the remaining biological sample.

Samples can also be enriched for exosomes based on the biochemical properties of exosomes. The first step is physical isolation entailing polymer precipitation with centrifugation in one or two cycles. Then, for example, samples can be enriched for exosomes based on differences in antigens. In some of the embodiments, antibody-conjugated magnetic or paramagnetic beads in magnetic field gradients or fluorescently labeled antibodies with flow cytometry am used. In some of the embodiments based on metabolic differences, dye uptake/exclusion measured by flow cytometry or another sorting technology is used. Samples can also be enriched for exosomes based on other biochemical properties known in the art. For example, samples can be enriched for exosomes using ligands or soluble receptors.

In some embodiments, surface markers are used to positively enrich exosomes in the sample. In other embodiments, cell surface markers that are not found on exosomes are used to negatively enrich exosomes by depleting cell populations. Modified versions of flow cytometry sorting may also be used to further enrich for exosomes using surface markers or intracellular or extracellular markers conjugated to fluorescent labels. Intracellular and extracellular markers may include nuclear stains or antibodies against intracellular or extracellular proteins preferentially expressed in exosomes. Cell surface markers may include cell surface antigens that are preferentially expressed on astrocyte-derived exosomes and/or neuron-derived exosomes. In some embodiments, the cell surface marker is an astrocyte-derived exosome surface marker, including, for example, Glutamine Aspartate Transporter (GLAST). In other embodiments, the exosome cell-surface marker is CD171 (L1CAM neural adhesion protein). In some embodiments, a monoclonal antibody that specifically binds to GLAST (e.g., ACSA-1, mouse anti-human GLAST antibody) is used to enrich or isolate astrocyte-derived exosomes from the sample. In certain aspects, the antibody against GLAST is biotinylated. In this embodiment, the biotinylated antibody can form an antibody-exosome complex that can be subsequently isolated using streptavidin-agarose resin or beads. In other embodiments, the antibody is a monoclonal anti-human GLAST antibody (e.g., ACSA-1).

In other embodiments, exosomes are isolated or enriched from a biological sample comprising: contacting a biological sample with an agent under conditions wherein an exosome present in said biological sample binds to said agent to form an exosome-agent complex; and isolating said exosome from said exosome-agent complex to obtain a sample containing said exosome, wherein the purity of the exosomes present in the sample is greater than the purity of exosomes present in the biological sample. In certain embodiments, the contacting is incubating or reacting. In certain embodiments, the exosomes are astrocyte-derived exosomes and/or neuron-derived exosomes. In certain embodiments, the agent is an antibody or a lectin. Lectins useful for forming an exosome-lectin complex are described in U.S. Patent Application Publication No. 2012/0077263. In some embodiments, multiple isolating or enriching steps are performed. In certain aspects of the present embodiment, a first isolating step is performed to isolate exosomes from a blood sample freed of plasma membrane-derived membrane vesicles and a second isolating step is performed to isolate exosomes from other exosomes. In other embodiments, the exosome portion of the exosome-agent complex is lysed using a lysis reagent and the protein levels of the lysed exosome are assayed. In some embodiments, the antibody-exosome complex is created on a solid phase. In yet other embodiments, the methods further comprise releasing the exosome from the antibody-exosome complex. In certain embodiments, the solid phase is non-magnetic beads, magnetic beads, agarose, or sepharose. In other embodiments, the vesicle is released by exposing the antibody-exosome complex to low pH between 3.5 and 1.5. In yet other embodiments, the released exosome is neutralized by adding a high pH solution. In other embodiments, the released exosomes are lysed by incubating the released exosomes with a lysis solution. In still other embodiments, the lysis solution contains inhibitors for proteases and phosphatases.

Psychosis and Schizophrenia

Psychotic disorders are severe mental disorders that cause abnormal thinking and perceptions. People with psychoses lose touch with reality. Two of the main symptoms are delusions and hallucinations. Delusions are false beliefs, such as thinking that someone is plotting against you or that the TV is sending you secret messages. Hallucinations are false perceptions, such as hearing, seeing, or feeling something that is not them.

Schizophrenia is one type of psychotic disorder. People with bipolar disorder may also have psychotic symptoms. Other problems that can cause psychosis include alcohol and some drugs, brain tumors, brain infections, and stroke. Schizophrenia is a serious mental disorder in which people interpret reality abnormally. Schizophrenia may result in some combination of hallucinations, delusions, and extremely disordered thinking and behavior that impairs daily functioning, and can be disabling. Schizophrenia involves a range of problems with thinking (cognition), behavior and emotions. Signs and symptoms may vary, but usually involve delusions, hallucinations or disorganized speech, and reflect an impaired ability to function.

The disclosure provides methods for diagnosing psychosis and/or schizophrenia in a subject and/or identifying a subject at risk of developing psychosis and/or schizophrenia, or prescribing a therapeutic regimen or predicting benefit from therapy. Diverse abnormalities were observed in exosomal biomarkers from biological samples obtained from psychotic subjects, including elevated ADE levels of neurotoxic complement proteins as well as dysfunctional NDE and ADE levels of electron transport system proteins (see, e.g., Example 1). Levels of subunits 1 and 6 of NADH-ubiquinone oxidoreductase (complex I) and subunit 10 of cytochrome b-c1 oxidase (complex III), but not of subunit 1 of cytochrome C oxidase (complex IV) or superoxide dismutase 1 (SOD1) were significantly lower in ADEs and NDEs of psychotic subjects relative to control subjects. This dysregulated pattern of electron transport proteins was associated with increased generation of reactive oxygen species. ADE glial fibrillary acidic protein levels were significantly higher in samples from psychotic subjects relative to matched controls, indicating a higher percentage of inflammatory astrocytes in psychotic subjects (See Example 1). ADE levels of C3b opsonin were significantly higher and those of C5b-9 attack complex was marginally higher in psychotic subjects relative to matched controls (See Example 1). A significantly lower ADE level of the C3 convertase inhibitor CD55 may explain the higher levels of C3 convertase-generated C3b. ADE levels of the neuroprotective protein leukemia inhibitory factor (LIF) were significantly lower in psychotic subjects relative to matched controls (See Example 1). Hence, exosomal biomarker abnormalities are associated with development or worsening of psychosis. Accordingly, detection of exosomal biomarker abnormalities can be used to identify individuals who will benefit from therapy.

In some embodiments, the subject is a mammalian subject, including. e.g., a cat, a dog, a rodent, etc. In certain embodiments, the subject is a human subject.

In some embodiments, the present disclosure enables a medical practitioner to diagnose or prognose psychosis and/or schizophrenia in a subject. In yet other embodiments, the present disclosure enables a medical practitioner to identify a subject at risk of developing psychosis and/or schizophrenia. In other embodiments, the present disclosure enables a medical practitioner to predict whether a subject will later develop psychosis and/or schizophrenia. In further embodiments the present disclosure enables a medical practitioner to prescribe a therapeutic regimen or predict benefit from therapy in a subject having psychosis and/or schizophrenia or at risk of developing psychosis and/or schizophrenia. For example, the administration of one or more recombinant complement control proteins early in psychosis and/or schizophrenia, guided by their levels in exosomes of individual patients, could limit recruitment of complement mechanisms preventatively. In later phases of psychosis and/or schizophrenia, when complement activation has appeared, neutralizing monoclonal antibodies to complement components or their receptors, decoy complement receptors or receptor antagonists, and esterase inhibitors of complement mediator generation may suppress ongoing complement-mediated injury.

Biomarkers

Exosomal cargo levels of biomarker proteins are assayed for a subject having or at-risk of having depression, psychosis and/or schizophrenia. In some embodiments, one or more biomarkers selected from the group consisting of a mitochondrial electron transport protein, a cytokine, and a complement protein are assayed in order to detect whether or not a subject has depression, psychosis and/or schizophrenia. In some embodiments, one or more biomarkers selected from the group consisting of human tetraspanning exosome marker CD81, subunit 6 of NADH-ubiquinone oxidoreductase (complex I), decay-accelerating factor (CD55), glutamine synthetase, subunit 1 of cytochrome C oxidase (complex IV), subunit 1 of NADH-ubiquinone oxidoreductase (complex I), subunit 10 of cytochrome b-c1 oxidase (complex III), glial fibrillary acidic protein, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2) and mitochondrial open-reading frame of the 12S rRNA-c (MOTS-c) are assayed in order to detect whether or not a subject has depression, psychosis and/or schizophrenia. In some embodiments, the one or more biomarkers are assayed in the preclinical phase.

One of ordinary skill in the art has several methods and devices available for the detection and analysis of the biomarkers of the instant disclosure. With regard to polypeptides or proteins in patient test samples, immunoassay devices and methods are often used. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule.

Preferably the markers are analyzed using an immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, enzyme-linked immunoassays (ELISA), radioimmunoassay (RIAs), competitive binding assays, planar waveguide technology, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies specific for the biomarkers is also contemplated by the present disclosure. The antibodies could be immobilized onto a variety of solid supports, such as magnetic or chromatographic matrix particles, the surface of an assay place (such as microtiter wells), pieces of a solid substrate material (such as plastic, nylon, paper), and the like. An assay strip could be prepared by coating the antibody or a plurality of antibodies in an army on solid support. This strip could then be dipped into the test sample and then processed quickly through washes and detection steps to generate a measurable signal, such as a colored spot.

The analysis of a plurality of biomarkers may be carried out separately or simultaneously with one test sample. Several biomarkers may be combined into one test for efficient processing of a multiple of samples. In addition, one skilled in the art would recognize the value of testing multiple samples (for example, at successive time points) from the same individual. Such testing of serial samples will allow the identification of changes in marker levels over time. Increases or decreases in biomarker levels, as well as the absence of change in biomarker levels, would provide useful information about disease status that includes, but is not limited to the appropriateness of drug therapies, the effectiveness of various therapies, identification of the severity of depression, psychosis and/or schizophrenia, susceptibility to depression, psychosis and/or schizophrenia, and prognosis of the patient's outcome, including risk of development of depression, psychosis and/or schizophrenia.

An assay consisting of a combination of the biomarkers referenced in the instant disclosure may be constructed to provide relevant information related to differential diagnosis. Such a panel may be constructed using 1, 2, 3, 4, 5, 6, 7, 8, 9, 10, 15, 20, or more individual markers. The analysis of a single biomarker or subsets of biomarkers comprising a larger panel of biomarkers could be carried out using methods described within the instant disclosure to optimize clinical sensitivity or specificity in various clinical settings.

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings. Particularly useful physical formats comprise surfaces having a plurality of discrete, addressable locations for the detection of a plurality of different analytes. Such formats include protein microarrays, or "protein chips" and capillary devices.

Biomarkers of the present disclosure serve an important role in the early detection and monitoring of depression, psychosis and/or schizophrenia. Biomarkers are typically substances found in a bodily sample that can be measured. The measured amount can correlate with underlying disorder or disease pathophysiology and probability of developing depression, psychosis and/or schizophrenia in the future. In patients receiving treatment for their condition, the measured amount will also correlate with responsiveness to therapy.

In some embodiments, the biomarker is measured by a method selected from the group consisting of immunohistochemistry, immunocytochemistry, immunofluorescence, immunoprecipitation, western blotting, and ELISA.

Clinical Assay Performance

The methods of the present disclosure for detecting depression, psychosis and/or schizophrenia may be used in clinical assays to diagnose or prognose depression, psychosis and/or schizophrenia in a subject, identify a subject at risk of depression, psychosis and/or schizophrenia, and/or for prescribing a therapeutic regimen or predicting benefit from therapy in a subject having depression, psychosis and/or schizophrenia. Clinical assay performance can be assessed by determining the assay's sensitivity, specificity, area under the ROC curve (AUC), accuracy, positive predictive value (PPV), and negative predictive value (NPV). Disclosed herein are assays for diagnosing or prognosing depression, psychosis and/or schizophrenia in a subject, identifying a subject at risk of depression, psychosis and/or schizophrenia, or for prescribing a therapeutic regimen or predicting benefit from therapy in a subject having depression, psychosis and/or schizophrenia.

The clinical performance of the assay may be based on sensitivity. The sensitivity of an assay of the present disclosure may be at least about 40%, 45%, 50%, 55%, 60%, 65%, 70%, 75%, 80%, 85%, 90%, 95%, 99%, or 100%. The clinical performance of the assay may be based on specificity. The specificity of an assay of the present disclosure may be at least about 40%, 45%, 50%, 55%, 60%, 65%, 70%, 75%, 80%, 85%, 90%, 95%, 99%, or 100%. The clinical performance of the assay may be based on area under the ROC curve (AUC). The AUC of an assay of the present disclosure may be at least about 0.5, 0.55, 0.6, 0.65, 0.7, 0.75, 0.8, 0.85, 0.9, or 0.95. The clinical performance of the assay may be based on accuracy. The accuracy of an assay of the present disclosure may be at least about 40%, 45%, 50%, 55%, 60%, 65%, 70%, 75%, 80%, 85%, 90%, 95%, 99%, or 100%.

Agents and Compositions

Agents and compositions useful in the methods of the present disclosure include agents and compositions that specifically recognize one or more exosomal biomarkers associated with depression, psychosis and/or schizophrenia, including a mitochondrial electron transport protein, a cytokine, and a complement protein or any combination thereof. In some embodiments, the one or more exosomal biomarker is human tetraspanning exosome marker CD81, subunit 6 of NADH-ubiquinone oxidoreductase (complex I), decay-accelerating factor (CD55), glutamine synthetase, subunit 1 of cytochrome C oxidase (complex IV), subunit 1 of NADH-ubiquinone oxidoreductase (complex I), subunit 10 of cytochrome b-c1 oxidase (complex III), glial fibrillary acidic protein, complement fragment C3b, TCC C5b-9, superoxide dismutase 1 (SOD1), CD59, IL-6, neuron-specific enolase, leukemia inhibitory factor (LIF), mitochondrial electron transport chain complexes I and II, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2), Peroxisome proliferator-activated receptor gamma coactivator 1-alpha (PGC-1α), Nuclear factor erythroid 2-related factor 2 (NRF2), and/or mitochondrial open-reading frame of the 12S rRNA-c (MOTS-c) or any combination thereof. In some embodiments, the agent or composition enhances the activity of at least one biomarker. In other embodiments, the agent or composition decreases the activity of at least one biomarker. In some embodiments, the agent composition increases the levels of at least one biomarker in the subject. In other embodiments, the agent composition decreases the levels of at least one biomarker in the subject. In yet other embodiments, the agent composition comprises a peptide, a nucleic acid, an antibody, or a small molecule.

In certain embodiments, the present disclosure relates to agents and/or compositions that specifically detect a biomarker associated with depression, psychosis and/or schizophrenia. As detailed elsewhere herein, the disclosure is based upon the finding that mitochondrial electron transport proteins, cytokines, and complement proteins are specific biomarkers for depression, psychosis and schizophrenia. In one embodiment, the compositions of the disclosure specifically bind to and detect one or more of the following biomarkers: human tetraspanning exosome marker CD81, subunit 6 of NADH-ubiquinone oxidoreductase (complex I), decay-accelerating factor (CD55), glutamine synthetase, subunit 1 of cytochrome C oxidase (complex IV), subunit 1 of NADH-ubiquinone oxidoreductase (complex I), subunit 10 of cytochrome b-c1 oxidase (complex III), glial fibrillary acidic protein, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2), Peroxisome proliferator-activated receptor gamma coactivator 1-alpha (PGC-1α), Nuclear factor erythroid 2-related factor 2 (NRF2), and/or mitochondrial open-reading frame of the 12S rRNA-c (MOTS-c), or any combination thereof. The agent and/or composition of the disclosure can comprise an antibody, a peptide, a small molecule, a nucleic acid, and the like.

In some embodiments, the agent and/or composition comprises an antibody, wherein the antibody specifically binds to a biomarker or exosome. The term "antibody" as used herein and further discussed below is intended to include fragments thereof which are also specifically reactive with a biomarker or vesicle (e.g., exosome). Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. Antigen-binding portions may also be produced by recombinant DNA techniques or by enzymatic or chemical cleavage of intact antibodies. Antigen-binding portions include, inter alia, Fab, Fab', F(ab')$_2$, Fv, dAb, and complementarity determining region (CDR) fragments, single-chain antibodies (scFv), single domain antibodies, bispecific antibodies, chimeric antibodies, humanized antibodies, diabodies and polypeptides that contain at least a portion of an immunoglobulin that is sufficient to confer specific antigen binding to the polypeptide. In certain embodiments, the antibody further comprises a label attached thereto and able to be detected (e.g., the label can be a radioisotope, fluorescent compound, enzyme or enzyme co-factor).

In certain embodiments, an antibody of the disclosure is a monoclonal antibody, and in certain embodiments, the disclosure makes available methods for generating novel antibodies that specifically bind the biomarker or the exosome of the disclosure. For example, a method for generating a monoclonal antibody that specifically binds a biomarker or exosome, may comprise administering to a mouse an amount of an immunogenic composition comprising the biomarker or exosome, or fragment thereof, effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the biomarker or exosome. Once obtained, a hybridoma can be propagated in a cell culture, optionally in culture conditions where the hybridoma-derived cells produce the monoclonal antibody that binds specifically to the biomarker or exosome. The monoclonal antibody may be purified from the cell culture.

The term "specifically reactive with" or "specifically binds" as used in reference to an antibody is intended to mean, as is generally understood in the art, that the antibody is sufficiently selective between the antigen of interest (e.g., a biomarker or exosome) and other antigens that are not of interest. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less.

Antibodies can be generated to bind specifically to an epitope of an exosome or a biomarker of the present disclosure, including, for example, exosome surface markers, such as Glutamine Aspartate Transporter (GLAST) or CD171 (L1CAM neural adhesion protein).

In addition, the techniques used to screen antibodies in order to identify a desirable antibody may influence the properties of the antibody obtained. A variety of different techniques are available for testing interaction between antibodies and antigens to identify particularly desirable antibodies. Such techniques include ELISAs, surface plasmon resonance binding assays (e.g., the Biacore binding assay, Biacore AB, Uppsala, Sweden), sandwich assays (e.g., the paramagnetic bead system of IGEN International, Inc., Gaithersburg, Md.), western blots, immunoprecipitation assays, immunocytochemistry, and immunohistochemistry.

In some embodiments, the present disclosure relates to agent and/or compositions used for treating or preventing depression, psychosis and/or schizophrenia. As detailed elsewhere herein, abnormal levels of exosomal biomarkers are implicated in the pathology of depression, psychosis and/or schizophrenia. Therefore, in one embodiment, the present disclosure provides compositions that inhibit or reduce abnormalities in levels of exosomal biomarkers. Compositions and agents useful for preventing and/or reducing abnormalities in levels of exosomal biomarkers may include proteins, peptides, nucleic acids, small molecules, and the like. In some embodiments, the agent is a SOD1 mimetic, a C3 convertase inhibitor, a LIF supplement, a LIF receptor agonist, or a ROS scavenger.

Methods of Treatment

The present disclosure provides methods for treating depression, psychosis and/or schizophrenia in a subject, the method comprising administering an effective amount of a SOD1 mimetic, a C3 convertase inhibitor, a LIF supplement, a LIF receptor agonist, and/or a ROS scavenger to a subject having or suspected of having depression, psychosis and/or schizophrenia, thereby treating the depression, psychosis and/or schizophrenia.

Generally, the therapeutic/diagnostic agents used in the disclosure am administered to a subject in an effective amount. Generally, an effective amount is an amount effective to (1) reduce the symptoms of the depression, psychosis and/or schizophrenia to be treated, (2) induce a pharmacological change relevant to treating the depression, psychosis and/or schizophrenia to be treated or (3) detect depression, psychosis and/or schizophrenia in vivo or in vitro. For example, an effective amount of an agent of the disclosure includes an amount effective to: prevent or reduce delusions, hallucinations or disorganized speech in a subject with or suspected of having depression, psychosis and/or schizophrenia.

Effective amounts of the agents can be any amount or dose sufficient to bring about the desired effect and will depend, in part, on the condition, type of depression, psychosis and/or schizophrenia, the size and condition of the patient, as well as other factors readily known to those skilled in the art. The dosages can be given as a single dose, or as several doses, for example, divided over the course of several weeks. It is specifically contemplated that therapeutic agent may need to be administered immediately (or as soon as possible) and for several months following depression, psychosis and/or schizophrenia diagnosis to be optimally effective.

The disclosure is also directed toward methods of treatment utilizing the therapeutic compositions of the present disclosure. The method comprises administering the therapeutic agent to a subject in need of such administration, such as, for example, a subject with depression, psychosis and/or schizophrenia.

The therapeutic agents of the instant disclosure can be administered by any suitable means as described herein, including, for example, parenteral, topical, oral or local administration, such as intradermally, by injection, or by aerosol. In one embodiment of the disclosure, the agent is administered by injection. Such injection can be locally administered to any affected area. A therapeutic composition can be administered in a variety of unit dosage forms depending upon the method of administration. For example, unit dosage forms suitable for oral administration of a subject include powder, tablets, pills and capsules. Preferred delivery methods for a therapeutic composition of the disclosure include intravenous administration and local administration by, for example, injection or topical administration. For particular modes of delivery, a therapeutic composition of the disclosure can be formulated in an excipient of the disclosure. A therapeutic agent of the disclosure can be administered to any subject, to mammals, and to humans.

The particular mode of administration will depend on the depression, psychosis and/or schizophrenia to be treated. It is contemplated that administration of the agents of the present disclosure may be via any bodily fluid, or any target or any tissue accessible through a body fluid.

In some embodiments, the complement pathway inhibitor is a neutralizing monoclonal antibody to effector complement components or their receptors, decoy complement receptors or receptor antagonists, or an esterase inhibitor. Complement inhibitors that may be used in the methods of the disclosure include the complement inhibitors disclosed in United States Patent Application Publication Number 2016/0096870, the contents of which are incorporated by reference in its entirety. In other embodiments, the agent is a SOD1 mimetic, a C3 convertase inhibitor, a LIF supplement, a LIF receptor agonist, or a ROS scavenger, or a combination thereof.

Furthermore, the methods of the disclosure can be used for monitoring the efficacy of therapy in a patient. The method comprises: analyzing the levels of one or more biomarkers selected from the group consisting of a mitochondrial electron transport protein, a cytokine, and a complement protein from exosomes from biological samples from the patient before and after the patient undergoes the therapy, in conjunction with respective reference levels for the biomarkers. Increased exosomal levels of complement proteins correlate with depression, psychosis severity and indicate that the patient is worsening or not responding to the therapy, and decreasing exosomal levels of complement proteins correlate with reduced depression, psychosis severity and indicate that the condition of the patient is improving. Decreasing exosomal levels of mitochondrial electron transport proteins correlate with increased depression, psychosis severity and indicate that the patient is worsening or not responding to the therapy, and increasing exosomal levels of mitochondrial electron transport proteins correlate with reduced depression, psychosis severity and indicate that the condition of the patient is improving.

In some embodiments, the methods of the disclosure provide a method for treating depression, psychosis and/or schizophrenia the method comprising the steps of: obtaining a biological sample from a subject suspected of having depression, psychosis and/or schizophrenia, wherein the sample comprises exosomes; measuring the level of one or more biomarkers selected from the group consisting of a mitochondrial electron transport protein, a cytokine, and a complement protein from the biological sample, wherein an altered level of the one or more biomarkers in the sample relative to the level in a control sample is indicative of a need for treatment; and administering an effective amount of an agent to the subject thereby treating depression, psychosis and/or schizophrenia in the subject. In some embodiments, the biomarker comprises human tetraspanning exosome marker CD81, subunit 6 of NADH-ubiquinone oxidoreductase (complex I), decay-accelerating factor (CD55), glutamine synthetase, subunit 1 of cytochrome C oxidase (complex IV), subunit 1 of NADH-ubiquinone oxidoreductase (complex I), subunit 10 of cytochrome b-c1 oxidase (complex III), glial fibrillary acidic protein, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), humanin, Sterile alpha and TIR motif containing 1 (SARM 1), Transcription factor A, mitochondrial (TFAM), Nicotinamide nucleotide adenylyltransferase 2 (NMNAT 2), Peroxisome proliferator-activated receptor gamma coactivator 1-alpha (PGC-1α), Nuclear factor erythroid 2-related factor 2 (NRF2), and/or mitochondrial open-reading frame of the 12S rRNA-c (MOTS-c).

Kits

Another aspect of the disclosure encompasses kits for detecting or monitoring depression, psychosis and/or schizophrenia in a subject. A variety of kits having different components are contemplated by the current disclosure. Generally speaking, the kit will include the means for quantifying one or more biomarkers in a subject. In another embodiment, the kit will include means for collecting a biological sample, means for quantifying one or more biomarkers in the biological sample, and instructions for use of the kit contents. In certain embodiments, the kit comprises a means for enriching or isolating exosomes in a biological sample. In some embodiments, the exosomes are astrocyte-derived exosomes and/or neuron-derived exosomes. In further aspects, the means for enriching or isolating exosomes comprises reagents necessary to enrich or isolate exosomes from a biological sample. In certain aspects, the kit comprises a means for quantifying the amount of a biomarker. In further aspects, the means for quantifying the amount of a biomarker comprises reagents necessary to detect the amount of a biomarker.

These and other embodiments of the present disclosure will readily occur to those of ordinary skill in the art in view of the disclosure herein.

EXAMPLES

The disclosure will be further understood by reference to the following examples, which are intended to be purely exemplary of the disclosure. These examples are provided solely to illustrate the claimed disclosure. The present disclosure is not limited in scope by the exemplified embodiments, which are intended as illustrations of single aspects of the disclosure only. Any methods that are functionally equivalent are within the scope of the disclosure. Various modifications of the disclosure in addition to those described herein will become apparent to those skilled in the art from the foregoing description. Such modifications are intended to fall within the scope of the appended claims.

Example 1: Psychosis Alters Plasma Astrocyte-Derived Exosome and Neuron-Derived Exosome Levels of Complement, Cytokine, and Mitochondrial Electron Transport Proteins Complement proteins, cytokines, and mitochondrial electron transport proteins were detected and measured in astrocyte-derived exosomes and neuron-derived exosomes from subjects with psychosis as follows. Subjects were recruited from a Specialized Treatment Early in Psychosis (STEP) program of the Connecticut Mental Health Center (New Haven, CT). All had suffered onset of psychosis within two years before recruitment. Excluded were those with affective psychosis, with psychosis secondary to substance use or medical illness, pregnant or breast-feeding, with evidence of any inflammation or exposure to any drug affecting inflammation in the prior four weeks, unable to communicate in English, or with co-morbid unstable serious medical illness. On admission, all participants were assessed for severity of psychosis and mood symptoms, neurocognitive function, and premorbid life state and adjustments, including the Total (score 30-210) and General Psychopathology (score 16-112) Positive and Negative Syndrome Scales (PANSS) (Srihari et al. BMC Psychiatry. 2014:14:335). Ten consecutive first-episode psychotics (FPs) with a duration of untreated psychosis shorter than two years were selected for this study (Miller et al. Schizophr Bull. 2003; 29:703-715).

Ten milliliters of venous blood were drawn into 0.5 ml saline with EDTA, incubated for 10 minutes at room temperature, and centrifuged for 15 minutes at 2500×g. Plasmas were stored in 0.25-ml aliquots at −80° C.

Aliquots of 0.25 mL plasma were incubated with 0.1 mL of thromboplastin D (Thermo Fisher Scientific, Waltham, MA) for 30 min at room temperature, followed by addition of 0.15 mL of calcium- and magnesium-free Dulbecco's balanced salt solution (DBS) with protease inhibitor cocktail (Roche, Indianapolis, IN) and phosphatase inhibitor cocktail (Thermo Fisher Scientific; DBS++) as described (10, 11). After centrifugation at 3000×g for 30 minutes at 4° C., total exosomes were harvested from resultant supernatants by precipitation with 126 µL per tube of ExoQuick (System Biosciences, Mountain View, CA) and centrifugation at 1500×g for 30 minutes at 4° C. To separately enrich neuron-derived exosomes (NDEs) and astrocyte-derived exosomes (ADEs), replicate preparations of total exosomes were resuspended in 0.35 mL of DBS and incubated for 60 minutes at room temperature with either 2.0 µg of mouse anti-human CD171 (L1CAM neural adhesion protein) biotinylated antibody (clone 5G3; eBiosciences, San Diego, CA) or mouse anti-human glutamine aspartate transporter (GLAST, ACSA-1) biotinylated antibody (Miltenyi Biotec, Auburn, CA), respectively, in 50 µL of 3% bovine serum albumin (BSA; 1:3.33 dilution of Blocker BSA 10% solution in DBS; Thermo Fisher Scientific) per tube with mixing, followed by addition of 10 µL of streptavidin agarose Ultralink resin (Thermo Fisher Scientific) in 40 µL of 3% BSA and incubation for 30 minutes at room temperature with mixing. After centrifugation at 800×g for 10 minutes at 4° C. and removal of the supernatant, each pellet was suspended in 100 µL of cold 0.05M glycine-HCl (pH 3.0) by gentle mixing for 10 seconds and centrifuged at 4000×g for 10 minutes, all at 4° C. Supernatants then were transferred to clean tubes containing 25 µL of 10% BSA and 10 µL of 1 M Tris-HCl (pH 8.0) and mixed gently. An aliquot of 5 µL was removed from each tube for EV counts before addition of 370 µL of mammalian protein extraction reagent (M-PER, Thermo Fisher Scientific). Resultant 0.5 mL lysates of NDEs and ADEs were stored at −80° C.

For counting and sizing of exosomes, each suspension was diluted 1:50 in PBS. The mean diameter (nanometers) and concentration (particles per milliliter) of exosomes in each suspension were determined by nanoparticle tracking analysis (NTA) using the Nanosight NS500 system with a G532 nm laser module and NTA 3.1 nanoparticle tracking software (Malvern Instruments, Malvern, United Kingdom). Camera settings were as follows: gain 366; shutter 31.48; and frame rate 24.9825 frames/s. Brownian motion was captured by performing 5 repeated 60 s video recordings.

ADE and NDE proteins were quantified by enzyme-linked immunosorbent assay (ELISA) kits for human tetraspanning exosome marker CD81, subunit 6 of NADH-ubiquinone oxidoreductase (complex I), decay-accelerating factor (CD55) (Cusabio Technology by American Research Products, Waltham, MA), glutamine synthetase, subunit 1 of cytochrome C oxidase (complex IV) (Cloud-Clone Corp by American Research Products), subunit 1 of NADH-ubiquinone oxidoreductase (complex I) (DL-Develop Corp. by American Research Products), subunit 10 of cytochrome b-c1 oxidase (complex III) (Abbkine, Inc. by American Research Products), glial fibrillary acidic protein (Millipore-Sigma Corp., Burlington, MA), complement fragment C3b (Abcam, Cambridge, MA), TCC C5b-9 (Aviva Systems, San Diego, CA), superoxide dismutase 1 (SOD1), CD59 (Ray Biotech, Norcross, GA), IL-6, neuron-specific enolase (R&D Systems-Bio-Techne, Minneapolis, MN), and leukemia inhibitory factor (LIF) (Thermo Fisher Scientific, Waltham, MA).

The mean value for all determinations of CD81 in each assay group was set at 1.00, and relative values of CD81 for each sample were used to normalize their recovery.

Exosome Analyses

Mean 1 S.E.M. counts of ADEs in immuno-selected suspensions resembled those of past studies at $60.9\pm2.43\times10^7$/ml for controls and $61.3\pm2.80\times10^9$/ml for FP patients. Counts of NDEs were $134\pm3.92\times10^9$/ml for controls and $135\pm5.69\times10^7$/ml for FP patients. CD81 exosome marker levels in the ADE and NDE populations also showed no significant differences between those of controls and FP patients (FIG. 1A). ADEs and NDEs of controls and FP patients were of similar sizes with diameters ranging from 64 to 120 nm for NDEs and 72-114 nm for ADEs. Levels of markers representative of each type of extracellular vesicle confirmed a high degree of enrichment. The neuron marker neuron-specific enolase was at a mean±S.E.M. of $5,816\pm142$ pg/ml in control NDE extracts and $290\pm31.4$ pg/ml in control ADE extracts. The astrocyte marker glial fibrillary acidic protein (GFAP) was at a mean±S.E.M. of $111,614\pm14,822$ pg/ml in ADE extracts and $4,958\pm592$ pg/ml in NDE extracts.

Mitochondrial Electron Transport System Proteins

Figure 1B:
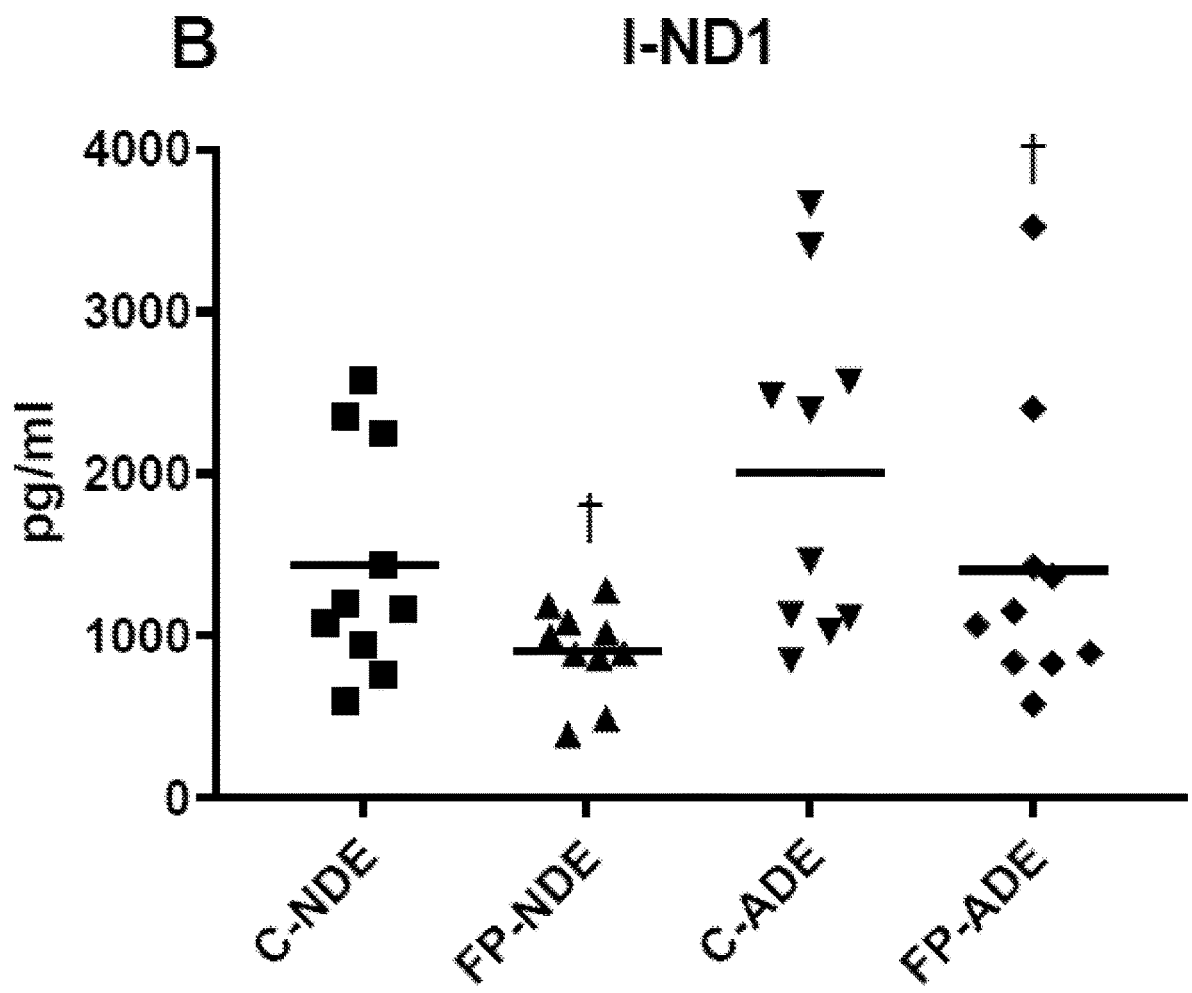
Figure 1C:
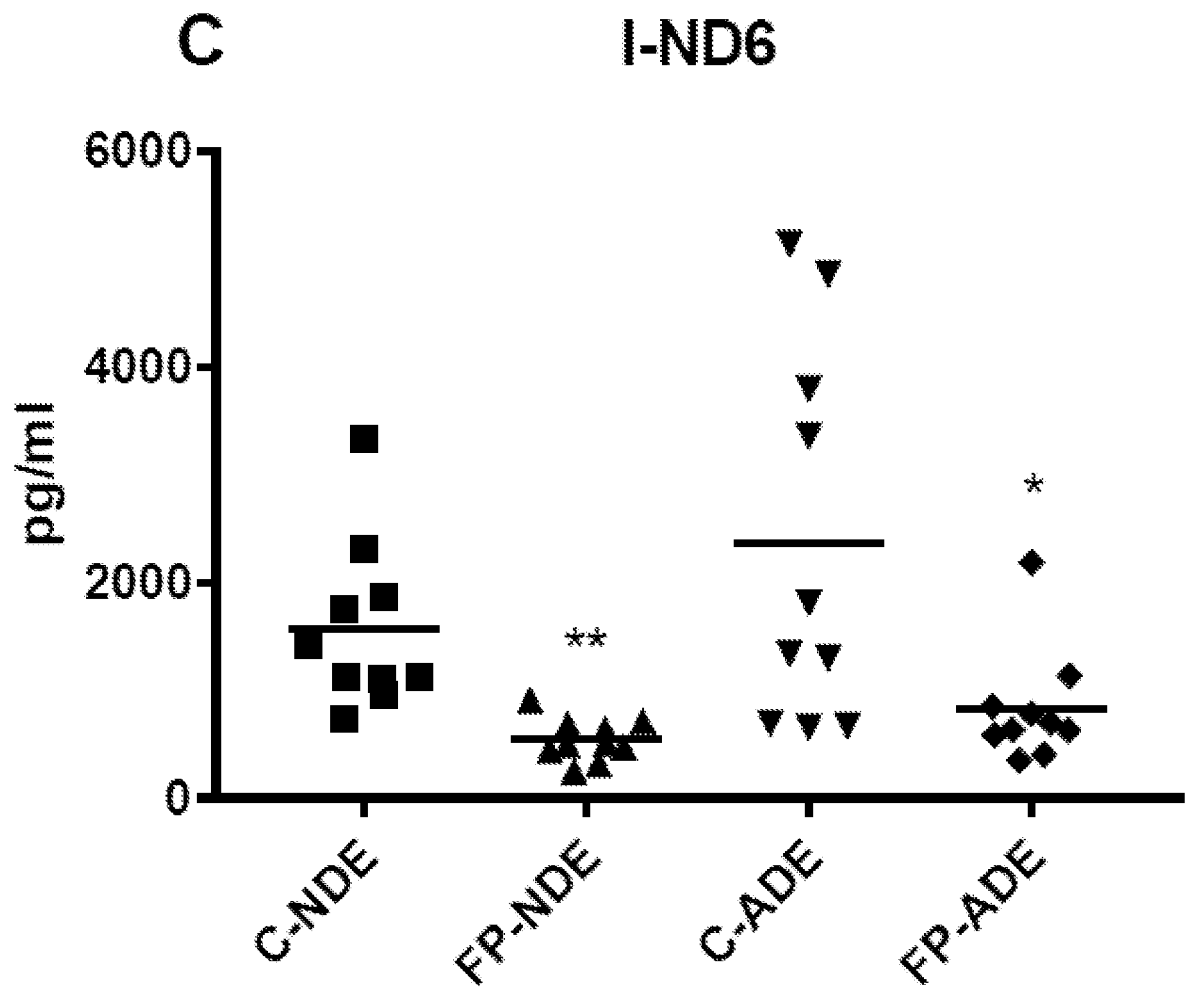
Figure 1D:
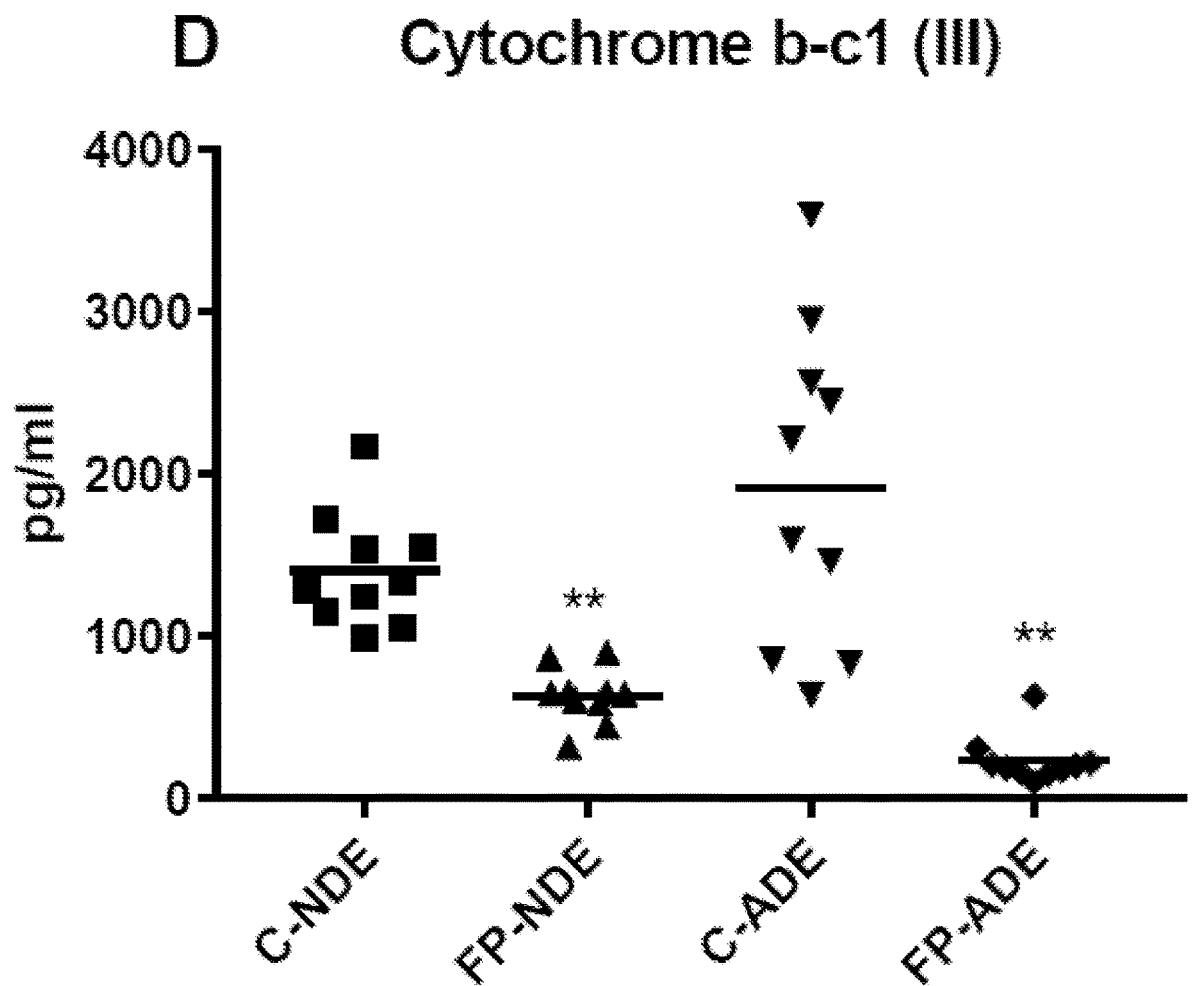
Figure 1E:
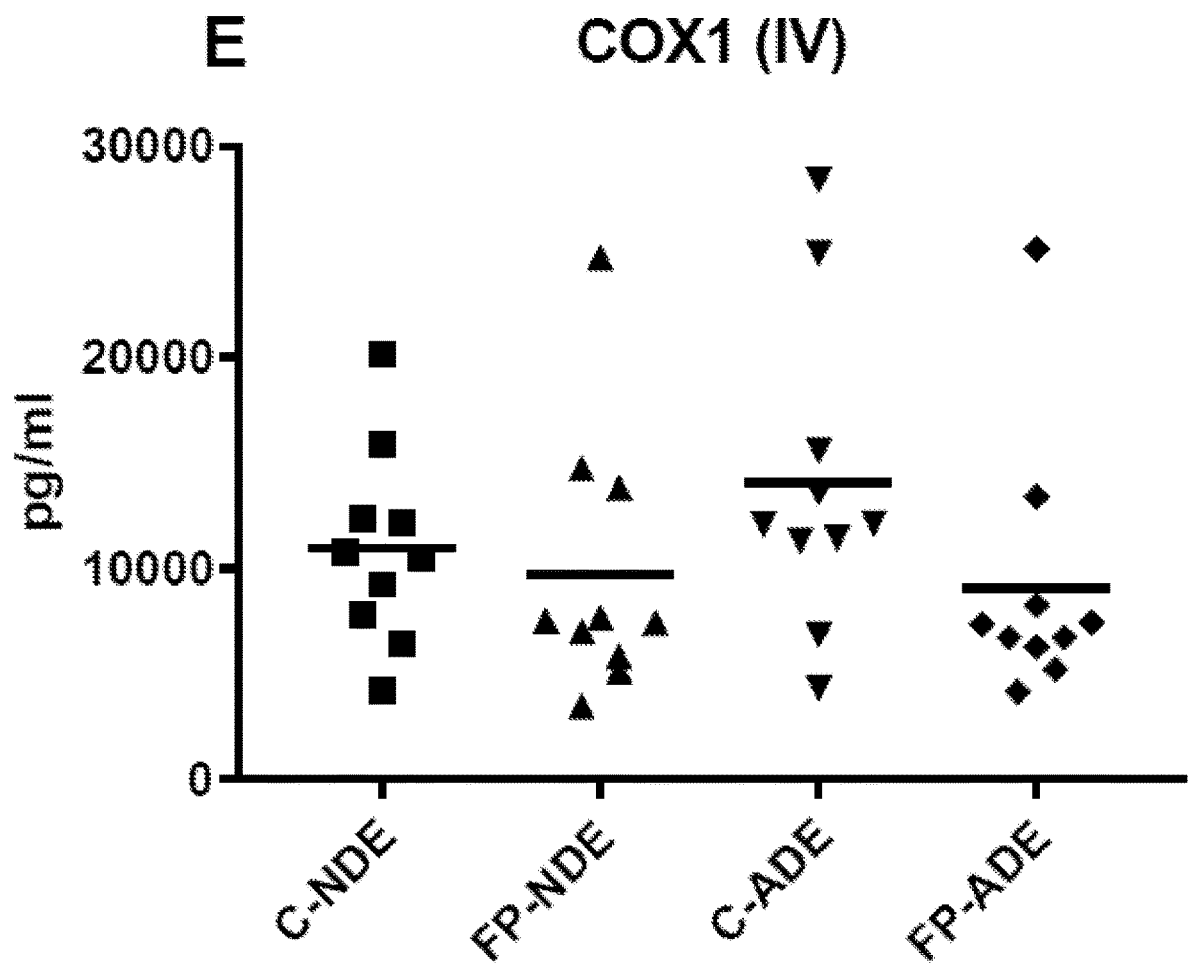

CD81-normalized ADE and NDE levels of subunit 1 of NADH-ubiquinone oxidoreductase (complex 1) were significantly lower in FP patients than controls, whereas those of the more catalytically important subunit 6 of NADH-ubiquinone oxidoreductase were significantly lower in FP patients than controls (FIG. 1B,C). CD81-normalized ADE and NDE levels of cytochrome b-c1 oxidase (coenzyme Q-cytochrome C oxidoreductase) (complex III) also were significantly lower in FP patients than controls (FIG. 1D). In contrast, CD81-normalized ADE and NDE levels of cytochrome C oxidase 1 (complex IV) were no different in FP patients than controls (FIG. 1E). This pattern of depressed levels of early mitochondrial electron transport complexes in the presence of a normal level of the terminal complex IV has been associated with increased generation of reactive oxygen species.

Figure 1F:
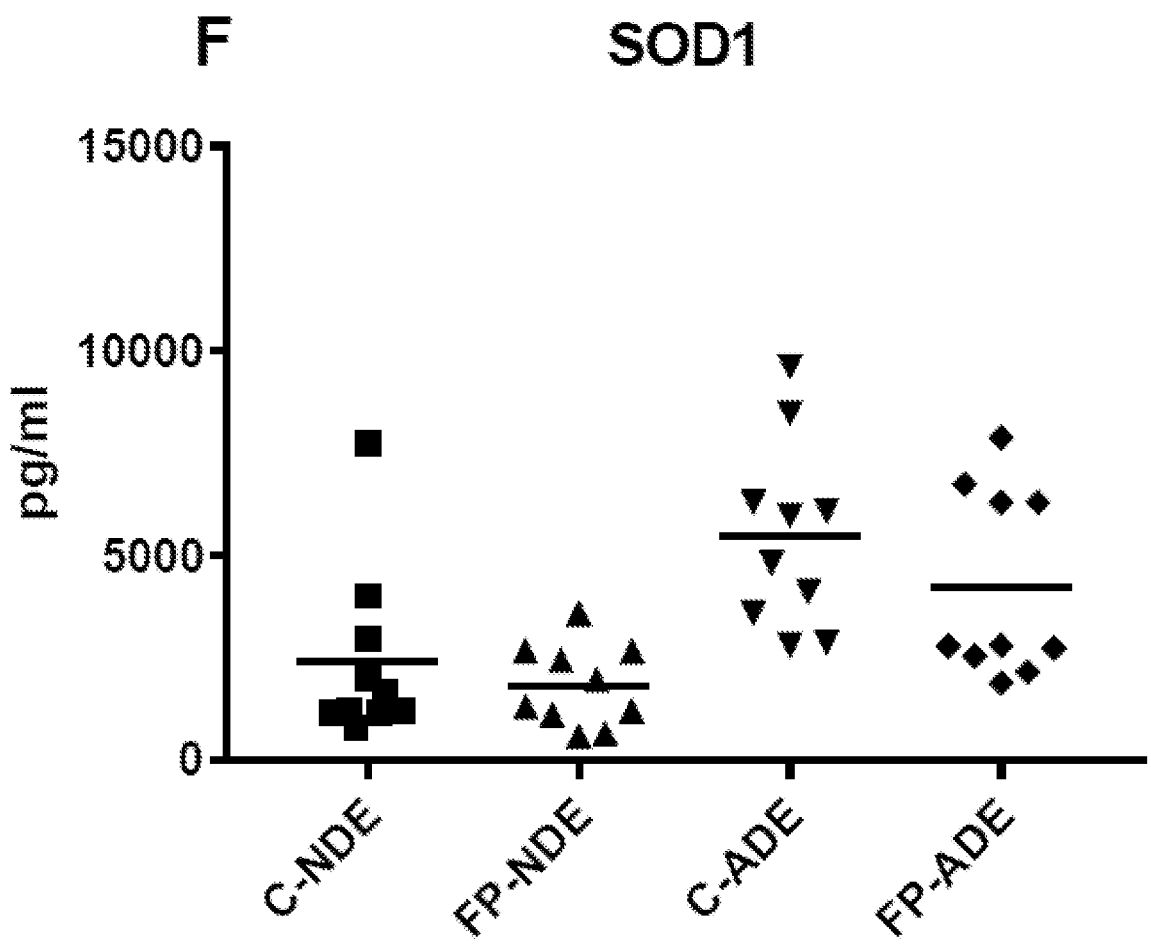

CD81-normalized ADE and NDE levels of superoxide dismutase 1 (SOD1), which is the predominant scavenger of mitochondrially-produced superoxide anion, were statistically the same in FP patients and controls (FIG. 1F).

Exosome Complement and Cytokine Constituents.

Figure 2A:
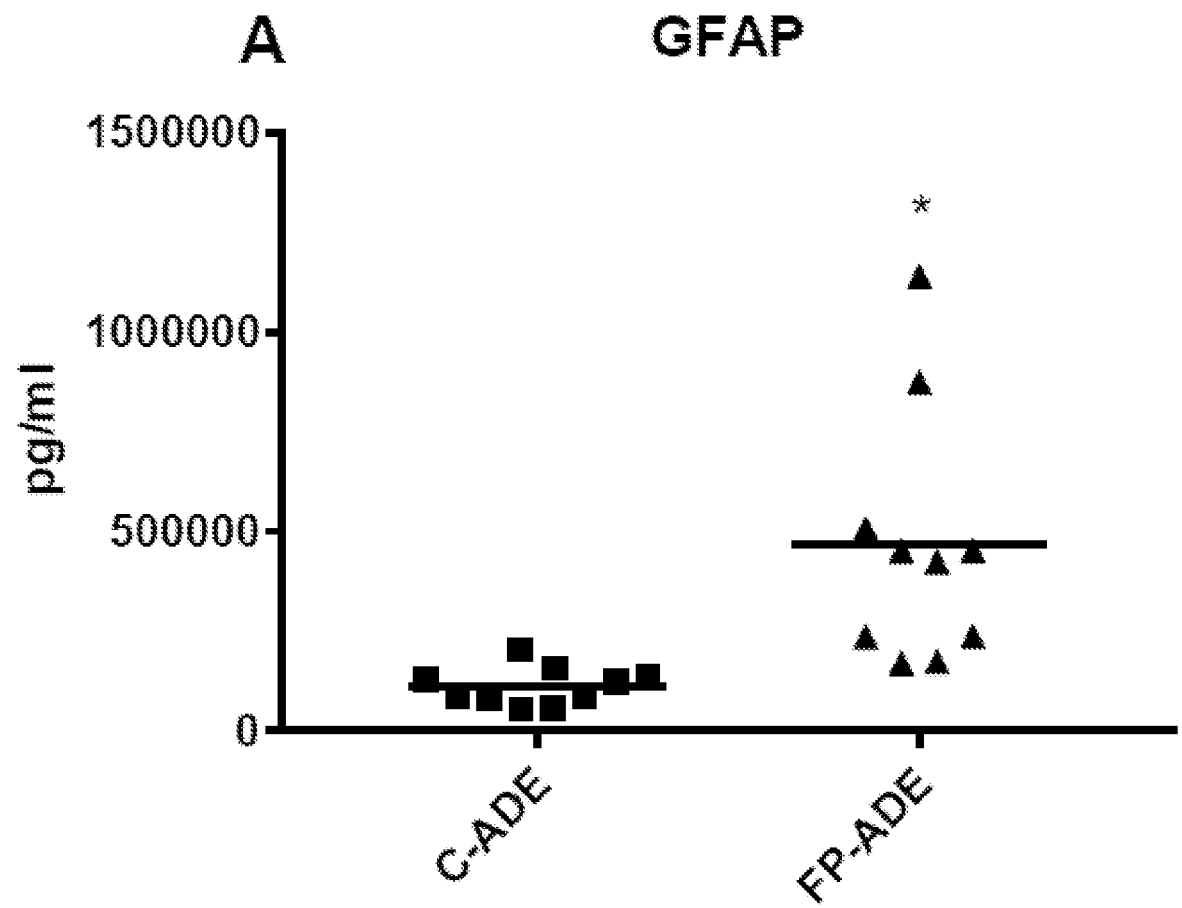
FIGS. 2A-2G set forth data showing complement and cytokine effector proteins in ADEs. Each point represents the value for one study participant. The mean±S.E.M. of control (C) and first-episode psychosis (FP) groups, respectively, were 111,641±14,822 pg/ml and 466,335±100,239 pg/ml for GFAP (A), 10,167±994 pg/ml and 117,468±26,305 pg/ml for C3b (B), 330±56.0 pg/ml and 573±100 pg/ml for C5b-9 (C), 49,621±6073 pg/ml and 7652±1452 pg/ml for CD55 (DAF) (D), 1087±299 pg/ml and 613±134 pg/ml for CD59 (E), 44.8±5.35 pg/ml and 45.0±5.85 pg/ml for IL-6 (F), and 1519±204 pg/ml and 424±64.2 pg/ml for LIF (G). Statistical significance of differences in values between C and FP groups were calculated by two sample t tests; †, $p<0.05$; *, $p<0.01$; **, $p<0.001$.
Figure 2B:
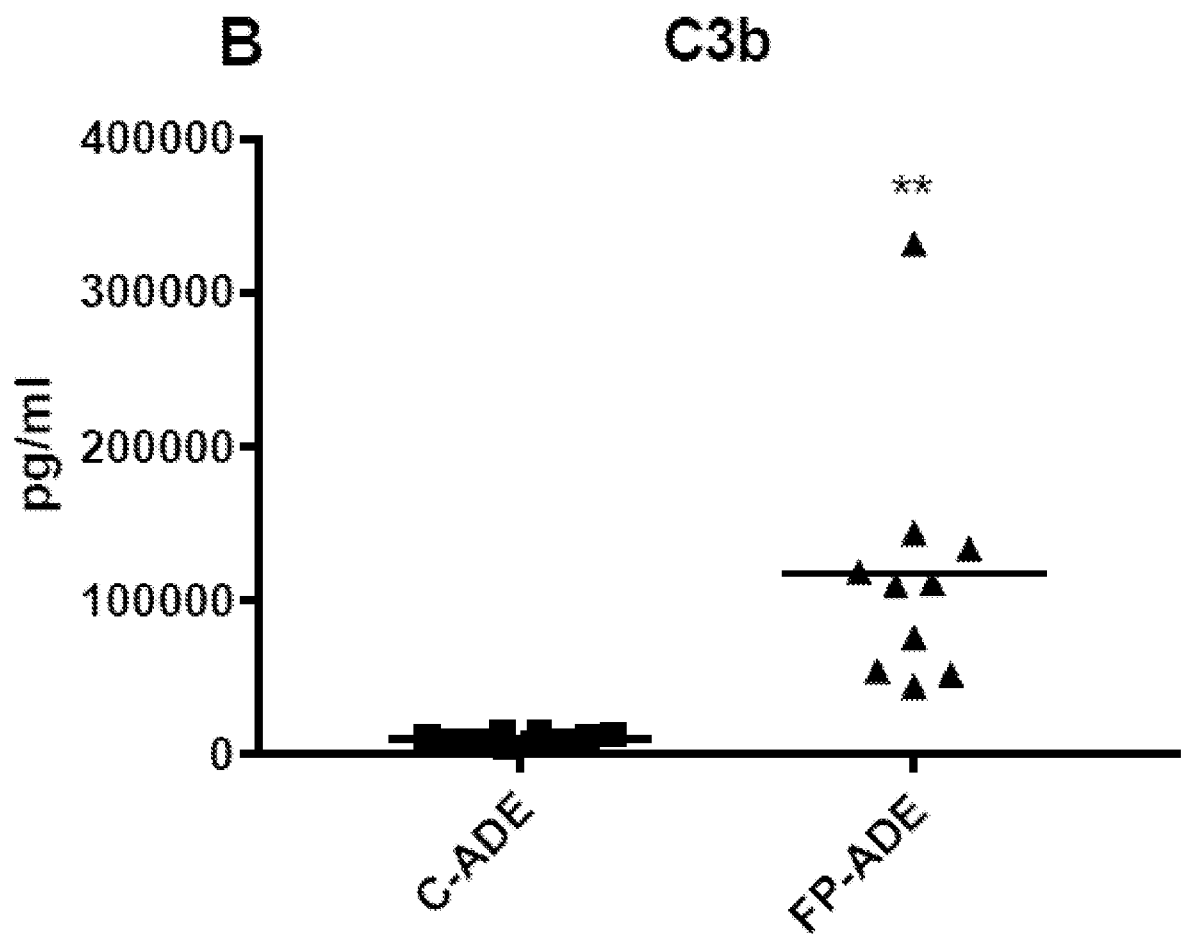
Figure 2C:
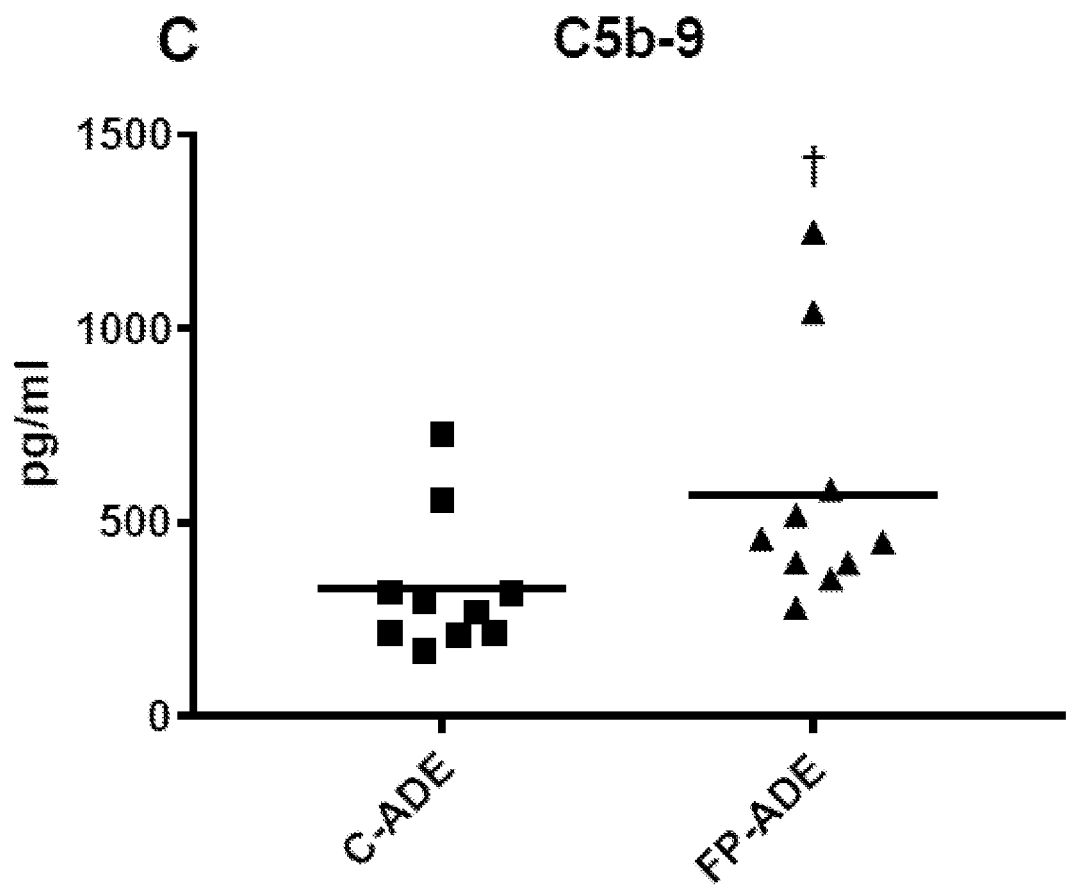
Figure 2D:
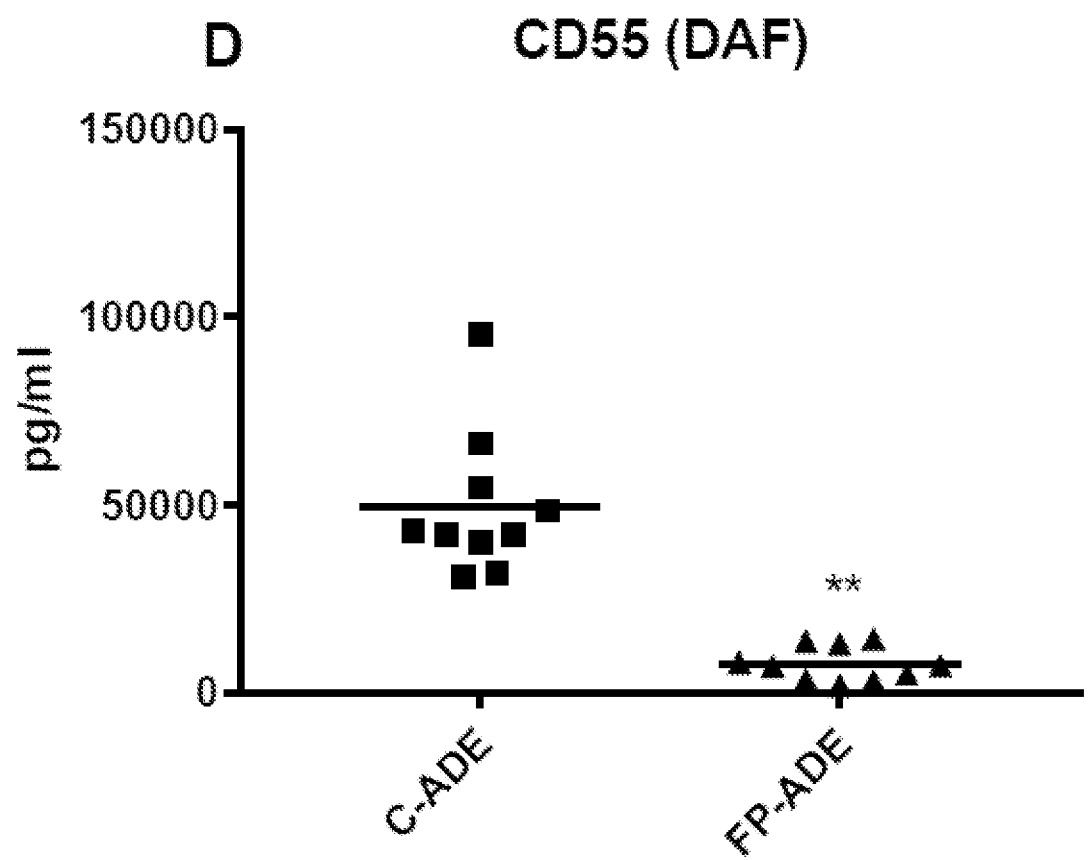
Figure 2E:
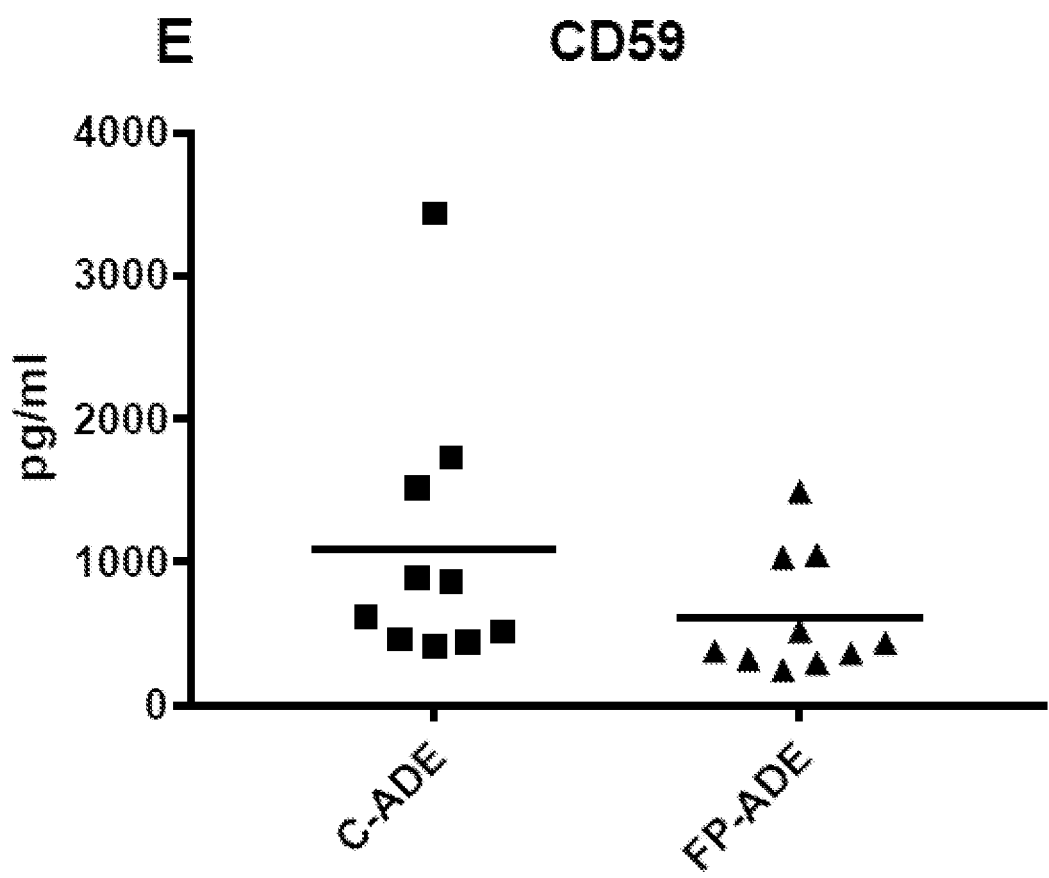

CD81-normalized ADE levels of GFAP, a major biomarker of inflammatory-type astrocytes, were significantly higher in FP patients than controls (FIG. 2A). As ADE counts and levels of the exosome marker CD81 were no different in FP patients than controls, the much higher levels of ADE GFAP in FP patients than controls is indicative of a higher proportion of activated inflammatory astrocytes in FP patients. Inflammatory-type astrocytes are the source of inflammatory neurotoxic complement mediators and their levels in ADEs reflect those in such astrocytes. ADE levels of neuron-opsonizing C3b were significantly higher in FP patients than controls (FIG. 2B), which is evidence of greater activation of astrocyte complement pathways in FP patients than controls. However, ADE levels of the directly neurotoxic C5b-9 attack complex were only marginally higher in FP patients than controls (FIG. 2C). This dissociation is at least partially explained by the ADE levels of membrane-associated complement regulatory proteins CD55 and CD59. CD55 levels were significantly lower in FP patients compared to those in controls, which would allow for higher generation of the C3b product by C3 convertases of both the classical and alternative pathways (FIG. 2D). The normal CD59 level of ADEs in FP patients relative to those in controls, however, would suppress formation of C5b-9 from C3b (FIG. 2E).

Figure 2F:
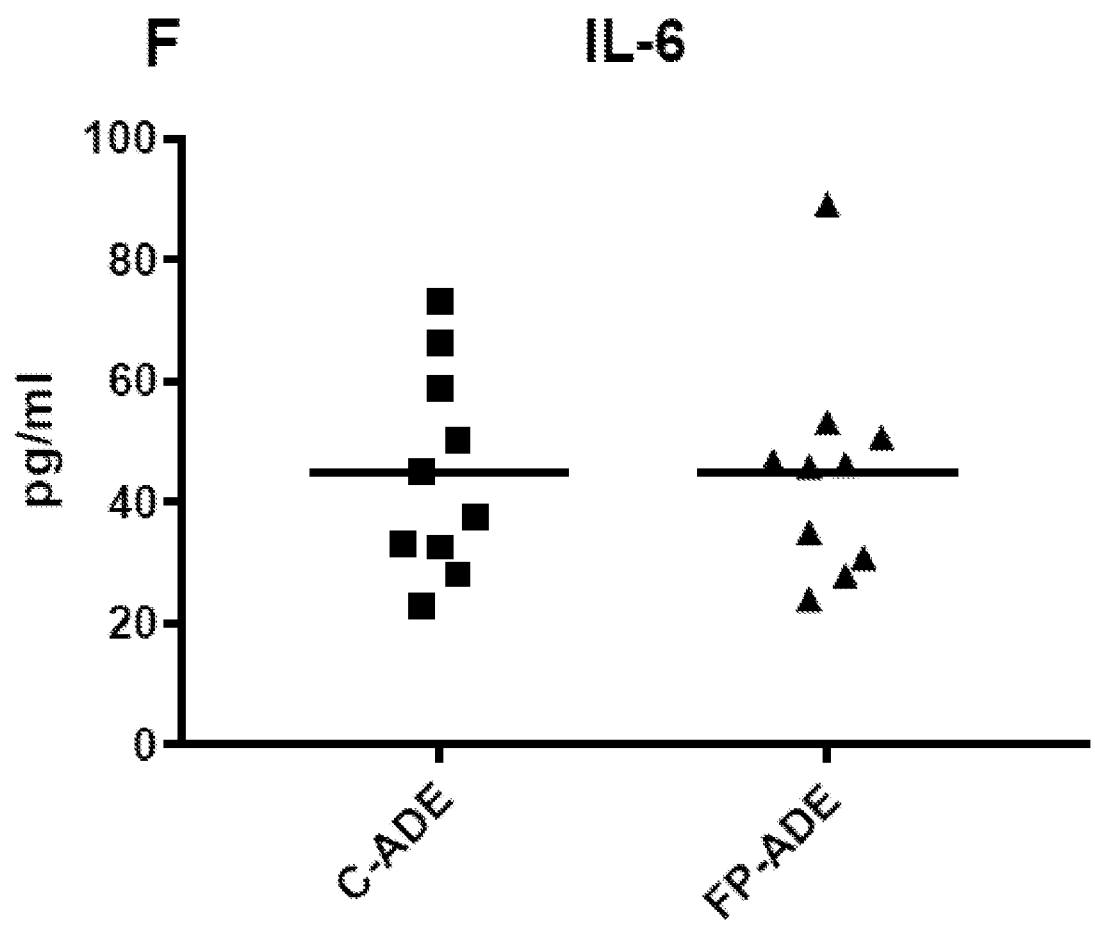
Figure 2G:
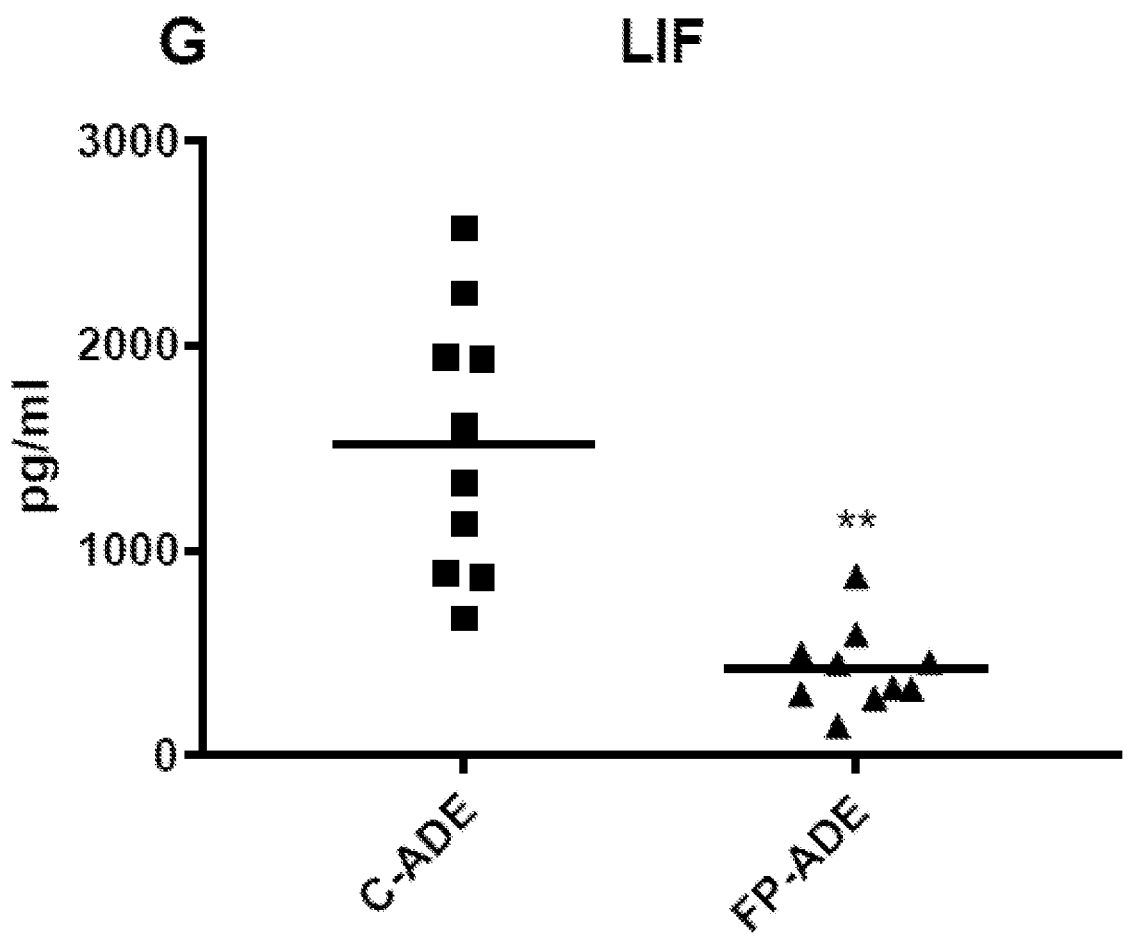
Figure 3A:
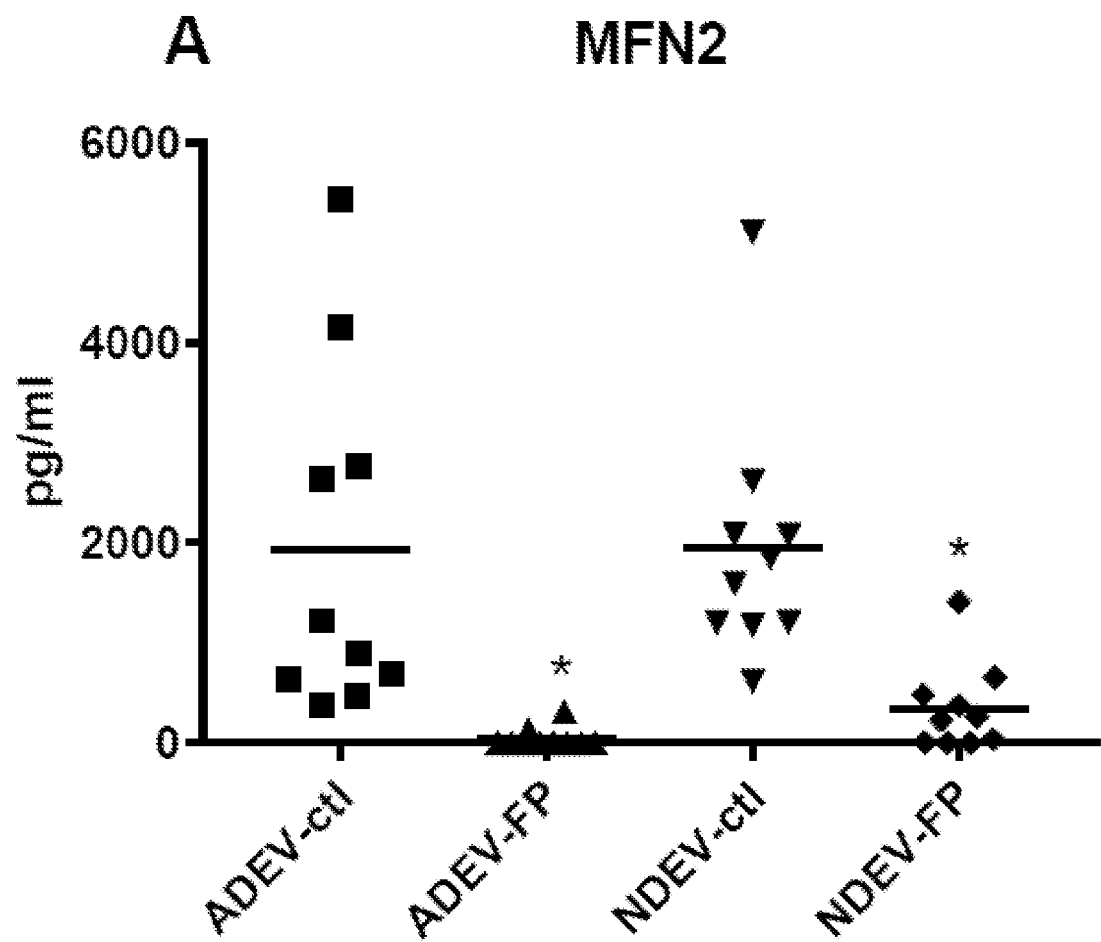
FIGS. 3A-3E set forth data showing abnormal levels of mitochondrial functional proteins in enriched populations of plasma ADEVs and NDEVs of patients with first-episode psychosis (FP). Each point represents the value for one study participant. The mean±S.E.M. of control (ctl) and FP groups, respectively, were 1931+556 pg/ml and 47.1+32.8 pg/ml for ADEVs ($p=0.0033$) and 1953+395 pg/ml and 347+138 pg/ml for NDEVs ($p=0.0012$) for mitofusin 2 (MFN2) (A); 1267+266 pg/ml and 231+39.4 pg/ml for ADEVs ($p=0.0012$) and 1456+133 pg/ml and 227+33.3 pg/ml for NDEVs ($p<0.0001$) for cyclophilin D (CYPD) (B); 392+29.0 pg/ml and 454+21.1 pg/ml for ADEVs ($p=0.098$) and 632+18.2 pg/ml and 628+16.6 pg/ml for NDEVs ($p=0.873$) for transcription factor A of mitochondria (TFAM) (C); 1550+501 pg/ml and 2037+369 pg/ml for ADEVs ($p=0.444$) and 2188+251 pg/ml and 4008+371 pg/ml for NDEVs ($p=0.0007$) for syntaphilin (SNPH) (D); and 4216+873 pg/ml and 5756+721 pg/ml for ADEVs ($p=0.191$) and 9599+1098 pg/ml and 11,240+1758 pg/ml for NDEVs ($p=0.439$) for myosin VI (MYO6) (E). All values in A-E and in FIG. 3 were normalized for content of the exosome marker CD81. Statistical significance of differences in values between ctl and FP groups for NDEVs and ADEVs were calculated by two sample t tests; *, $p<0.01$; **, $p<0.001$.
Figure 3B:
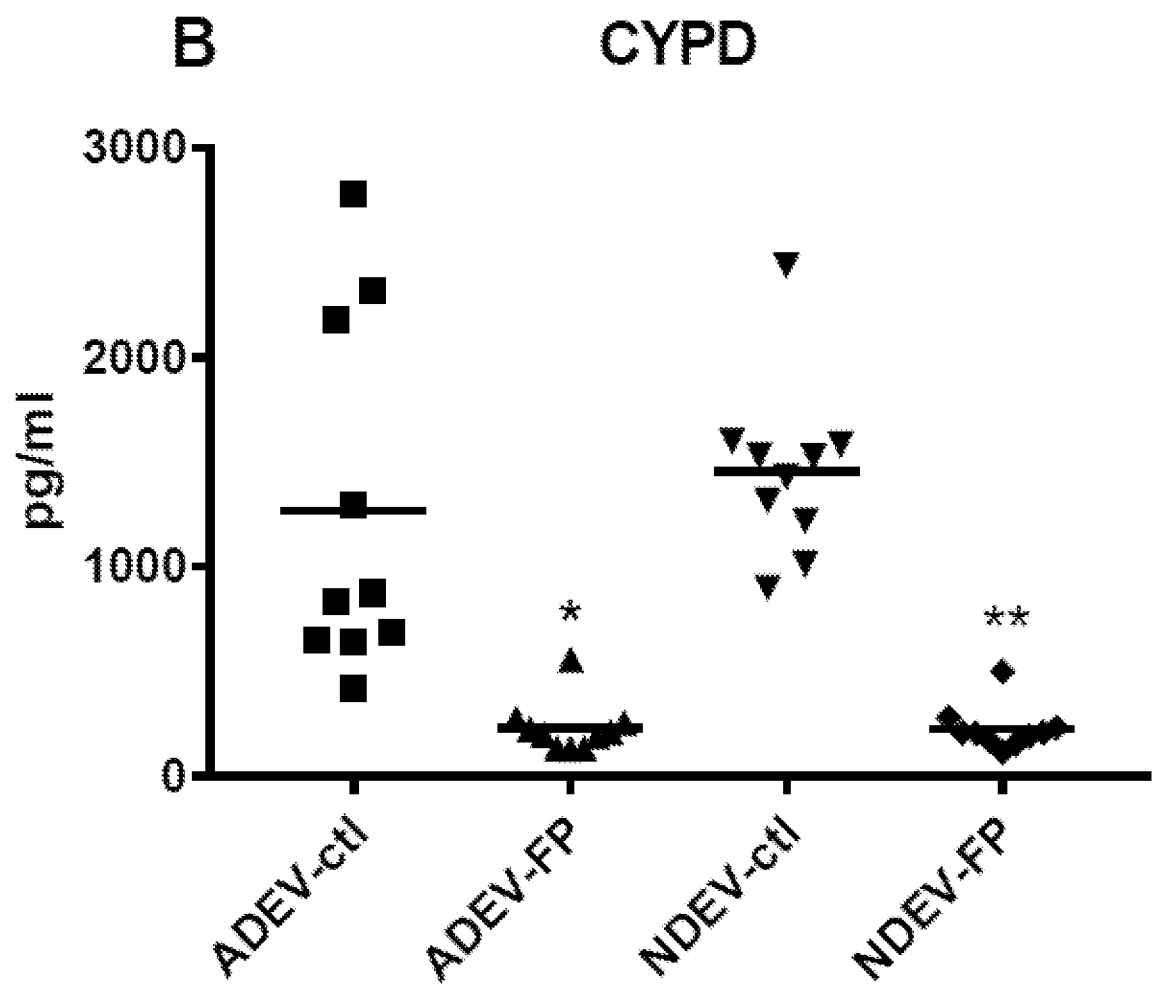
Figure 3C:
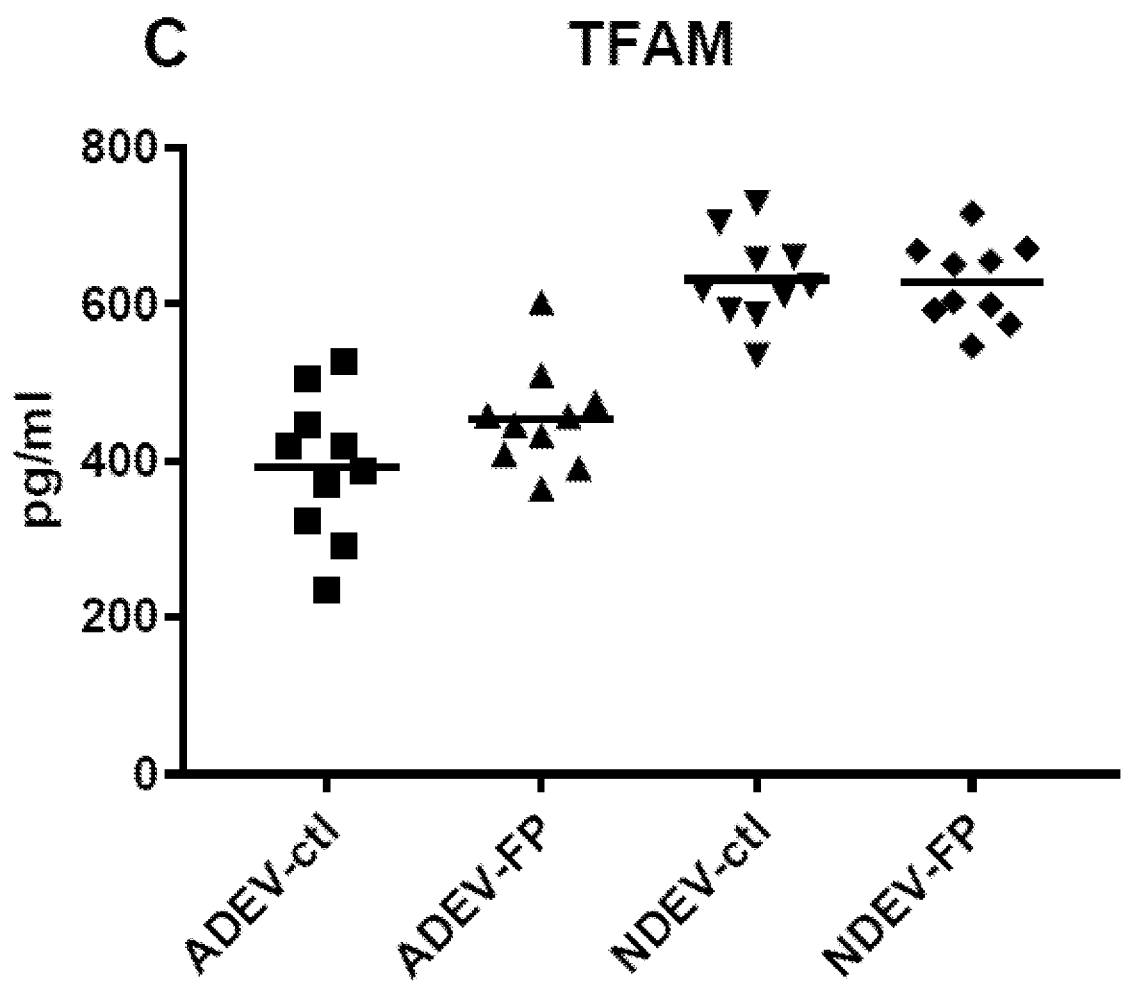
Figure 3D:
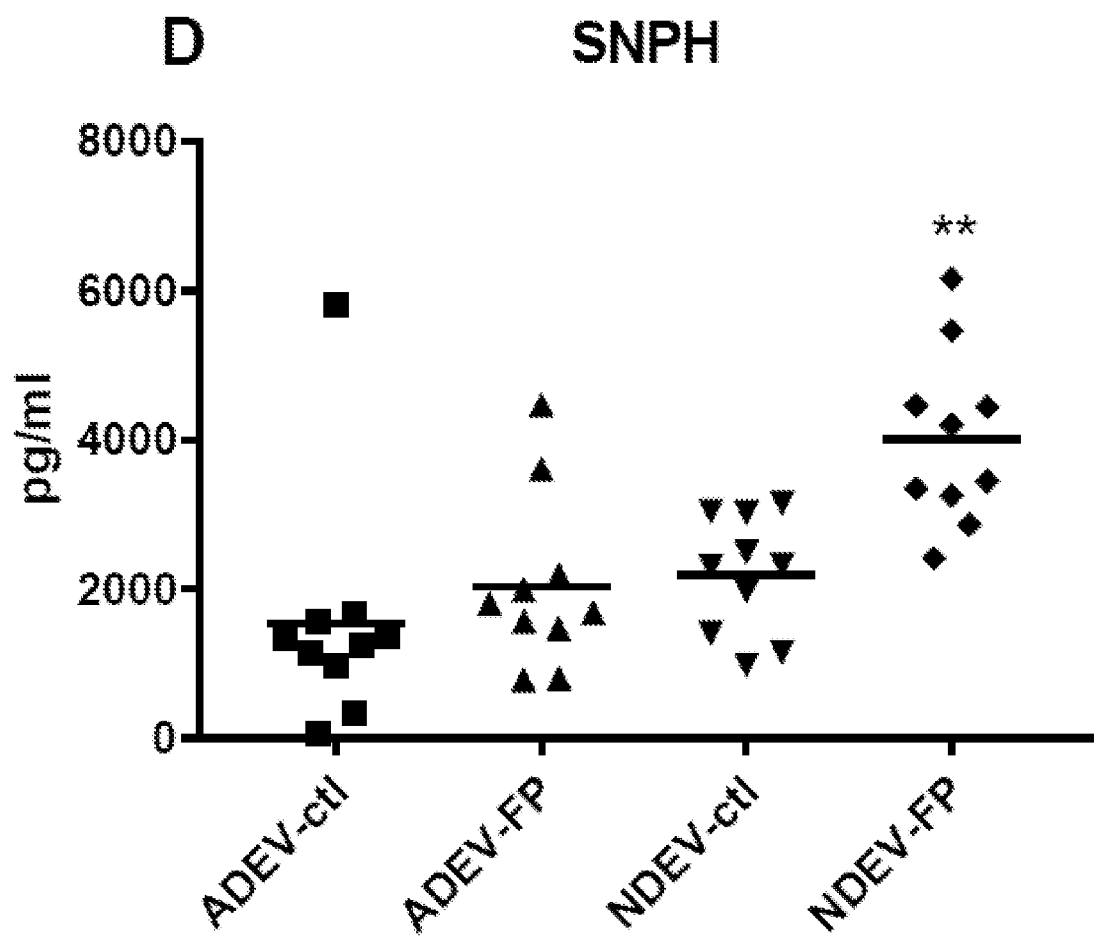
Figure 3E:
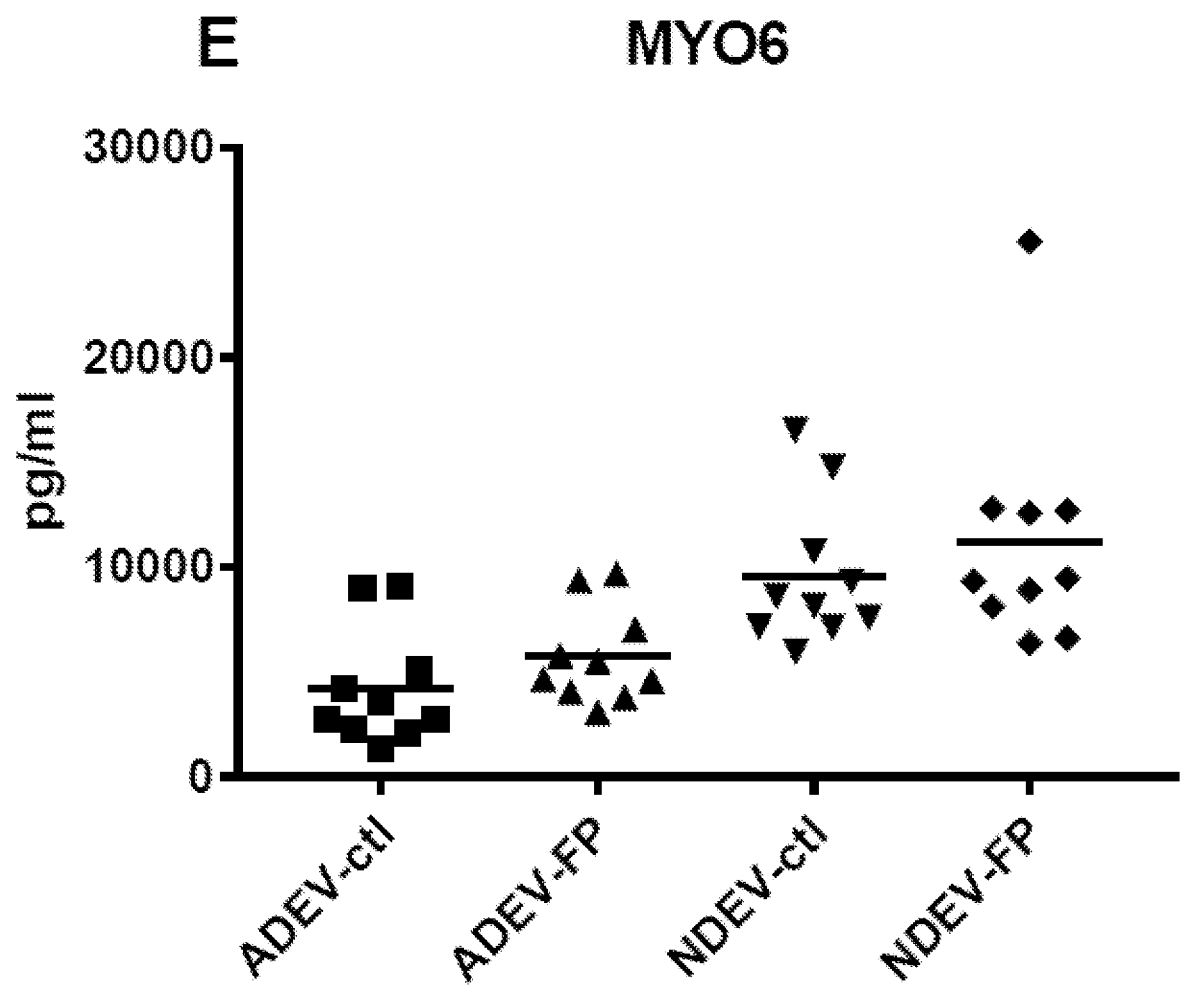

Astrocyte-derived leukemia inhibitory factor (LIF), a major neuroprotective cytokine, was detected at significantly lower levels in ADEs of FP patients than controls (FIG. 2G). In contrast, the predominantly microglial-derived inflammatory cytokine IL-6, that is high in plasma and brain tissues in many neural diseases, was present at only very low levels in ADEs with no difference between FP patients and controls (FIG. 2F).

These results showed that ADE and NDE levels of complement proteins and mitochondrial electron transport proteins are altered in subjects with psychosis. These results demonstrated that the methods of the present disclosure are useful for detecting biomarkers and measuring biomarker protein levels in astrocyte-derived exosomes and neuron-derived exosomes. These results further demonstrated that the methods of the present disclosure may be used to detect exosomal complement biomarkers, cytokine biomarkers, and/or mitochondrial electron transport biomarkers associated with pathogenesis of psychosis, including schizophrenia. These results further showed that methods of the present disclosure are useful for prognosis, diagnosis, treating or monitoring treatment of exosomal complement, cytokine, and mitochondrial electron transport abnormalities associated with psychosis. The results suggested that the methods of the present disclosure would be useful for treating psychosis.

Example 2: Abnormal Protein Levels in Neural-Derived Vesicles from First-Episode Psychosis Patients Neuroprotective and other mitochondrial electron transport proteins were detected and measured in astrocyte-derived exosomes and neuron-derived exosomes from subjects with psychosis as follows. Subjects were recruited from a Specialized Treatment Early in Psychosis (STEP) program of the Connecticut Mental Health Center (New Haven, CT). FP patients had suffered onset of psychosis within one year before study recruitment, with a range for the study of two weeks to one year. Ten consecutive FPs and ten healthy volunteer controls matched for age and sex were selected for this study (Table 1). Blood was obtained at the same time of day from all participants without fasting. Plasmas for exosome studies were collected off treatment at the time of admission and stored at 40° C.

TABLE 1

Participant Characteristics

| Group | Age, years (mean ± S.D.) | Male Female | Days from onset to admission (mean, range) | PANSS, Total (mean ± S.D.) | PANSS, General Psycho-pathology (mean ± S.D.) |
|---|---|---|---|---|---|
| Controls (n = 10) | 22.8 ± 3.44 | 7 3 | — | — | — |

TABLE 1-continued

Participant Characteristics

| Group | Age, years (mean ± S.D.) | Male Female | Days from onset to admission (mean, range) | PANSS, Total (mean ± S.D.) | PANSS, General Psycho-pathology (mean ± S.D.) |
|---|---|---|---|---|---|
| First Episode Psychotics (n = 10) | 21.5 ± 3.28 | 7 / 3 | 113, 14-338 | 98.2 ± 17.0 | 63.4 ± 13.4 |

PANSS, positive and negative symptom scale,

Enrichment of Plasma Neuron-Derived and Astrocyte-Derived Extracellular Vesicles Aliquots of 0.25 mL plasma were incubated with 0.1 mL of thromboplastin D (ThermoFisher Scientific, Waltham, MA) for 30 min at room temperature, followed by addition of 0.15 mL of calcium- and magnesium-free Dulbecco's balanced salt solution (DBS) with protease inhibitor cocktail (Roche, Indianapolis, IN) and phosphatase inhibitor cocktail (Thermo Fisher Scientific; DBS$^{++}$) as described (Goetzl et al. (2016) *Faseb J* 30, 3853-3859 and Goetzl et al. (2018) *Ann Neurol* 83, 544-552). After centrifugation at 3000×g for 30 minutes at 4° C., total exosomes were harvested from resultant supernatants by precipitation with 126 µL per tube of EXOQUICK (System Biosciences, Mountain View, CA) and centrifugation at 1500×g for 30 minutes at 4° C. To separately enrich neuron-derived extracellular vesicles (NDEVs) and astrocyte-derived extracellular vesicles (ADEVs), replicate preparations of total extracellular vesicles were resuspended in 0.35 mL of DBS$^{++}$ with either 2.0 µg of mouse anti-human CD171 (L1CAM neural adhesion protein) biotinylated antibody (clone 5G3; eBiosciences, San Diego, CA) or mouse anti-human glutamine aspartate transporter (ACSA-1) biotinylated antibody (Miltenyi Biotec, Auburn, CA), respectively, in 50 µL of 3% bovine serum albumin (BSA; 1:3.33 dilution of Blocker BSA 10% solution in DBS; ThermoFisher Scientific) per tube. After mixing for 60 minutes at room temperature, 10 µL of streptavidin agarose ULTRALINK resin (ThermoFisher Scientific) in 40 µL of 3% BSA were added to each tube followed by incubation for 30 minutes at room temperature with mixing. After centrifugation at 800×g for 10 minutes at 4° C. and removal of the supernatant, each pellet was suspended in 100 µL of cold 0.05M glycine-HCl (pH 3.0) by gentle mixing for 30 seconds and centrifuged at 4000×g for 10 minutes, all at 4° C. Supernatants then were transferred to clean tubes containing 25 µL of 10% BSA and 10 µL of 1 M Tris-HCl (pH 8.0) and mixed gently. An aliquot of 5 µL was removed from each tube for EV counts before addition of 370 µL of mammalian protein extraction reagent (M-PER, ThermoFisher Scientific). Resultant 0.5 mL lysates of NDEVs and ADEVs were frozen and thawed twice, and then stored at −80° C.

For counting and sizing of extracellular vesicles, each suspension was diluted 1:50 in phosphate-buffered saline (PBS). The mean diameter (nanometers) and concentration (particles per milliliter) of extracellular vesicles in each suspension were determined by nanoparticle tracking analysis (NTA) using the NANOSIGHT NS500 system with a G532 nm laser module and NTA 3.1 nanoparticle tracking software (Malvern Instruments, Malvern, United Kingdom). Camera settings were as follows: gain 366; shutter 31.48; and frame rate 24.9825 frames/s. Brownian motion was captured by performing 5 repeated 60 s video recordings. Mean±S.E.M. counts of ADEVs in immuno-selected suspensions were similar to those of past studies at 60.9±2.43× $10^9$/ml for controls and 613±2.80×$10^9$/ml for FP patients. Mean±S.E.M. counts of NDEs as in the past were 134±3.92×$10^9$/ml for controls and 135±5.69×$10^9$/ml for FP patients.

Quantification of NDEV and ADEV Protein

Astrocyte-derived extracellular vesicle (ADEV) and neuron-derived EV (NDEV) proteins were quantified by enzyme-linked immunosorbent assay (ELISA) kits for human tetraspanning exosome marker CD81, humanin (Cusabio Technology by American Research Products, Waltham, MA), glutamine synthetase, mitochondrial open-reading frame of the 12S rRNA-c (MOTS-c) (Cloud-Clone Corp by American Research Products), mitofusin 2 (MFN2), cyclophilin D (CYPD) (MyBioSource, San Diego, CA), transcription factor A mitochondrial (TFAM) (Aviva Systems Biology, San Diego, CA), syntaphilin (Wuhan Fine Biotech Co., Ltd., Wuhan, China by American Research Products), myosin VI (MYO6) (Abbkine by American Research Products), glial fibrillary acidic protein (Millipore-Sigma Corp., Burlington, MA), and neuron-specific enolase (R&D Systems-Bio-Techne, Minneapolis, MN).

Enzymatic activity of mitochondrial ATP synthase (complex V of the electron transport chain) was quantified by the oxidative conversion of NADH to NAD$^+$ by plate well immuno-adherent ATP synthase protein and consequent decrease over 120 min in absorbance at 340 nm (Abcam. Cambridge, MA). The mean value for all determinations of CD81 in each assay group was set at 1.00, and relative values of CD81 for each sample were used to normalize their recovery.

Results

Extracellular vesicle marker CD81-normalized levels of representative proteins in mitochondrial electron transport complexes I and III, but not IV, had been shown to be significantly lower in ADEVs and NDEVs of FP patients than controls (11). Existing data relevant to these levels of electron transport complexes suggested that ROS production would therefore be higher and ATP generation lower in mitochondria of both types of CNS cells of FP patients than controls (Adav et al. (2019) *Mol Brain* 12, 8). CD81-normalized enzymatic activity of ATP synthase (complex V) was significantly higher for ctl ADEVs than NDEVs and ATP synthase activity in NDEVs of FP patients was not significantly different than that in controls (Table 2). In contrast, ATP synthase activity in ADEVs of FP patients was significantly lower than that in controls, which is consistent with our previously quantified protein levels of mitochondrial electron transport complexes in ADEVs (Table 2).

TABLE 2

Lesser ATP Synthase Activity in ADEVs of FP Patients than Controls.

| | ATP Synthase Activity | | |
|---|---|---|---|
| Source | Controls (n = 10) | First Episode Psychotics (n = 10) | Unpaired t-test p value |
| ADEVs | 0.090 ± 0.030 | 0.014 ± 0.003 | 0.021 |
| NDEVs | 0.007 ± 0.002 | 0.009 ± 0.004 | 0.712 |

ATP Synthase activity is the decrease in absorbency units at 340 nm in 45 min at 30° C., after normalization for content of CD81.
The p value from an unpaired t test contrasting ATP synthase levels of control ADEVs with those of control NDEVs is 0.013.

A range of structurally distinct and functionally critical mitochondrial proteins were quantified in NDEVs and ADEVs of FP patients and controls to investigate whether the electron chain abnormalities identified are part of a broader mitochondrial disorder in this early course psychotic disorder. The CD81-normalized levels of mitofusin 2 (MFN2) and cyclophilin D (CYPD), but not of the mitochondrial transcription factor A (TFAM), were significantly lower in ADEVs and NDEVs of FP patients than controls (FIG. 3). The outer mitochondrial membrane GTPase MFN2 is required for mitochondrial fusion and numerous subsequent alterations in distribution and functions of mitochondria that favor increased ATP production (Filadi et al. (2018) *Cell Death & Disease* 9, 330). CYPD also is a broadly active regulator of protein maturation, many metabolic enzymes, electrical potential of the inner mitochondrial membrane, sensitivity of the mitochondrial permeability transition conductance pore, and activity of ATP synthase (Amanakis et al. (2020) *Front Physiol* 11, 595). In contrast, TFAM functions more narrowly by binding to mitochondrial DNA and determining its replication, abundance and stability (Kang et al. (2018) *FEBS Lett* 592, 793-811). Syntaphilin and myosin VI both are central to neural mitochondrial localization on axonal microtubules and presynaptic actin filaments (Kneussel et al. (2013) *Nat Rev Neurosci* 14, 233-247 and Lin et al. (2017) *Neuron* 94, 595-610 e596). Levels of myosin VI are significantly higher in NDEVs than ADEVs of FP patients and controls. The CD81-normalized level of syntaphilin were significantly higher in NDEVs, but not ADEVs, of FP patients than controls, whereas levels of myosin VI were no different in NDEVs or ADEVs of the two groups (FIG. 3).

Figure 4A:
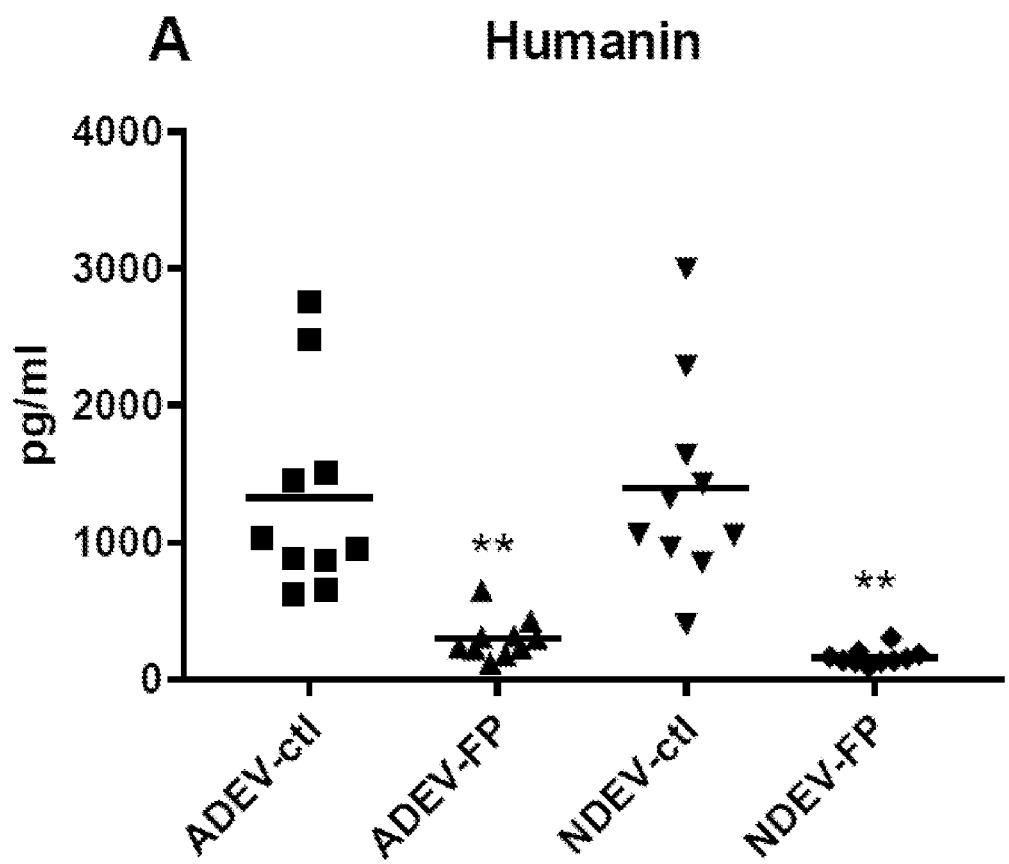
FIGS. 4A-4B set forth data showing abnormal levels of mitochondrial proteins with neuronal protective and metabolic effects in enriched populations of plasma ADEVs and NDEVs of patients with first-episode psychosis (FP). Each point represents the value for one study participant. The mean±S.E.M. of control (ctl) and FP groups, respectively, were 1324±236 pg/ml and 301±47.2 pg/ml for ADEVs ($p=0.0005$) and 1403±238 pg/ml and 165±18.5 pg/ml for NDEVs ($p<0.0001$) for humanin (A), and 168,008±45,797 pg/ml and 25,179±4,898 pg/ml for ADEVs ($p=0.0062$) and 169,267±12,247 pg/ml and 20,782±2,506 pg/ml for NDEVs (p<0.0001) for mitochondrial open-reading frame of the 12S rRNA-c (MOTS-c) (B). All values in A and B were normalized for content of the exosome marker CD81. Statistical significance of differences in values between Cntl and FP groups for NDEVs and ADEVs were calculated by two sample t tests; *, p<0.01; **, p<0.001.
Figure 4B:
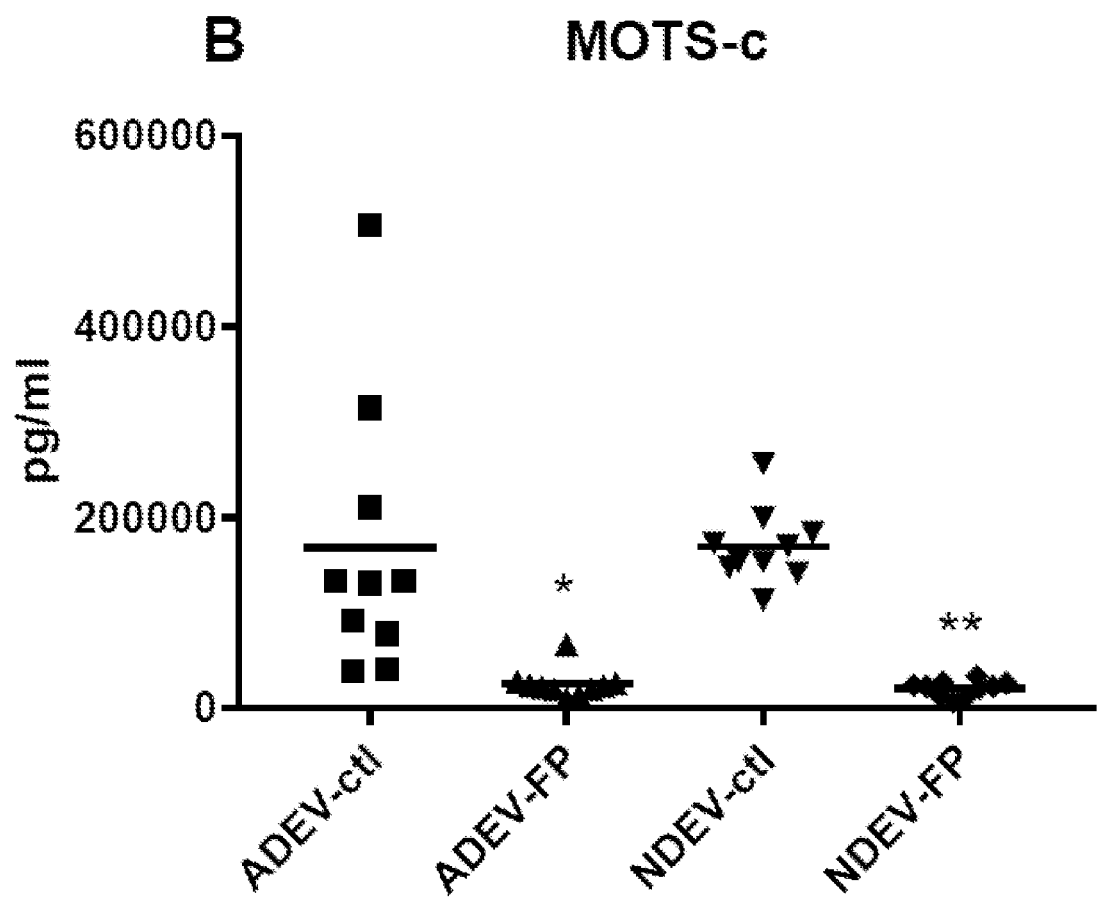

Two small mitochondrial proteins, humanin and mitochondrial open-reading frame of the 12S rRNA-c (MOTS-c), are encoded by short open reading frames in mitochondrial DNA and ribosomal RNA (rRNA) Hashimoto et al. (2001) *Proc Nat Acad Sci USA* 98, 6336-6341 and Lee et al. (2015) *Cell Metab* 21, 443-454). Humanin protects neurons from diverse challenges, suppresses apoptosis, preserves synaptic proteins, reduces neuroinflammation and supports aspects of glucose metabolism (Guo et al. (2003) *Nature* 423, 456-461; Yen et al. (2013) *J Mol Endocrinol* 50, R11-19; and Cobb et al. (2016) *Aging (Albany NY)* 8, 796-809). MOTS-c is predominantly a regulator of insulin sensitivity and other aspects of glucose metabolism in muscle cells and neurons (Lee et al. (2015) *Cell Metab* 21, 443-454). ADEV and NDEV levels of both humanin and MOTS-c were significantly lower in FP patients than controls (FIG. 4), suggesting lower resistance of neural cells from FP patients than controls to a range of adverse stresses.

To assess the consistency of determination of levels of the short open reading frame-encoded peptides, a second set of NDEVs and ADEVs was prepared from the same 20 plasmas. The mean±SEM of CD81-normalized levels of humanin in NDEVs were 1403±238 pg/ml and 1591±266 pg/ml for controls, and 165±18.5 pg/ml and 213±29.8 pg/ml for FP patients, and in ADEVs were 1324±236 pg/ml and 1382±180 pg/ml for controls, and 301±47.2 pg/ml and 289±36.8 pg/ml for FP patients, respectively, for the two preparations with no significant differences. The mean±SEM of CD81-normalized levels of MOTS-c in NDEVs were 169,267±12,247 pg/ml and 163,138±17,002 pg/ml for controls, and 20,782±2,506 pg/ml and 23,174±3,694 pg/ml for FP patients, and in ADEVs were 168,008±45,797 pg/ml and 152,844±34,480 pg/ml for controls, and 25,179±4,898 pg/ml and 28,940±2,664 pg/ml for FP patients, respectively, for the two preparations with no significant differences.

These results showed that ADE and NDE levels of mitochondrial proteins are altered in subjects with psychosis. These results demonstrated that the methods of the present disclosure are useful for detecting biomarkers and measuring biomarker protein levels in astrocyte-derived exosomes and neuron-derived exosomes. These results further demonstrated that the methods of the present disclosure may be used to detect exosomal mitochondrial biomarkers associated with pathogenesis of psychosis, including schizophrenia. These results further showed that methods of the present disclosure are useful for prognosis, diagnosis, treating or monitoring treatment of exosomal mitochondrial abnormalities associated with psychosis. The results suggested that the methods of the present disclosure would be useful for treating psychosis.

Example 3: Abnormal Protein Levels in Neural-Derived Vesicles from Psychosis Patients and Depressed Patients To characterize neuronal mitochondrial abnormalities in major depressive disorder (MDD), functional mitochondrial proteins (MPs) extracted from enriched plasma neuron-derived extracellular vesicles (NDEVs) of MDD participants (n=20) were quantified before and after eight weeks of treatment with a selective serotonin reuptake inhibitor as follows.

Major depressive disorder (MDD) outpatients not taking medications and mentally-healthy controls were recruited. Age ranges and sex distribution of mentally-healthy controls matched those of MDD patients are shown below in Table 3. Diagnoses were made according to the Structured Clinical Interview for DSM IV-TR Axis I Disorders (SCID), which was the DSM version used during this study, and were confirmed by a clinical interview with a board-certified psychiatrist. Depression symptom severity was assessed in MDD participants using the 17-item and 25-item Hamilton Depression Rating Scales (HDRS), where four MDD participants had a score lower than 17 for the first scale (two were 14, one was 13, and one was 16) and six MDD participants had a score lower than 25 for the second scale (three were 22 and three were 24), respectively. Exclusion criteria for MDD subjects were: bipolar disorder, psychotic symptoms during their current major depressive episode or other mood disorders, any eating disorder or post-traumatic stress disorder during the month before entering the study, and substance abuse or dependence including alcohol within six months before entering the study. Co-morbid anxiety disorders (except PTSD) were not exclusionary if MDD was considered the primary diagnosis. Control participants had no history of any DSM-IV-TR Axis I disorder as confirmed by SCID interview. Further, none of the study participants had acute illnesses or infections, chronic inflammatory disorders, neurological disorders, or any other major medical conditions considered to be potentially confounding, as determined by history, physical examinations and routine blood screening. All participants were free of any psychotropic medications, including antidepressants, hormone supplements (except if needed for hypothyroidism), steroid-containing birth control or other potentially interfering medications, and had not had any vaccinations for at least six weeks prior to enrollment in the study. None was taking vitamin supplements above the U.S. recommended minimum daily allowances. Short-acting sedative-hypnotics were not allowed within one week prior to participation. On the day of each study visit, all participants had to pass a urine toxicology screen (marijuana, cocaine, amphetamines, phencyclidine, opiates, methamphetamine, tricyclic antidepressants, and barbiturates) and a urine test for pregnancy in women of child-bearing potential.

TABLE 3

Demographics and clinical characteristics of study participants

|  | MDD, responder (n = 10) | | MDD, non-responder (n = 10) | | Healthy control (n = 10) |
|---|---|---|---|---|---|
| Age, years (mean ± SD) | 39.0 ± 9.4 | | 41.3 ± 11.6 | | 37.5 ± 10.5 |
| Sex, female/male | 6/4 | | 6/4 | | 5/5 |
|  | HDRS 17 | HDRS 25 | HDRS 17 | HDRS 25 |  |
| HDRS at baseline (mean ± SD) | 18.0 ± 3.5 | 26.3 ± 3.3 | 19.9 ± 2.9 | 29.8 ± 5.3 | ND |
| HDRS after treatment for 8 Weeks (mean ± SD) | 5.7 ± 4.0 | 7.8 ± 4.9 | 16.9 ± 3.4 | 23.6 ± 6.3 | ND |

HDRS is the Hamilton Depression Rating Scale; 17-variable version is the left-hand set and 25-variable version is the right-hand set.
There are no significant differences between study groups for age, sex or baseline pre-treatment HDRS.
Post-treatment HDRS values after 8 weeks of treatment are significantly lower for responders than non-responders.
ND = not done.

Selective Serotonin Reuptake Inhibitor (SSRI)-Treatment

MDD participants underwent 8 weeks of protocol-based open-label outpatient treatment with one of four SSRI antidepressants alone (NCT0028593S, https://www.clinicaltrials.gov/). Responders received sertraline (4), escitalopram (4) or fluoxetine (2) and non-responders received sertraline (4), escitalopram (2), fluoxetine (3) or citalopram (1) at the same sertraline equivalency doses. Compliance and clinical evaluations of drug tolerability were performed by a telephone check-in at the end of week 1 and an in-person check-in at the end of week 4 and week 8, at which times pill counts and plasma SSRI concentrations also were performed. Plasma SSRI concentrations were in the expected clinical range for each subject, suggesting excellent compliance. The severity of depressive symptoms, assessed by means of the HDRS, was the primary outcome measure repeated at the end of treatment (week 8). MDD participants were classified as "Responders" if their depression rating decreased by >50% from pre-treatment baseline and as "Non-Responders" if they showed lesser degrees of improvement. Ten Responders, ten representative Non-Responders and ten mentally-healthy age- and sex-matched controls were selected for this investigation from the total study group (see Table 3).

Blood Sampling

Participants were admitted as outpatients to the UCSF Clinical and Translational Science Institute (CTSI) between the hours of 0800 and 1100 after an overnight fast and instructed to sit quietly for 25-45 min before venipuncture for the baseline and 8-week post-treatment testing. Blood was collected into a lavender EDTA vacutainer tube, that was centrifuged at 1500×g and 4° C. for 10 min before plasma was removed, aliquoted into plastic Eppendorf tubes and stored at −80° C.

Enrichment of Plasma Neuron-Derived Extracellular Vesicles (NDEVs)

Aliquots of 0.25 mL plasma were incubated with 0.1 mL of thromboplastin D (ThermoFisher Scientific, Waltham, MA) for 30 min at room temperature, followed by addition of 0.15 mL of calcium- and magnesium-free Dulbecco's balanced salt solution (DBS) with protease inhibitor cocktail (Roche, Indianapolis, IN) and phosphatase inhibitor cocktail (Thermo Fisher Scientific; DBS$^{++}$). After centrifugation at 3000×g for 30 minutes at 4° C., total extracellular vesicles (EVs) were harvested from resultant supernatants by precipitation with 126 µL per tube of ExoQuick (System Biosciences, Mountain View, CA) and centrifugation at 1500×g for 30 minutes at 4° C.

To enrich neuron-derived EVs (NDEVs) including exosomes, replicate preparations of total extracellular vesicles were resuspended in 0.35 mL of DBS$^{++}$ with 2.0 µg of mouse anti-human CD171 (L1CAM neural adhesion protein) biotinylated antibody (clone 5G3; eBiosciences, San Diego, CA) in 50 µL of 3% bovine serum albumin (BSA; 1:3.33 dilution of Blocker BSA 10% solution in DBS; ThermoFisher Scientific) per tube. After mixing for 60 minutes at room temperature, 10 µL of streptavidin agarose Ultralink resin (ThermoFisher Scientific) in 40 µL of 3% BSA were added to each tube followed by incubation for 30 minutes at room temperature with mixing. After centrifugation at 800×g for 10 minutes at 4° C. and transfer to clean tubes of the supernatants containing exosomes from all sources except neurons, each pellet with NDEVs was suspended in 100 µL of cold 0.05M glycine-HCl (pH 3.0) by gentle mixing for 30 seconds and centrifuged at 4000×g for 10 minutes, all at 4° C. Glycine-HCl supernatants then were transferred to clean tubes containing 25 µL of 10% BSA and 10 µL of 1 M Tris-HCl (pH 8.0) and mixed gently. An aliquot of 5 µL was removed from each tube for EV counts before addition of 370 µL of mammalian protein extraction reagent (M-PER, ThermoFisher Scientific). Resultant 0.5 mL lysates of NDEVs were frozen and thawed twice, and then stored at −80° C. The total population of NDEV-depleted EV suspensions in initial supernatants from immunoprecipitation were re-precipitated with ExoQuick and suspended in 0.5 ml each of M-PER before freeze-thawing and storage at −80° C. before performing ELISAs.

To confirm the efficiency of immuno-enrichment, a portion of total initial EVs and of NDEV-depleted EV suspensions after absorption with anti-L1CAM and re-precipitation by ExoQuick for the ten control subjects also were extracted by M-PER for ELISA quantification of the exosome marker CD81 and the neuronal marker SNAP25 (AVIVA Systems Biology Corp., San Diego, CA). CD81 in the post-absorption residual EVs was a mean of 92.4% of that in the total EVs and SNAP2S in the post-absorption residual EVs was a mean of 9.1% of that in the total EVs, suggesting an approximate 10-fold enrichment of NDEVs. To examine the possibility of neural sources of mitochondrial protein abnormalities other than neurons, a protein of each major class in M-PER extracts of NDEV-depleted EV suspensions was quantified for the R-bsl, R-Tr and control sets.

For counting and sizing of extracellular vesicles, each suspension was diluted 1:50 in PBS. The mean diameter (nanometers) and concentration (particles per milliliter) of EVs in each suspension were determined by nanoparticle tracking analysis (NTA) using the Nanosight NS500 system with a G532 nm laser module and NTA 3.1 nanoparticle tracking software (Malvern Instruments, Malvern, United Kingdom). Mean±S.E.M. counts of NDEVs as in previous studies were 130+4.16×109/ml of plasma for Ctls. Comparing counts with corresponding levels of the exosome marker protein CD81 in extracts yielded Pearson Correlation Coefficients of >0.78 for all five sets of subjects.

Quantification of NDEV Proteins

NDEV proteins were quantified by enzyme-linked immunosorbent assay (ELISA) kits for human tetraspanning exosome marker CD81, subunit 6 of NADH-ubiquinone oxidoreductase (complex I), type 2 nuclear respiratory factor (NRF2), humanin (CUSABIO by American Research Products, Waltham, MA), myosin VI (MY06), subunit 10 of cytochrome b-c1 oxidase (complex III) (Abbkine Scientific C., Ltd. by American Research Products), PPAR γ coactivator-1α (PGC-1α), mitochondrial open-reading frame of the 12S rRNA-c (MOTS-c) (Cloud-Clone Corp. by American Research Products), mitofusin 2 (MFN2), nicotinamide mononucleotide adenylyl transferase 2 (NMNAT2), cyclophilin D (CYPD) (MyBioSource, San Diego, CA), syntaphilin (SNPH), leucine zipper EF-hand containing transmembrane 1 protein (LETM1), Sterile Alpha and TIR motif-containing protein 1 (SARM-1) (Wuhan FineTest Biotech Co. by American Research Products) and transcription factor A mitochondrial (TFAM) (Aviva Systems Biology, San Diego, CA). The mean value for all determinations of CD51 in each assay group was set at 1.00, and relative values of CD81 for each sample were used to normalize their recovery.

The same procedures were used for FP and MDD patients as well as controls to isolate NDEVs and quantify their mitochondrial proteins. All ELISAs were performed by two of the investigators without knowledge of the identity of any subject.

Statistics

After establishing that data were normally distributed, the significance of differences between baseline MDD levels and control values were calculated by an unpaired t test and of differences between levels after treatment and corresponding baseline values before treatment by a paired t test. Pearson Correlation Coefficient analyses were performed to assess relationships between HDRS values and NDEV mitochondrial protein levels at baseline and after treatment.

Results

Eleven mammalian neuron mitochondrial proteins were quantified in plasma neuron-derived extracellular vesicles (NDEVs, that include exosomes) of 20 MDD participants before and after an eight-week course of SSRI and in NDEVs of 10 matched controls before and after an eight-week period of observation (Table 3). Plasma NDEV levels of most of this same group of mitochondrial proteins in patients with a first episode of psychosis (FP) had been shown to differ significantly from those of age- and sex-matched mentally healthy controls.

Figure 5A:
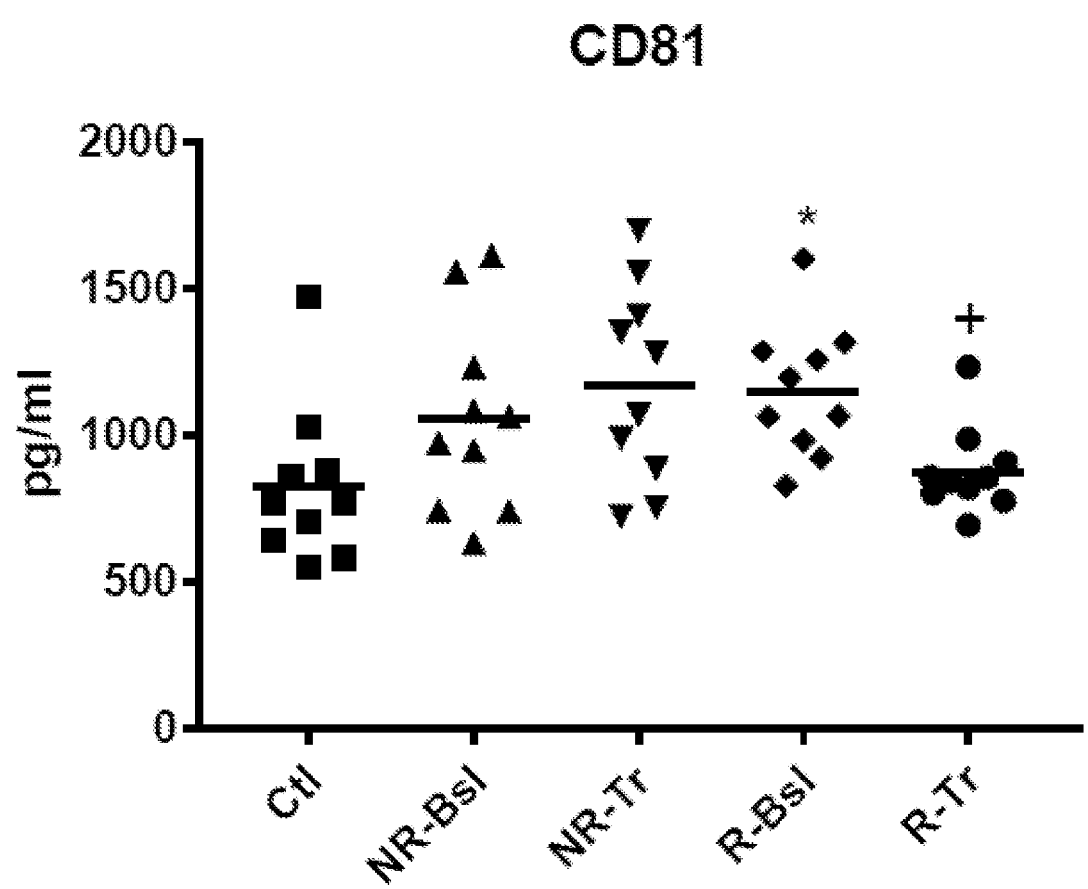
FIGS. 5A-5G set forth data showing NDEV levels of proteins involved in mitochondrial dynamics and other maintenance functions. Each point represents the value for one study participant. Statistical significance of baseline abnormalities were calculated relative to control values and of changes after treatment relative to respective baseline values before treatment; NS, not significant; +, p<0.05; *, p<0.01; **, p<0.001. The mean±S.E.M. of control subjects (Ctl), baseline of nonresponsive participants (NR-Bsl), after treatment of nonresponsive participants (NR-Tr), baseline of responsive participants (R-Bsl) and after treatment of responsive participants (R-Tr), respectively, were 825±85 pg/ml, 1058±105 pg/ml (NS), 1171±107 pg/ml (NS), 1151±72 pg/ml (0.0091) and 876±46 pg/ml (0.0157) for CD81(A); 1458±135 pg/ml, 1255±117 pg/ml (NS), 1426±149 pg/ml (NS), 1357±92 pg/ml (NS) and 1848±152 pg/ml (0.0039) for TFAM (B); 2623±266 pg/ml, 1120±89 pg/ml (<0.0001), 950±129 pg/ml (NS), 1452±117 pg/ml (0.0008) and 2572±234 pg/ml (0.0002) for MFN2 (C); 1415±125 pg/ml, 473±31 pg/ml (<0.0001), 438±30 pg/ml (NS), 424±32 pg/ml (<0.0001) and 651±65 pg/ml (0.0019) for CYPD (D); 1676±97 pg/ml, 758±188 pg/ml (0.0004), 440±44 pg/ml (NS), 523±60 pg/ml (<0.0001) and 1797±283 pg/ml (0.0008) for SNPH (E); 17,105±1684 pg/ml, 9659±1008 pg/ml (0.0013), 6269±745 pg/ml (0.0473), 4915±504 pg/ml (<0.0001) and 10,248±1144 pg/ml (0.0017) for MYO6 (F) and 2275±221 pg/ml, 1212±169 pg/ml (0.0012), 796±103 pg/ml (0.0412), 860±114 pg/ml (<0.0001) and 2197±248 pg/ml (0.0004) for LETM-1 (G).
Figure 5B:
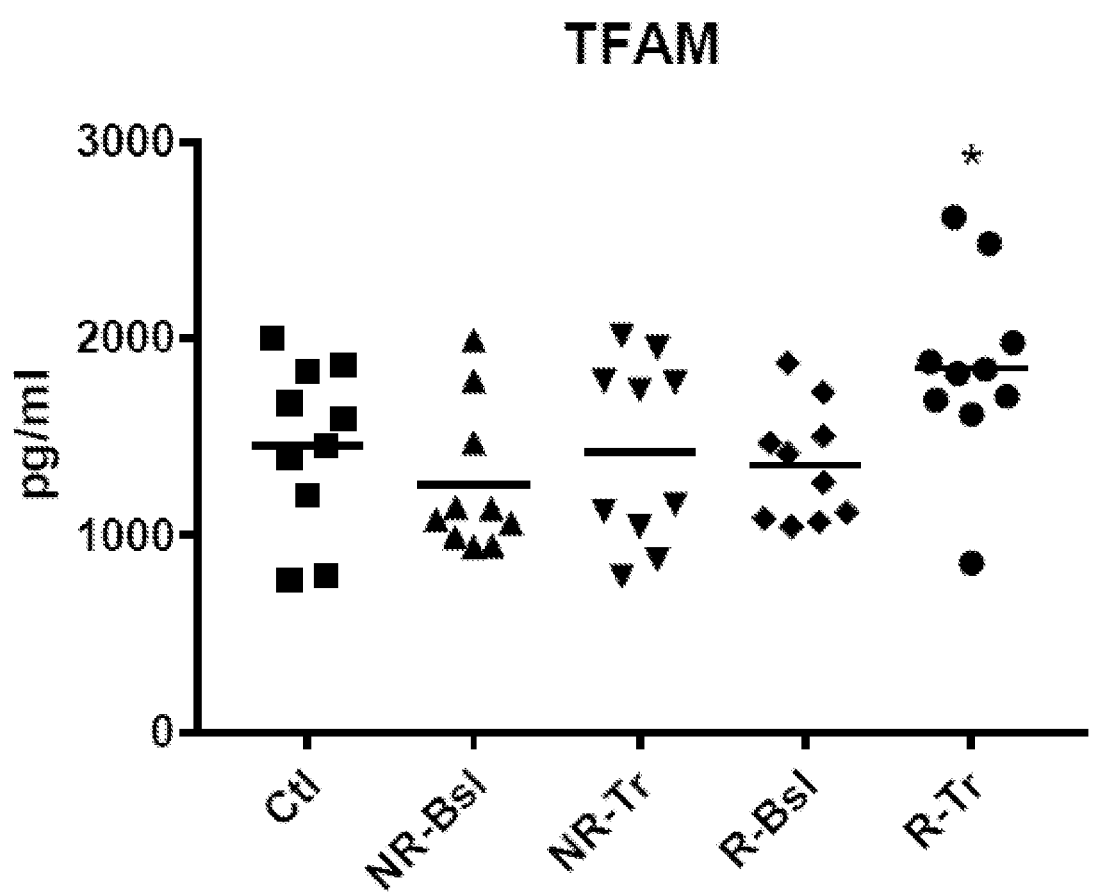
Figure 5C:
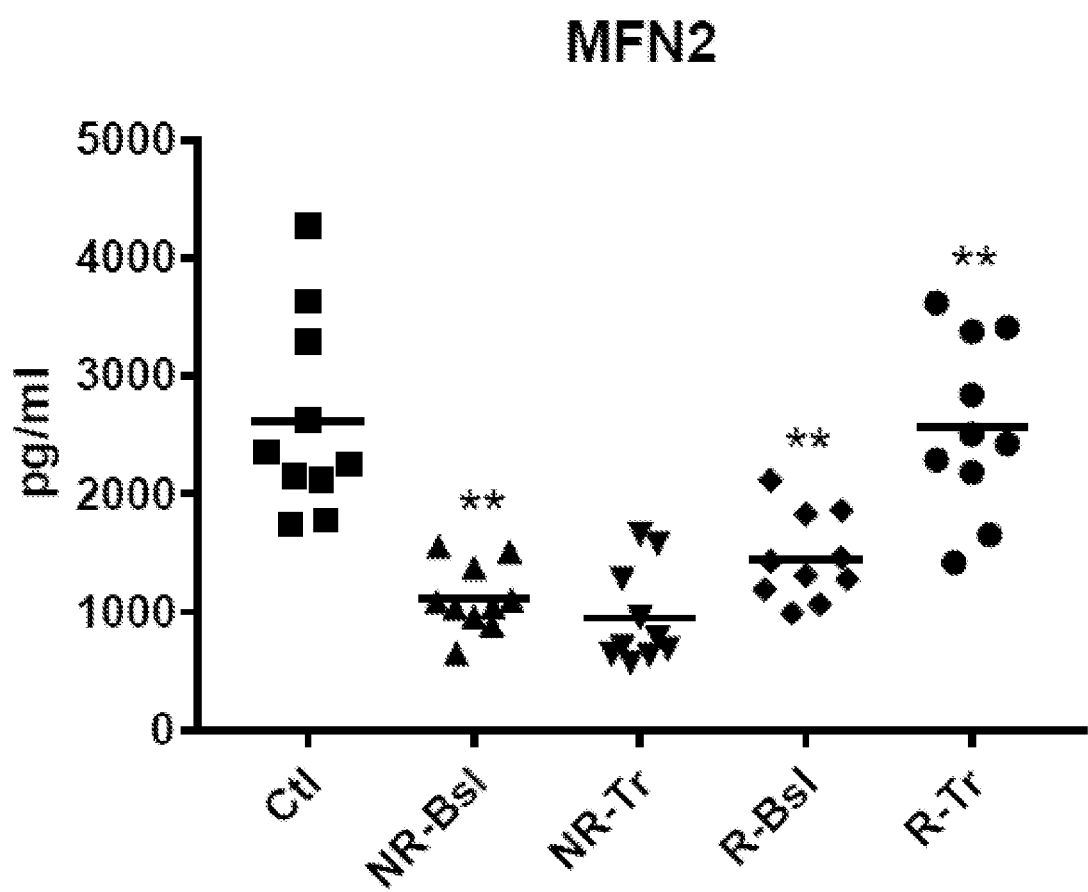
Figure 5D:
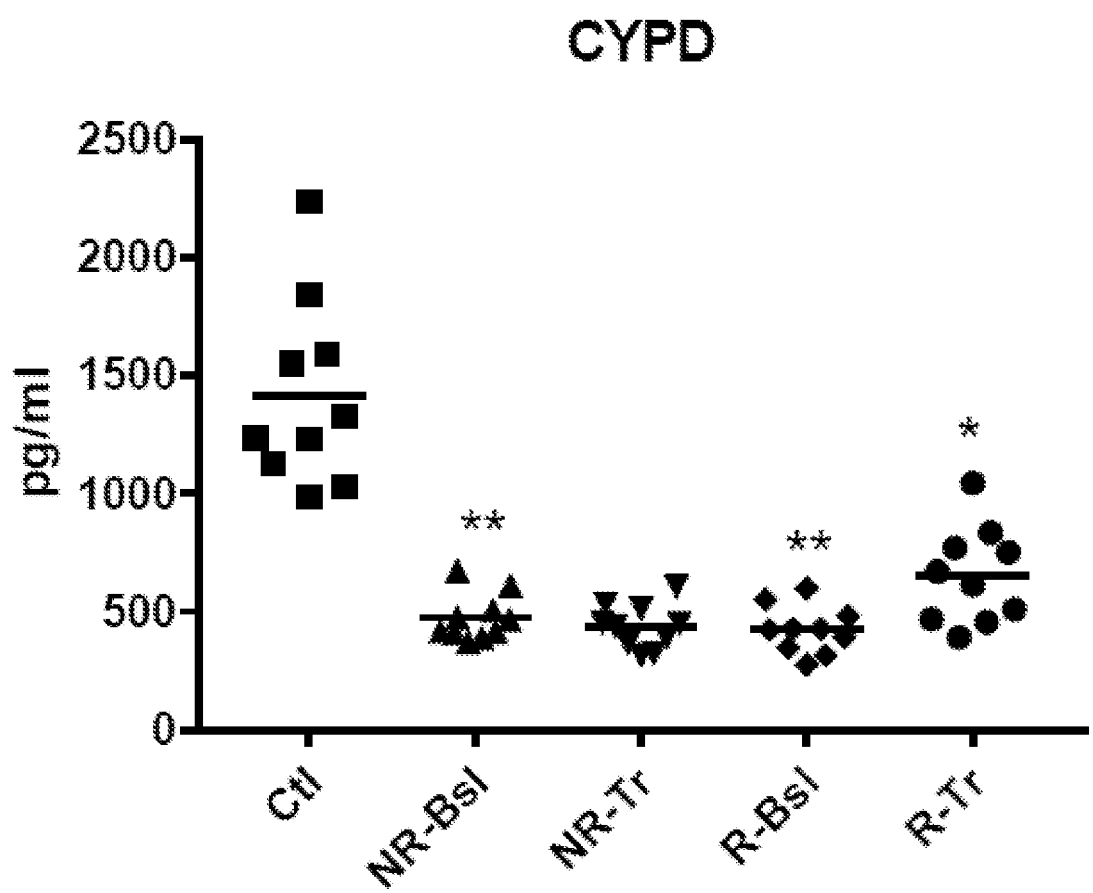
Figure 5E:
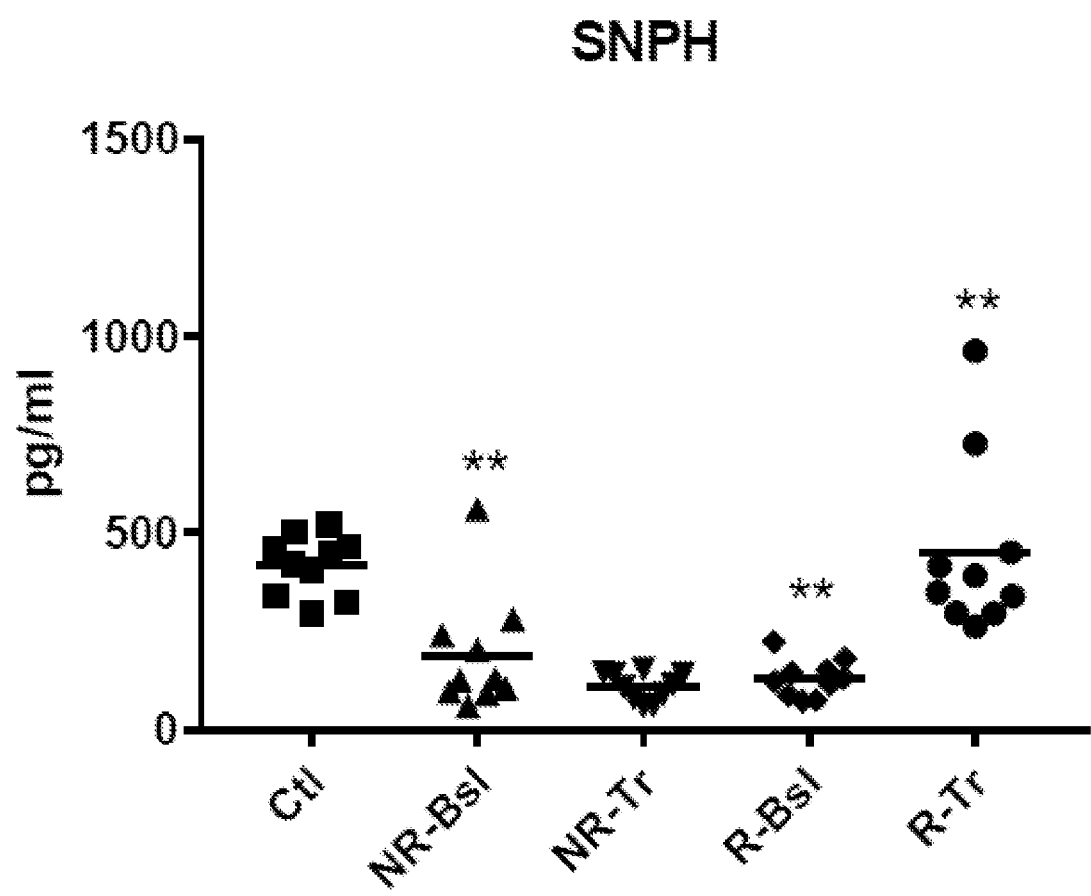
Figure 5F:
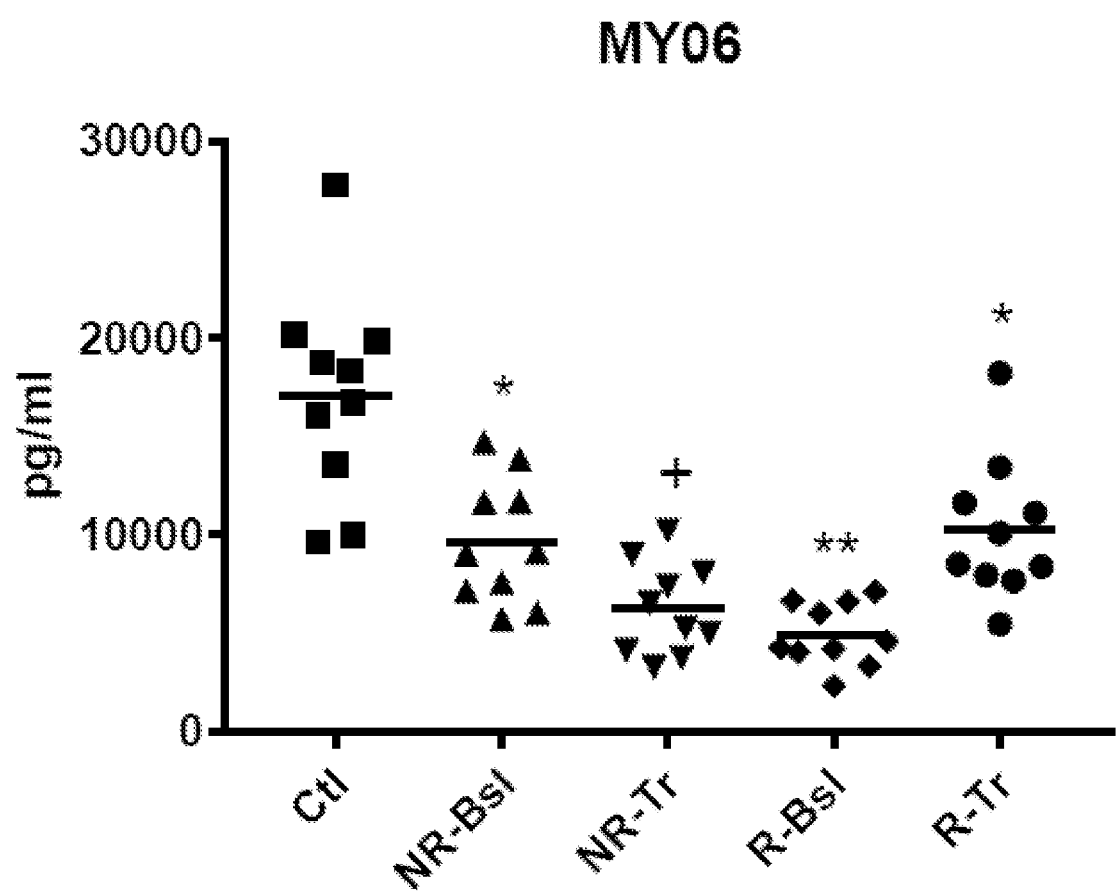
Figure 5G:
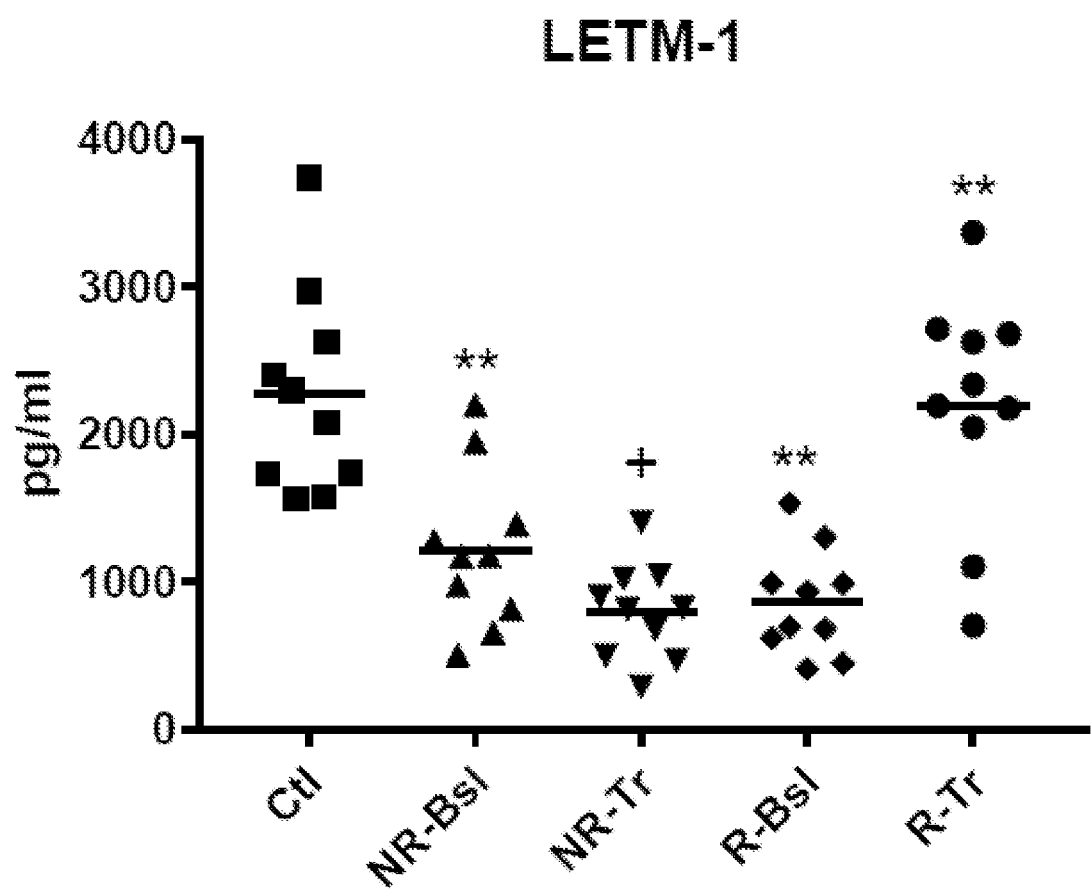

NDEV levels of neuronal proteins included the exosome marker CD81, which is used to normalize levels of all other NDEV proteins (see FIGS. 5A-1G). For CD81, the only alteration was a slight increase above normal controls (Ctl) of the baseline pretreatment level for those who responded to treatment (R-Bsl) and a return to control level after treatment (R-Tr) (FIG. 5A). The first class of mitochondrial proteins in NDEVs are involved in mitochondrial dynamics and functional maintenance. This class includes the prominent transcription factor TFAM, CYPD regulator of membrane potential, metabolism and pore permeability, MFN2 membrane GTPase required for mitochondrial fusion and distribution, and the tethering proteins SNPH and MY06 that anchor mitochondria to microtubules in axons and to microfilaments in pre-synaptic areas. The only abnormality in TFAM was a slight increase for the R-Tr group above their normal R-Bsl level (FIG. 5B). In contrast, both baseline MFN2 and CYPD levels for NR-Bsl and R-Bsl groups were strikingly lower than those of the Ctl group (FIGS. 5C and 5D). After treatment, the R-Tr level of CYPD returned statistically significantly but partially and that of MFN2 returned completely to their respective Cd levels. Neither the CYPD nor MFN2 levels of the NR-Tr group were altered significantly. Similarly, baseline levels of both SNPH and MY06 for NR-Bsl and R-Bsl groups were strikingly lower than those of the Cd group (FIGS. 5E and 5F). The R-Tr levels of SNPH and MY06 returned statistically significantly and partially or completely to the respective Ctl level. Neither the SNPH nor MY06 levels of the NR-Tr group were altered significantly. LETM1 levels are shown in FIG. 5G.

Figure 6A:
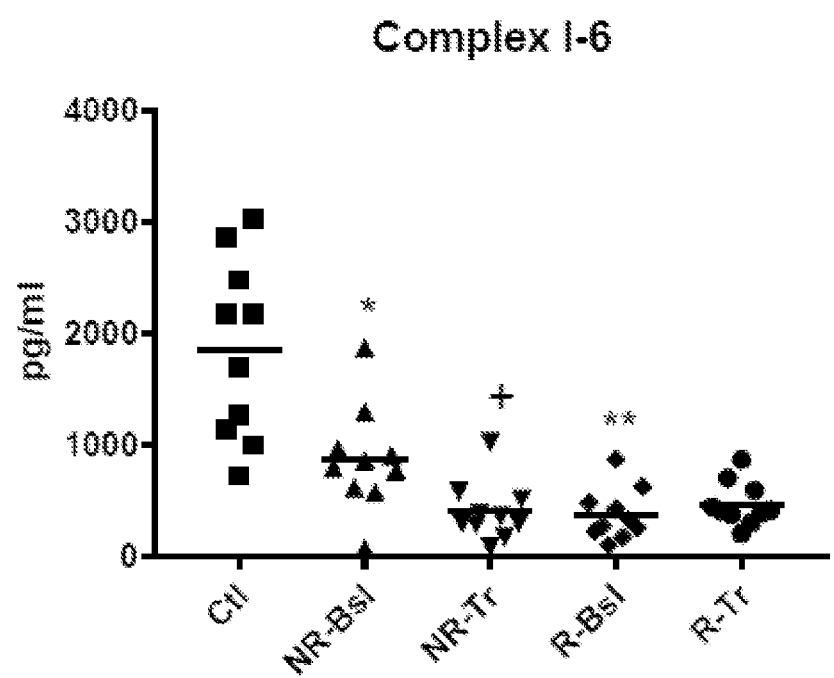
FIGS. 6A-6D set forth data showing NDEV levels of proteins involved in mitochondrial generation of energy. Statistical methods and symbols are the same as in FIG. 1. The mean±S.E.M. of Ctl, NR-Bsl, NR-Tr, R-Bsl and R-Tr groups, respectively, were 1852±255 pg/ml, 867±149 pg/ml (0.0037), 401±83 pg/ml (0.0147), 374±74 pg/ml (<0.0001) and 465±63 pg/ml (NS) for Complex 1-subunit 6 (ND6) (A); 815±83 pg/ml, 258±35 pg/ml (<0.0001), 199±21 pg/ml (NS), 191±25 pg/ml (<0.0001) and 710±54 pg/ml (<0.0001) for Complex III-subunit 10 (B); 17,908±2171 pg/ml, 6200±1011 pg/ml (<0.0001), 4345±507 pg/ml (NS), 5534±711 pg/ml (<0.0001) and 23,564±3932 pg/ml (0.0014) for NMNAT2 (C); and 466±74 pg/ml, 2063±351 pg/ml (0.0002), 2695±1047 pg/ml (NS), 1908±416 pg/ml (0.0031) and 664±156 pg/ml (0.0368) for SARM1 (D).
Figure 6B:
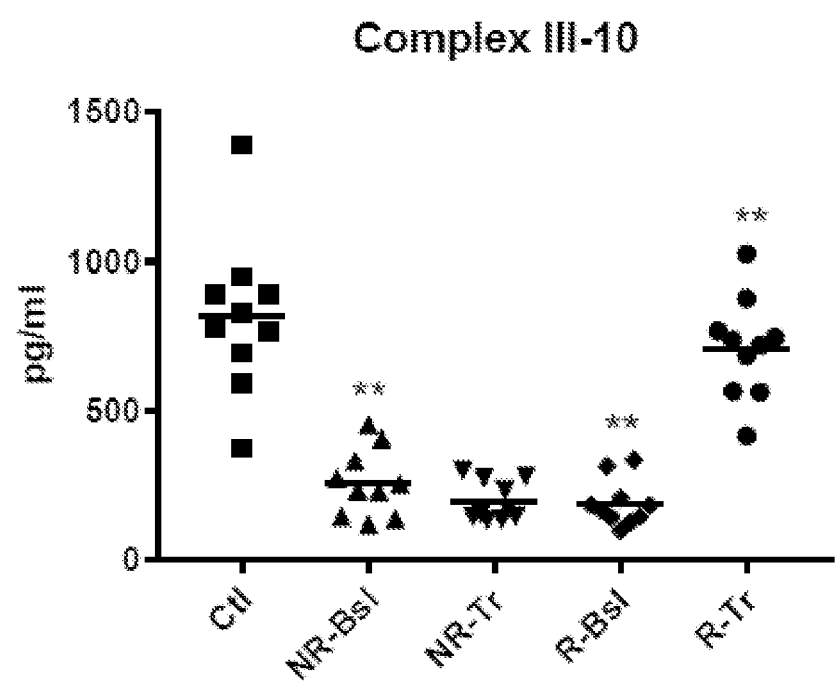
Figure 6C:
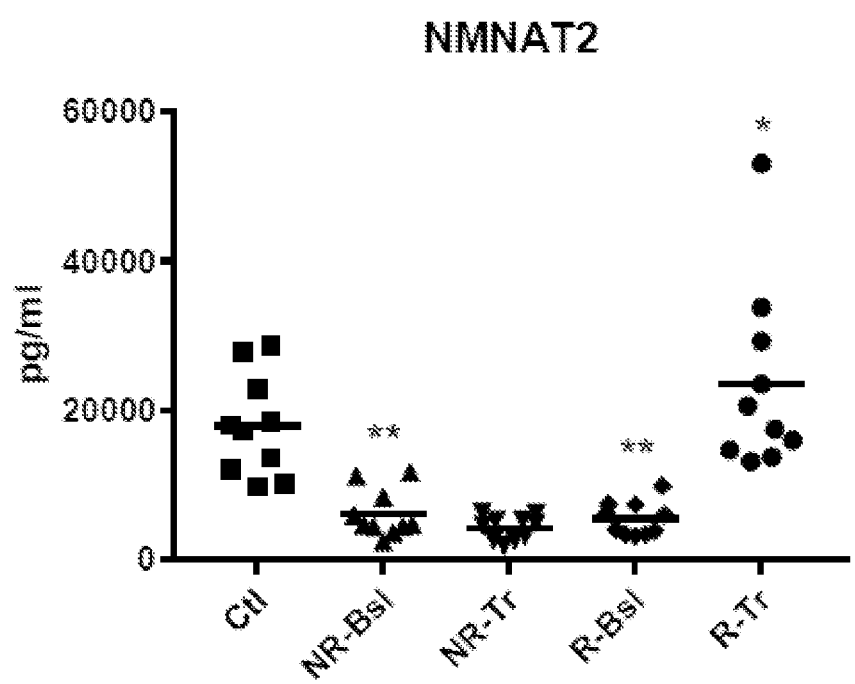
Figure 6D:
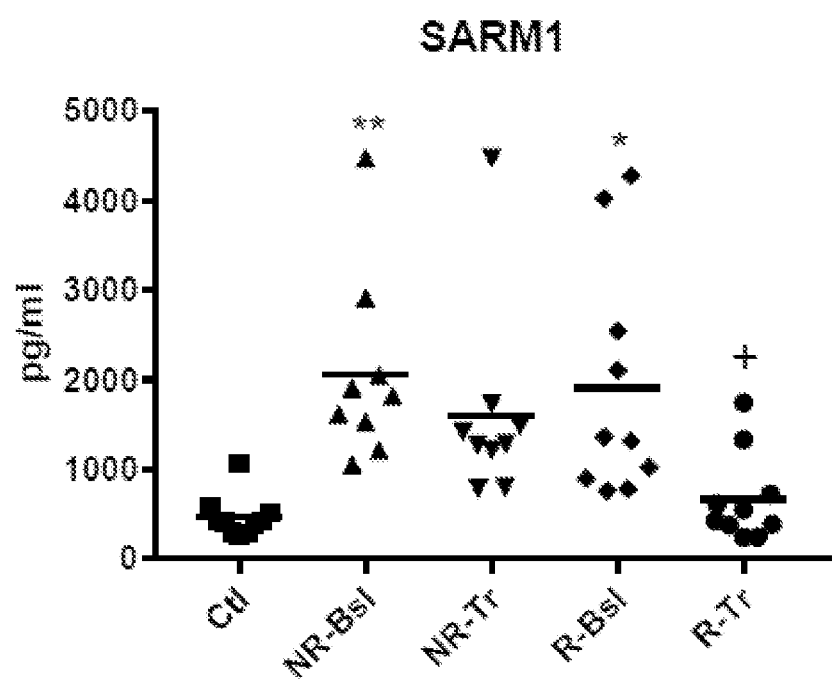

The second class of neuron mitochondrial proteins am critical for energy generation and include the inner membrane electron-transferring complexes NADH dehydrogenase complex I (subunit 6) and cytochrome b-c1 complex III (subunit 10), nicotinamide mononucleotide adenylyl transferase 2 (NMNAT2), which is the final synthetic enzyme required for de novo production of NADH prior to amidation, and the pro-neurodegenerative factor Sterile Alpha and TIR motif-containing protein 1 (SARM1) that has a prominent NADase activity (FIGS. 6A-6D). The importance of NMNAT2 and SARM1 for energy generation derives from their roles in establishing the mitochondrial total concentration of NADH plus $NAD^+$ that is as critical as the NADH/$NAD^+$ ratio. The NR-Bsl and R-Bsl levels of both oxidative phosphorylation complexes I and III were significantly lower than the corresponding Ctl levels (FIGS. 6A and 6B). For group R-Tr, the complex III protein level was completely corrected by treatment, whereas that of complex I protein was not altered significantly. For group NR-Tr, the complex III protein level was not affected by treatment and the level of complex I protein was further decreased significantly. For the two enzymes involved in determining mitochondrial NADH plus $NAD^+$ concentration, levels of NMNAT2 were statistically significantly lower (FIG. 6C) and of SARM1 were significantly higher (FIG. 6D) for both the NR-Bsl and R-Bsl groups relative to that of Ctls. Bsl levels of both proteins were normalized for the R-Tr group with no changes for the NR-Tr group.

Figure 7A:
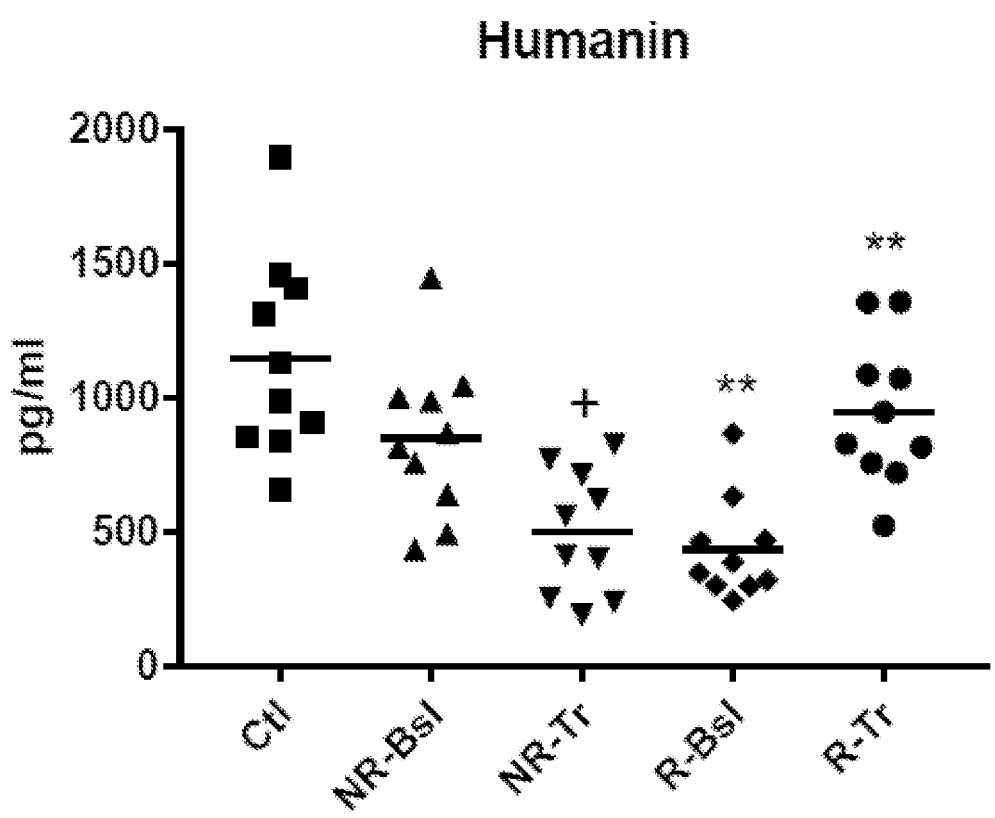
FIGS. 7A-7B set forth data showing NDEV levels of proteins involved in mitochondrial biogenesis and in mitochondrial regulation of neuronal metabolism and survival. Statistical methods and symbols are the same as in FIG. 1. The mean±S.E.M. of Ctl, NR-Bsl, NR-Tr, R-Bsl and R-Tr groups, respectively, were 1146±118 pg/ml, 850±93.8 pg/ml (NS), 500±73.4 pg/ml (0.0308), 434159.9 pg/ml (<0.0001) and 947±86.1 pg/ml (<0.0001) for humanin (A); 155,054±13,122 pg/ml, 24,396±2917 pg/ml (<0.0001), 17,126±1757 pg/ml (NS), 26,252±4184 pg/ml (<0.0001) and 145,947±8370 pg/ml (<0.0001) for MOTS-c (B).
Figure 7B:
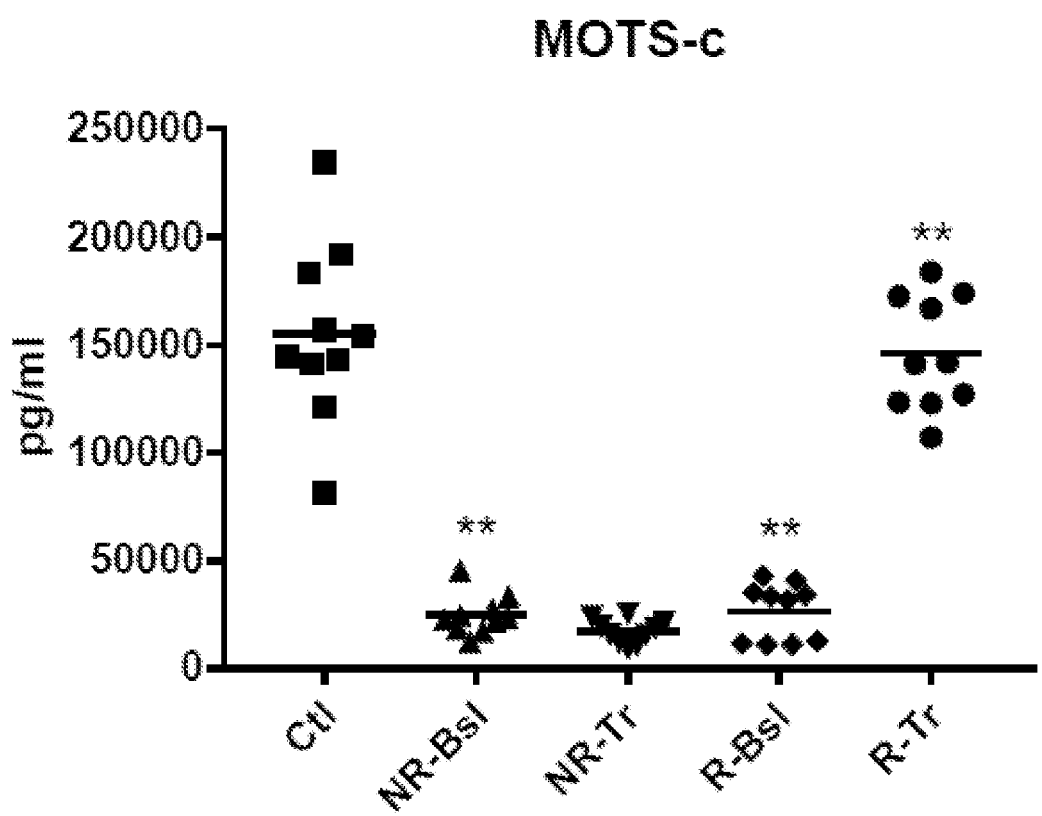

The third class of neuron mitochondrial proteins include neuroprotective humanin (FIG. 7A) and neuron metabolic regulatory MOTS-c (FIG. 7B), that both are encoded by mitochondrial ribosomal RNAs. For the R-Bsl group, the levels of both are statistically significantly lower than those of Ctls and are normalized by treatment for the R-Tr group. For the NR-Bsl group, the level of MOTS-c but not humanin is statistically significantly depressed relative to that of the Ctl group. After treatment the NR-Tr level of MOTS-c is unchanged and that of humanin is lowered further. PGC-1α and NRF2 are central regulators of mitochondrial biogenesis. NDEV levels of Control, NR-Bsl, NR-Tr, R-Bsl and R-Tr groups, respectively, were 1146±118 pg/ml, 950±93.8 pg/ml (NS), 500±73.4 pg/ml (0.0308), 434±59.9 pg/ml (<0.0001) and 947±86.1 pg/ml (<0.0001) for PGC-1α; and 155,054±13,122 pg/ml, 24,396±2917 pg/ml (<0.0001), 17.126±1757 pg/ml (NS), 26,252±4184 pg/ml (<0.0001) and 145,947±8370 pg/ml (<0.0001) for NRF2. Table 4 shows a comparison of alterations in NDEV levels of mitochondrial proteins in untreated first episode of psychosis (FP) and in untreated baseline for major depressive disorder (MDD).

TABLE 4

| Class of mitochondrial analytes | FP | MDD NR-Bsl/R-Bsl |
|---|---|---|
| 1. Dynamics and maintenance functions | | |
| TFAM | ND | ND |
| MFN2 | ↓82 | ↓57/45 |
| CYPD | ↓84 | ↓67/70 |
| SNPH | ↑183 | ↓55/69 |
| MYO6 | ND | ↓44/71 |
| 2. Energy generation | | |
| Complex I-6 | ↓66 | ↓53/80 |
| Complex III-10 | ↓55 | ↓68/77 |
| NMNAT 2 | ↓34 | ↓65/69 |
| SARM 1 | ND | ↑443/409 |
| 3. Metabolic regulation and cellular survival | | |
| Humanin | ↓88 | ↓26/62 |
| MOTS-c | ↓88 | ↓84/83 |

Each value represents the mean percentage change from controls for FP patients and for baseline levels of MDD groups non-responsive (NR-Bsl) and responsive (R-Bsl) to therapy.
ND is no difference between mentally ill participants and controls.
Up arrows and down arrows indicate increases and decreases of mitochondrial protein levels in mental illness, respectively.

These results showed that NDEV levels of mitochondrial proteins am altered in subjects with major depressive disorder. These results demonstrated that the methods of the present disclosure are useful for detecting biomarkers and measuring biomarker protein levels in neuron-derived extracellular vesicles. These results further demonstrated that the methods of the present disclosure may be used to detect extracellular vesicle mitochondrial biomarkers associated with pathogenesis of depression, including major depressive disorder (MDD). These results further showed that methods of the present disclosure am useful for prognosis, diagnosis, treating or monitoring treatment of extracellular vesicle mitochondrial abnormalities associated with depression. The results suggested that the methods of the present disclosure would be useful for treating depression, including MDD.

Various modifications of the disclosure, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A method of measuring biomarkers in exosomes in a biological sample comprising: a) providing a biological sample comprising exosomes from a subject; b) enriching the sample for exosomes; and c) detecting the presence of the biomarkers in the exosomes, wherein the biomarkers comprise glial fibrillary acidic protein, subunit 6 of NADH-ubiquinone oxidoreductase (complex I), subunit 1 of cytochrome C oxidase (complex IV), subunit 1 of NADH-ubiquinone oxidoreductase (complex I), subunit 10 of cytochrome b-cl oxidase (complex III), humanin, and mitochondrial open-reading frame of the 12S rRNA-c (MOTS-c).

2. The method of claim 1, wherein the biomarkers further comprise human tetraspanning exosome marker CD81, decay-accelerating factor (CD55), glutamine synthetase, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), Sterile alpha and TIR motif containing 1 (SARM 1), Transcription factor A, mitochondrial (TFAM), Nicotinamide nucleotide adenylyltransferase 2 (NMNAT 2), Peroxisome proliferator-activated receptor gamma coactivator 1-alpha (PGC-1α), and/or Nuclear factor erythroid 2-related factor 2 (NRF2).

3. The method of claim 1, wherein the exosomes are astrocyte-derived exosomes and/or neuron-derived exosomes.

4. The methods of claim 1, wherein the biological sample is selected from the list consisting of whole blood, plasma, serum, lymph, amniotic fluid, urine, and saliva.

5. The method of claim 1, wherein the detecting the presence of the marker in the biological sample comprises detecting the amount of the marker in the biological sample.

6. The method of claim 1, wherein the subject has or is suspected of having depression or psychosis.

7. The method of claim 1, wherein the subject has or is suspected of having major depressive disorder or schizophrenia.

8. A method of measuring biomarkers in exosomes in a biological sample comprising: a) providing a biological sample comprising exosomes from a subject having depression or psychosis; b) isolating exosomes from the biological sample; and c) detecting the presence of biomarkers in the exosomes, wherein the biomarkers comprise glial fibrillary acidic protein, subunit 6 of NADH-ubiquinone oxidoreductase (complex I), subunit 1 of cytochrome C oxidase (complex IV), subunit 1 of NADH-ubiquinone oxidoreductase (complex I), subunit 10 of cytochrome b-cl oxidase (complex III), humanin, and mitochondrial open-reading frame of the 12S rRNA-c (MOTS-c).

9. The method of claim 8, wherein the isolating exosomes from the biological sample comprises: contacting the biological sample with an agent under conditions wherein the exosomes present in the biological sample bind to the agent to form an exosome-agent complex; and isolating the exosomes from the exosome-agent complex to obtain a sample containing the exosomes, wherein the purity of the exosomes present in said sample are greater than the purity of the exosomes present in said biological sample.

10. The method of claim 8, wherein the biomarkers further comprise human tetraspanning exosome marker CD81, decay-accelerating factor (CD55), glutamine synthetase, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), Sterile alpha and TIR motif containing 1 (SARM 1), Transcription factor A, mitochondrial (TFAM), Nicotinamide nucleotide adenylyltransferase 2 (NMNAT 2), Peroxisome proliferator-activated receptor gamma coactivator 1-alpha (PGC-1α), and/or Nuclear factor erythroid 2-related factor 2 (NRF2).

11. The method of claim 8, further comprising the step of determining a treatment course of action based on the detection of the one or more biomarkers.

12. The method of claim 8, wherein the subject has or is suspected of having depression or psychosis.

13. The method of claim 8, wherein the subject has or is suspected of having schizophrenia or major depressive disorder.

14. A method for treating a subject, comprising the steps of: providing a biological sample from a subject having or suspected of having depression or psychosis, wherein the sample comprises exosomes; measuring the level of the biomarkers in the exosomes, wherein the biomarkers comprise glial fibrillary acidic protein, subunit 6 of NADH-ubiquinone oxidoreductase (complex I), subunit 1 of cytochrome C oxidase (complex IV), subunit 1 of NADH-ubiquinone oxidoreductase (complex I), subunit 10 of cytochrome b-cl oxidase (complex III), humanin, and mitochondrial open-reading frame of the 12S rRNA-c (MOTS-c), wherein an altered level of the biomarkers in the sample relative to the level in a control sample is indicative of a need for treatment; and administering an effective amount of an agent to the subject thereby treating the depression or psychosis in the subject, wherein the agent is a SOD1 mimetic, a C3 convertase inhibitor, a LIF supplement, a LIF receptor agonist, or a ROS scavenger.

15. The method of claim 14, wherein the biomarkers further comprise human tetraspanning exosome marker CD81, decay-accelerating factor (CD55), glutamine synthetase, complement fragment C3b, TCC C5b-9, superoxide dismutase 1 (SOD1), CD59, IL-6, neuron-specific enolase, leukemia inhibitory factor (LIF), mitochondrial electron transport chain complexes I and III, ATP synthase, cyclophilin D (CYPD), mitofusin 2 (MFN2), myosin VI (MYO6), syntaphilin (SNPH), Sterile alpha and TIR motif containing 1 (SARM 1), Transcription factor A, mitochondrial (TFAM), Nicotinamide nucleotide adenylyltransferase 2 (NMNAT 2), Peroxisome proliferator-activated receptor gamma coactivator 1-alpha (PGC-1α), and/or Nuclear factor erythroid 2-related factor 2 (NRF2).

16. The method of claim 14, wherein the exosomes are astrocyte-derived exosomes and/or neuron-derived exosomes.

* * * * *